United States Patent
Bergmann

(10) Patent No.: US 10,221,238 B2
(45) Date of Patent: *Mar. 5, 2019

(54) METHOD OF MODULATING THE ACTIVITY OF ADRENOMEDULLIN IN A SUBJECT IN NEED OF THERAPEUTIC INTERVENTION FOR ORGAN DYSFUNCTION OR ORGAN FAILURE ASSOCIATED WITH ADRANOMEDULLIN (ADM) ACTIVITY BY ADMINISTERING AN ANTI-ADRENOMEDULLIN (ADM) ANTIBODY OR AN ANTI-ADM ANTIBODY FRAGMENT TO THE SUBJECT

(71) Applicant: ADRENOMED AG, Hennigsdorf (DE)

(72) Inventor: Andreas Bergmann, Berlin (DE)

(73) Assignee: ADRENOMED AG, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,474

(22) Filed: Feb. 16, 2016

(65) Prior Publication Data

US 2016/0176960 A1 Jun. 23, 2016

Related U.S. Application Data

(63) Continuation of application No. 14/358,334, filed as application No. PCT/EP2012/072930 on Nov. 16, 2012, now abandoned.

(30) Foreign Application Priority Data

Nov. 16, 2011 (EP) .................................. 11189447
Mar. 16, 2012 (EP) .................................. 12160014

(51) Int. Cl.
| | |
|---|---|
| A61K 39/395 | (2006.01) |
| C07K 16/26 | (2006.01) |
| G01N 33/68 | (2006.01) |
| A61K 31/137 | (2006.01) |
| A61K 38/22 | (2006.01) |
| A61K 39/00 | (2006.01) |
| A61K 45/06 | (2006.01) |

(52) U.S. Cl.
CPC ............ *C07K 16/26* (2013.01); *A61K 31/137* (2013.01); *A61K 38/22* (2013.01); *A61K 39/0005* (2013.01); *A61K 45/06* (2013.01); *G01N 33/6893* (2013.01); *A61K 2039/505* (2013.01); *C07K 2317/21* (2013.01); *C07K 2317/24* (2013.01); *C07K 2317/34* (2013.01); *C07K 2317/51* (2013.01); *C07K 2317/515* (2013.01); *C07K 2317/54* (2013.01); *C07K 2317/55* (2013.01); *C07K 2317/56* (2013.01); *C07K 2317/622* (2013.01); *C07K 2317/76* (2013.01); *C07K 2317/92* (2013.01); *C07K 2317/94* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 5,427,908 A | 6/1995 | Dower et al. |
| 5,580,717 A | 12/1996 | Dower et al. |
| 5,585,089 A | 12/1996 | Queen et al. |
| 5,639,855 A | 6/1997 | Kitamura et al. |
| 5,807,715 A | 9/1998 | Morrison et al. |
| 5,830,703 A | 11/1998 | Kitamura et al. |
| 5,837,823 A | 11/1998 | Kitamura et al. |
| 5,910,416 A | 6/1999 | Kitamura et al. |
| 5,939,598 A | 8/1999 | Kucherlapati et al. |
| 5,969,108 A | 10/1999 | McCafferty et al. |
| 6,114,598 A | 9/2000 | Kucherlapati et al. |
| 6,197,069 B1 | 3/2001 | Poste et al. |
| 6,756,483 B1 | 6/2004 | Bergmann et al. |
| 6,818,418 B1 | 11/2004 | Lipovsek et al. |
| 6,864,237 B2 | 3/2005 | Wang |
| 6,884,781 B2 | 4/2005 | Wang et al. |
| 7,064,107 B2 | 6/2006 | Ladner et al. |
| 7,361,473 B2 | 4/2008 | Valkirs et al. |

(Continued)

FOREIGN PATENT DOCUMENTS

| | | |
|---|---|---|
| EP | 0353971 A2 | 2/1990 |
| EP | 0622458 A2 | 11/1994 |

(Continued)

OTHER PUBLICATIONS

Rousseaux, J. et al: 'Optimal condition for the preparation of Fab and F(ab')2 fragments from monoclonal IgG of different rat IgG subclasses' J Immunol Meth vol. 64, 1983, pp. 141-146.

(Continued)

*Primary Examiner* — Christine J Saoud
(74) *Attorney, Agent, or Firm* — Millen White Zelano and Branigan, PC; John Sopp

(57) ABSTRACT

Subject matter of the present invention is an anti-adrenomedullin (ADM) antibody or an anti-adrenomedullin antibody fragment or an anti-ADM non-Ig scaffold for use in therapy of a chronical or acute disease or acute condition of a patient for prevention or reduction of organ dysfunction or organ failure. In a preferred embodiment subject matter of the invention is an anti-ADM antibody or an anti-adrenomedullin antibody fragment or anti-ADM non-Ig scaffold for use in therapy of a chronical or acute disease or acute condition of a patient for prevention or reduction of kidney dysfunction or kidney failure or liver dysfunction or liver failure.

21 Claims, 22 Drawing Sheets
Specification includes a Sequence Listing.

(56) References Cited

U.S. PATENT DOCUMENTS

| | | | |
|---|---|---|---|
| 7,622,272 | B2 | 11/2009 | Cuttitta et al. |
| 7,635,666 | B1 | 12/2009 | McCafferty et al. |
| 7,659,081 | B2 | 2/2010 | Cuttitta et al. |
| 7,723,270 | B1 | 5/2010 | McCafferty et al. |
| 7,811,991 | B2 | 10/2010 | Ladner et al. |
| 7,851,442 | B2 | 12/2010 | Ladner et al. |
| 8,124,586 | B2 | 2/2012 | Ladner et al. |
| 8,278,262 | B2 | 10/2012 | Kolmar et al. |
| 8,710,007 | B2 | 4/2014 | Ladner et al. |
| 8,732,649 | B2 | 5/2014 | Hartl |
| 2002/0055615 | A1 | 5/2002 | Cuttitta et al. |
| 2004/0023334 | A1 | 2/2004 | Prior |
| 2004/0038893 | A1 | 2/2004 | Ladner et al. |
| 2005/0076395 | A1 | 4/2005 | Kucherlapati et al. |
| 2005/0164301 | A1 | 7/2005 | Kolkman et al. |
| 2005/0255548 | A1 | 11/2005 | Lipovsek et al. |
| 2006/0194727 | A1 | 8/2006 | Ladner et al. |
| 2007/0082363 | A1 | 4/2007 | Bougueleret et al. |
| 2007/0212742 | A1 | 9/2007 | Bergmann et al. |
| 2007/0280886 | A1 | 12/2007 | Golz et al. |
| 2008/0200646 | A1 | 2/2008 | Ladner et al. |
| 2008/0064637 | A1 | 3/2008 | Ladner et al. |
| 2008/0076717 | A1 | 3/2008 | Ladner et al. |
| 2008/0131426 | A1 | 6/2008 | Ladner et al. |
| 2008/0152656 | A1 | 6/2008 | Ladner et al. |
| 2008/0260752 | A1 | 10/2008 | Ladner et al. |
| 2009/0082267 | A1 | 3/2009 | Ladner et al. |
| 2009/0130692 | A1 | 5/2009 | Kolmar et al. |
| 2010/0028995 | A1 | 2/2010 | Graversen et al. |
| 2010/0209433 | A1 | 8/2010 | Bergmann et al. |
| 2010/0317540 | A1 | 12/2010 | McCafferty et al. |
| 2011/0086801 | A1 | 4/2011 | Ladner et al. |
| 2011/0207668 | A1 | 8/2011 | Binz et al. |
| 2012/0129710 | A1 | 5/2012 | McCafferty et al. |
| 2013/0005659 | A1 | 1/2013 | Grabulovski et al. |
| 2013/0061104 | A1 | 3/2013 | Hartl |
| 2013/0085113 | A1 | 4/2013 | Hohlbaum et al. |
| 2013/0195874 | A1 | 8/2013 | Bergmann et al. |
| 2013/0195875 | A1 | 8/2013 | Bergmann et al. |
| 2013/0315912 | A1 | 11/2013 | Mabrouk et al. |

FOREIGN PATENT DOCUMENTS

| | | |
|---|---|---|
| EP | 1266025 B1 | 12/2002 |
| EP | 1488209 | 1/2004 |
| EP | 1941867 A1 | 7/2008 |
| EP | 2314308 A1 | 4/2011 |
| EP | 2231860 B1 | 10/2011 |
| WO | 9110741 A1 | 7/1991 |
| WO | 9117271 A1 | 11/1991 |
| WO | 9201203 A1 | 1/1992 |
| WO | 9220791 A1 | 11/1992 |
| WO | 9312227 A1 | 6/1993 |
| WO | 2004/090546 | 10/2004 |
| WO | 2004090546 A1 | 11/2004 |
| WO | 2004097423 A1 | 11/2004 |
| WO | 2005040229 A2 | 5/2005 |
| WO | 2006027147 A2 | 3/2006 |
| WO | 2007062676 A1 | 6/2007 |
| WO | 2010060748 A1 | 6/2010 |
| WO | 2011023685 A1 | 3/2011 |
| WO | 2011107321 A1 | 9/2011 |
| WO | 2011154420 A2 | 12/2011 |

OTHER PUBLICATIONS

Scales and Pilsworth 'The importance of fluid balance in clinical practice' Nursing Standard vol. 22, No. 47, 2008, pp. 50-57.
Schrier; Wang: 'Mechanisms of Disease Acute Renal Failure and Sepsis' The New England Journal of Medicine vol. 351, 2004, pp. 159-169.
Schütte, M.; Thullier, P.; Pelat, T.; Wezler, X.; Rosenstock, P.; Hinz, D.; Kirsch, M.I.; Hasenberg, M.; Frank, R.; Schirrmann, T: 'Identification of a putative Crf splice variant and generation of recombinant antibodies for the specific detection of Aspergillus fumigatus' PLOS ONE vol. 4, 2009, p. E6625.
Alison Shepherd 'Measuring and managing fluid balance' Nursing Times vol. 107, No. 28, pp. 12-16 (2011).
Simkova V et al.: 'The effect of SOD-1 over-expression on hepatic gluconeogenesis and whole-body glucose oxidation during resuscitated, normotensive murine septic shock' Shock vol. 30, 2008, pp. 578-584.
Struck et al., Clin. Chem 55:9—1672-1679 (2009).
Takahashi, K.: 'Adrenomedullin: from a pheochromocytoma to the eyes', 'Peptides', vol. 22, 2001, p. 1691.
Thomas G. M. et al.: 'Cancer cell-derived microparticles bearing P-selectin glycoprotein ligand 1 accelerate thrombus formation in vivo' J. Exp. Med. vol. 206, 2009, pp. 1913-1927.
Tomoda, Y. et al.: 'Regulation of adrenomedullin secretion from cultured cells' Peptides vol. 22, 2001, pp. 1783-1794.
Tsuruda, T. et al.: 'Secretion of proadrenomedullin N-terminal 20 peptide from cultured neonatal rat cardiac cells' Life Sci. vol. 69, No. 2, 2001, pp. 239-245.
Uysal H. et al.: 'Structure and pathogenicity of antibodies specific for citrullinated collagen type II in experimental arthitis' J. Exp. Med. vol. 206, 2009, pp. 449-462.
Wagner F et al_2011_Inflammatory effects of hypothermia and inhaled H2S during resuscitated, hyperdynamic murine septic shock Shock, vol. 35, No. 4, pp. 396Y402, 2011.
Wagner F; Scheuerle A; Weber S; Stahl B; McCook O; KN6FERL MW; Huber-Lang M; Seitz DH; Thomas J; Asfar P: 'Cardiopulmonary, histologic, and inflammatory effects of intravenous Na2S after blunt chest trauma-induced lung contusion in mice' J Trauma vol. 71, No. 6, 2011, pp. 1659-1667.
Ping Wang et al: "The Pivotal role of adrenomedullin in producing hyperdynamic circulation during early stage of sepsis", Archives of Surgery, American Medical Association, Chicago, IL, US, vol. 133, Dec. 1, 1998 (Dec. 1, 1998), pp. 1298-1304, XP002599345, ISSN: 0004-0010.
Wilson, K.M. et al.: 'Rapid whole blood assay for HIV-1 seropositivity using an Fab-peptide conjugate' J Immunol Meth vol. 138, 1991, pp. 111-119.
Wu R et al: "Human vasoactive hormone adrenomedullin and its binding protein rescue experimental animals from shock", Peptides, Elsevier, Amsterdam, NL, vol. 29, No. 7, Jul. 1, 2008 (Jul. 1, 2008), pp. 1223-1230, XP022704824, ISSN: 0196-9781, DOI: 10.1016/J. Peptides.2008.02.021 [retrieved on Mar. 8, 2008].
Albuszies G et al.: 'Effect of increased cardiac output on hepatic and intestinal microcirculatory blood flow, oxygenation, and metabolism in hyperdynamic murine septic shock' Crit Care Med vol. 33, 2005, pp. 2332-2338.
Albuszies G et al.: 'The effect of iNOS deletion on hepatic gluconeogenesis in hyperdynamic murine septic shock' Intensive Care Med vol. 33, 2007, pp. 1094-1101.
Almagro JC; Fransson J.: 'Humanization of antibodies' Front Biosci. vol. 13, Jan. 1, 2008, pp. 1FI19-1FI33.
Barth 2006_Role of inducible nitric oxide synthase in the reduced responsiveness of the myocardium to catecholamines in a hyperdynamic murine model, Crit Care Med. Feb. 2006;34(2):307-13.
Baumgart K et al.: 'Effect of SOD-1 over-expression on myocardial function during resuscitated murine septic shock' Intensive Care Med vol. 35, 2009, pp. 344-349.
Beale, D: 'Molecular fragmentation: Some applications in immunology' Exp Comp Immunol vol. 11, 1987, pp. 287-296.
Bird et al. 'Single-Chain Antigen-Binding Proteins' Science vol. 242, 1988, pp. 423-426.
Chen X. et al.: 'Requirement of open headpiece conformation for activation of leukocyte integrin axp2' PNAS vol. 107, 2010, pp. 14727-14732.
Chintala MS; Bernardino V; Chiu PJS: 'Cyclic GMP but not cyclic AMP prevents renal platelet accumulation following ischemiareperfusion in anesthetized rats' J Pharmacolexpther vol. 271, 1994, pp. 1203-1208.
Chiu PJS: 'Models used to assess renal functions' Drug Develop Res vol. 32, 1994, pp. 247-255.
Chu et al., Neuroscience Letters; 301 (2001), pp. 169-172.

(56) References Cited

OTHER PUBLICATIONS

Coulter, A.; Harris, R. J. Simplified preparation of rabbit Fab fragments, Immunol. Meth. vol. 59, 1983, pp. 199-203.
Ehlenz, K. et al: 'High levels of circulating adrenomedullin in severe illness: Correlation with C-reactive protein and evidence against the adrenal medulla as site of origin' Exp Clin Endocrinol Diabetes vol. 105, 1997, pp. 156-162.
Ellerson, J.R. et al: 'A fragment corresponding to the CH2 region of immunoglobulin G (IgG) with complement fixing activity' FEBS Letters vol. 24, No. 3, 1972, pp. 318-322.
Eto, T.: 'A review of the biological properties and clinical implications of adrenomedullin and proadrenomedullin N-terminal 20 peptide (PAMP), hypotensive and vasodilating peptides' Peptides vol. 22, 2001, pp. 1693-1711.
Gebauer M et al: "Engineered protein scaffolds as next-generation antibody therapeutics", Current Opinion in Chemical Biology, Current Biology Ltd, London, GB, vol. 13, No. 3, Jun. 1, 2009 (Jun. 1, 2009), pp. 245-255, XP026285197, ISSN: 1367-5931, DOI: 10.1016/J.CBPA.2009.04.627 [retrieved on Jun. 6, 2009].
Harris, L; Bajorath, J: 'Profiles for the analysis of immunoglobulin sequences: Comparison of V gene subgroups' Protein Sci. vol. 4, 1995, pp. 306-310.
Hunkapiller; Hood 'The growing Immunoglobulin gene superfamily', Nature vol. 323, 1986, pp. 15-16.
Huston et al. 'Protein engineering of antibody binding sites: Recovery of specific activity in an anti-digoxin single-chain Fv analogue produced in *Escherichia coli*' Proc. Natl. Acad. Sci. U.S.A. vol. 85, 1988, pp. 5879-5883.
Hust, M.; Meyer, T.; Voedisch, B.; Rülker, T.; Thie, H.; El-Ghezal, A.; Kirsch, M.I.; Schütte, M.; Helmsing, S.; Meier, D.: 'A human scFv antibody generation pipeline for proteome research' Journal of Biotechnology vol. 152, 2011, pp. 159-170.
Hyvelin J et al: "Adrenomedullin: A Cardiac Depressant Factor in Septic Shock", Journal of Cardiac Surgery, Futura Publ., Mount Kisco, NY, US, vol. 17, No. 4, Jan. 1, 2002 (Jan. 1, 2002), pp. 328-335, XP007915796, ISSN: 0886-0440 [retrieved on Jul. 12, 2010].
Jacob: 'Acute Renal Failure' Indian J. Anaesth. vol. 47, No. 5, 2003, pp. 367-372.
Jones, P. T.; Dear, P. H.; Foote, J.; Neuberger, M. S.; Winter, G.: 'Replacing the complementarity-determining regions in a human antibody with those from a mouse' Nature vol. 321, 1986, pp. 522-525.
Kaufmann B. et al.: 'Neutralization of West Nile virus by crosslinking of its surface proteins with Fab fragments of the human monoclonal antibody CR4354' PNAS vol. 107, 2010, pp. 18950-18955.
Kerbel, R.S.; Elliot, B.E.: 'Detection ofFc receptors' Meth Enzymol vol. 93, 1983, pp. 113-147.
Kong F. et al.: 'Demonstration of catch bonds between an integrin and its ligand' J. Cell Biol. vol. 185, 2009, pp. 1275-1284.
Wurch Thierry et al: "Novel protein scaffolds as emerging therapeutic proteins: from discovery to clinical proof-of-concept", Trends in Biotechnology, vol. 30, No. 11, Nov. 2012 (Nov. 2012), pp. 575-582, ISSN: 0167-7799.
Kulkarni, P.N. et al.: 'Conjugation of methotrexate to IgG antibodies and their F(ab')2 fragments and the effect of conjugated methotrexate on tumor growth in vivo' Cancer Immunol Immunotherapy vol. 19, 1985, pp. 211-214.
Kuwasako et al_1997_Purification and characterization of PAMP-12 (PAMP-20) in porcine adrenal medulla as a major endogenous biologically active peptide, FEBS Lett. Sep. 1, 1997;414(1)105-10.
Kuwasako, K. et al.: 'Increased plasma proadrenomedullin N-terminal 20 peptide in patients with essential hypertension' Ann. Clin. Biochem. vol. 36, 1999, pp. 622-628.
Lamoyi, E.: 'Preparation of F(ab')2 Fragments from mouse IgG of various subclasses' Meth Enzymol vol. 121, 1986, pp. 652-663.
Lane, R.D.: 'A short-duration polyethylene glycol fusion technique for increasing production of monoclonal antibody-secreting hybridomas' J. Immunol. Meth. vol. 81, 1985, pp. 223-228.

Lanzavecchia et al.'The use of hybrid hybridomas to target human cytotoxic T lymphocytes' Eur. J Immunol. vol. 17, issue 1, 1987, p. 105.
Lindner I. et al.: 'alpha)2-Macroglobulin inhibits the malignant properties of astrocytoma cells by impeding {beta}-catenin signaling' Cancer Res. vol. 70, 2010, pp. 277-287.
Lorenz et al.: 'Functional Antibodies Targeting IsaA of *Staphylococcus aureus* Augment Host Immune Response and Open New Perspectives for Antibacterial Therapy' Antimicrob Agents Chemother. vol. 55, No. 1, Jan. 2011, pp. 165-173.
Mariani, M.: 'A new enzymatic method to obtain high-yield F(ab')2 suitable for clinical use from mouse IgG1' Mol. Immunol. vol. 28, 1991, pp. 69-77.
Martinez et al., Peptides 20 (1999) 1471-1478.
Martinez et al.: 'Mapping of the Adrenomedullin-Binding domains in Human Complement factor H' Hypertens Res vol. 26, 2003, pp. 56-59.
Marx et al.: 'Monoclonal Antibody Production' ATLA vol. 25, 1997, p. 121.
Miller Mae Jean et al: "Adrenomedullin expression in human tumor cell lines: Its potential role as an autocrine growth factor", Journal of Biological Chemistry, American Society for Biochemistry and Molecular Biology, US, vol. 271, No. 38, Sep. 1, 1996 (Sep. 1, 1996), pp. 23345-23351, XP002184272, ISSN: 0021-9258, DOI: 10.1074/JBC.271.38.23345.
Nakamoto M; Shapiro JI; Shanley PF; Chan L; Schrier RW: 'In vitro and in vivo protective effect of atriopeptin III on ischemic acute renal failure' J ClinInvest vol. 80, 1987, pp. 698-705.
Padlan, E. A.: 'A possible procedure for reducing the immunogenicity of antibody variable domains while preserving their ligandbinding properties' Mol. Immunol. vol. 28, 1991, pp. 489-498.
Parham, P. et al.: 'Monoclonal antibodies: purification, fragmentation and application to structural and functional studies of class I MHC antigens' J Immunol Meth vol. 53, 1982, pp. 133-173.
Ping Wang: "Andrenomedullin and cardiovascular responses in sepsis", Peptides, vol. 22, No. 11, Nov. 1, 2001 (Nov. 1, 2001), pp. 1835-1840, XP055022163, ISSN: 0196-9781, DOI: 10.1016/S0196-9781(01)00534-4.
Pio R et al: "Complement Factor H is a Serum-binding Protein for Adrenomedullin, and the Resulting Complex Modulates the Bioactivities of Both Partners", Journal of Biological Chemistry, American Society for Biochemistry and Molecular Biology, US, vol. 276, No. 15, Apr. 1, 2001 (Apr. 1, 2001), pp. 12292-12300, XP009119203, ISSN: 0021-9258, DOI: 10.1074/JBC.M007822200 [retrieved on Dec. 14, 2000].
Pio et al., J. of bio. chem vol. 276, No. 15, Apr. 2001, pp. 12292-12300.
Pio et al_2002_Identification, characterization, and physiological actions of factor H as an Adrenomedullin binding Protein present in Human Plasma : Microscopy Research 57:23-27 (2002).
Quafik et al., "Neutralization of Adrenomedullin Inhibits the Growth of Human Glioblastoma Cell Lines in Vitro and Suppresses Tumor Xenograft Growth in Vivo", American Journal of Pathology, vol. 160, No. 4, 2002, pp. 1279-1292.
Raychaudhuri, G. et al: 'Human IgGl and its Fc fragment bind with different affinities to the Fc receptors on the human U937, HL-60 and ML-1 cell lines' Mol Immunol vol. 22, No. 9, 1985, pp. 1009-1019.
Rousseaux, J. et al.: 'The differential enzyme sensitivity of rat immunoglobulin G subclasses to papain and pepsin' Mol Immunol vol. 17, 1980, pp. 469-482.
Moody, T. W. et al, "Adrenomedullin binds with affinity, elevates cyclic amp, and stimulates c-fos mRNA in C6 Glioma Cells," Peptides, 1997, vol. 18, No. 8, pp. 1111-1115.
Struck, J. et al., "Method for the selective measurement of aminoterminal variants of procalcitonin," Clinical Chemistry, 2009, vol. 55, No. 9, pp. 1672-1679.
Miller, M. J. et al., "Adrenomedullin Expression in Human tumor cell lines," The Journal of Biological Chemistry, Sep. 20, 1996, vol. 271, No. 38, pp. 23345-23351.
Gebauer, M. et al., "Engineered protein scaffolds as next-generation antibody therapeutics," Current Opinion in Chemical Biology, 2009, vol. 13, pp. 245-255.

(56) References Cited

OTHER PUBLICATIONS

Wurch, T. et al., "Novel Protein scaffolds as emerging therapeutic proteins: From discovery to clinical proof-of-concept," Trends in Biotechnology, Nov. 2012, vol. 30, No. 11, pp. 575-582.
Apta-beacon Technical Bulletin, Aptagen, LLC, Sep. 12, 2014.
Noxxon Pharma AG, Technology Section of Website, 2 pages, Sep. 12, 2014.
Meissner et al., "Safety and Phamacokinetics of an Intramuscular Monoclonal Antibody (SB 209763) against Respiratory Syncytial Virus (RSV) in Infants and Young Children at Risk for Severe RSV Disease," Antimicrob Agents Chemother, 1999, vol. 43, pp. 1183.
Breen et al., "Effect of moisture on the stability of a lyophilized humanized monoclonal antibody formulation," Pharm. Res., 2001, vol. 18, pp. 1345-1353.
Degoricija et al., "Survivial Analysis of 314 episodes of sepsis in medicinal intensive care unit in University Hospital: Impact of Intensive Care Unit Performance and Antimicrobial Therapy," Croatian Med. J., 2006, vol. 47, pp. 385-397.
Kaiser et al., 2011 Doc Kaiser's Microbiology Home page, downloaded Dec. 12, 2013.
Benito et al., "Lack of value of midregional pro-adrenomedullin and C-terminal pro-endothelin-1 for prediction of severe bacterial infections in infants with fever without a source," Eur. J. Pediatr., 2013, vol. 172, pp. 1441-1449.
Hyvelin, J.M., Ph.D., et al., "Adrenomedullin: A Cardiac Depressant Factor in Septic Shock," Journal of Cardiac Surgery, Futura Publ., Mount Kisco, NY, vol. 17, No. 4, Jan. 1, 2002, pp. 328-335, XP007915796, ISSN: 0886-0440 [retrieved on Jul. 12, 2010].
Wu, R., et al., "Human Vasoactive Hormone Adrenomedullin and its Binding Protein Rescue Experimental Animals From Shock," Peptides, Elsevier, Amsterdam, NL, vol. 29, No. 7, Jul. 1, 2008, pp. 1223-1230, XP022704824, ISSN: 0196-9781, DOI: 10.1016/J.Peptides.2008.02.021 [retrieved on Mar. 8, 2008].
Pio, R., et al., "Complement Factor H Is a Serum-binding Protein for Adrenomedullin, and the Resulting Complex Modulates the Bioactivities of Both Partners," Jrnl of Biol. Chem., American Society for Biochemistry and Molecular Biology, U.S., vol. 276, No. 15, Apr. 1, 2001, pp. 12292-12300, XP009119203, ISSM: 0021-9258, DOI: 10.1074/JBC.M007822200 [retrieved on Dec. 14, 2000].
Moody, T.W., et al., "Adrenomedullin Binds With High Affinity, Elevates Cyclic AMP, and Stimulates c-fos mRNA in C6 Glioma Cells," Peptides, vol. 18, No. 8, 1997, pp. 1111-1115, ISSN: 0196-9781.
Kitamura, K., et al., "The Intermediate Form of Glycine-Extended Adrenomedullin Is the Major Circulating Molecular Form in Human Plasma," Biochem. Biophys. Res. Commun., vol. 244, No. 2, 1998, pp. 551-555.
Hirata, Y., et al., "Increased Circulating Adrenomedullin, a Novel Vasodilatory Peptide, in Sepsis," Jrnl. of Clin. Endo. Metab., vol. 81, No. 4, 1996, pp. 1449-1453.
Schuetz, P., et al., "Circulating Precursor Levels of Endothelin-1 and Adrenomedullin, Two Endothelium-Derived, Counteracting Substances, in Sepsis," Endothelium, vol. 14, 2007, pp. 345-351.
Nishio, K., M.D., et al., "Increased plasma concentrations of adrenomedullin correlate with relaxation of vascular tone in patients with septic shock," Crit. Care Med., vol. 25, No. 6, 1997, pp. 953-957.
Hinson et al., "Adrenomedullin, a Multifunctional Regulatory Peptide", Endocrine Reviews, vol. 21, No. 2, 2000, pp. 138-167.
Ueda et al., "Increased Plasma Levels of Adrenomedullin in Patients with Systemic Inflammatory Response Syndrome", Am. J. Respir. Crit. Care Med., vol. 160, 1999, pp. 132-136.
http://medical-dictionary.thefreedictionary.com/neutralizing+antibody 2007, downloaded Jun. 17, 2014.
Ping Wang et al. "The Pivotal Role of Adrenomedullin in Producing Hyperdynamic Circulation During the Early Stage of Sepsis" Archives of Surgery, [1998], vol. 133, pp. 1298-1304.
L'Houcine Ouafik et al. "Neutralization of Adrenomedullin Inhibits the Growth of Human Glioblastoma Cell Lines in Vitro and Suppresses Tumor Xenograft Growth in Vivo" American Journal of Pathology, [2002], vol. 160, No. 4, pp. 1279-1292.
A. Martinez et al. "Is Adrenomedullin a Causal Agent in Some Cases of Type 2 Diabetes?" Peptides, [1999], vol. 20, No. 12, pp. 1471-1478.
Ping Wang et al. "Adrenomedullin and cardiovascular responses in sepsis" Peptides, [2001], vol. 22, No. 11, pp. 1835-1840.
Meghan M. Taylor et al. "Adrenomedullin and the Integrative Physiology of Fluid and Electrolyte Balance" Microscopy Research and Technique, [2002], vol. 57, No. 2, pp. 105-109.
Duc Quyen Chu et al. "The calcitonin gene-related peptide (CGRP) antagonist CGRP 8-37 blocks vasodilatation in inflamed rat skin: involvement of adrenomedullin in addition to CGRP" Neuroscience Letter, [2001], vol. 310, No. 2-3, pp. 169-172.
Takashi Kondoh et al. "Pre-treatment of adrenomedullin suppresses cerebral edema caused by transient focal cerebral ischemia in rats detected by magnetic resonance imaging" Brain Research Bulletin [2011], vol. 84, No. 1, pp. 69-74.
Wills K. Samson "Adrenomedullin and the control of fluid and electrolyte homeostasis" Annual Review of Physiology, [1999], vol. 61, No. 1, pp. 363-389.
Wills K. Samson et al. "Adrenomedullin Inhibits Salt Appetite" [1997], vol. 138, No. 2, pp. 613-616.
Meghan M. Taylor et al. "Ribozyme compromise of adrenomedullin mRNA reveals a physiological role in the regulation of water intake" American Journal of Physiology, [2002], vol. 282, No. 6, pp. R1739-R1745.
Wagner, K., et al., "Adrenomedullin blockade improves catecholamine responsiveness and kidney function in resuscitated murine septic shock," Category 1: Sepsis—basic mechanisms—mediators—immunology; Category 2: Sepsis. Poster, 32"d Inter. Symp. on INt. Care and Emerg. Med., Brussels, BE, Mar. 20-23, 2012.
Meeran, K., et al., "Circulating Adrenomedullin Does Not Regulate Systemic Blood Pressure but Increases Plasma Prolactin after Intravenous Infusion in Humans: A Pharmacokinetic Study," Journal of Clinical Endocrinology and Metabolism, vol. 82, No. 1, pp. 95-100, 1997.
Ohta, H., et al., "One-Step Direct Assay for Mature-type Adrenomedullin with Monoclonal Antibodies," Clinical Chemistry, Endocrinology and Metabolism, 45:2, 244-251 (1999).
Webster, N.R., "Monitoring the critically ill patient," Educational Review, J.R. Coli. Surg. Edinb., 44, Dec. 1999, 386-93.
"Care of the Critically Ill Adult," Am. Ac. of Family Physicians, AAFP Reprint No. 291, pp. 1-10, published Jun. 2003.
Hyvelin et al. "Adrenomedullin: a cardiac depressant factor in septic shock." J Card Surg., 1 17(4):328-35, 2002.
Ouafik et al., "Neutralization of adrenomedullin inhibits the growth of human glioblastoma cell lines in vitro and suppresses tumor xenograft growth in vivo," Am J Pathol., 160(4):1279-92, 2002.
Champion et al., "Structure-activity relationships of adrenomedullin in the circulation and adrenal gland," Regul Pept., 30;85(1):1-8, 1999.
Mazzocchi et al., "Adrenomedullin (ADM), acting through ADM(22-52)-sensitive receptors, is involved in the endotoxin-induced hypotension in rats," Life Sci., 3;66(15): 1445-50, 2000.
Wang et al., "The Pivotal Role of Adrenomedullin in Producing Hyperdynamic Circulation During the Early Stage of Sepsis," Arch Surg., 1998;133:1298-1304.
Hasback et al. "CGRP receptors mediating CGRP-, adrenomedullin-andamylin-induced relaxation in porcine coronary arteries. Characterization with 'Compound I' (W098/III28), anon-peptide antagonist." British Journal of Pharmacology, 133, 1405-1413, 2001.
Richards, A.M., et al., "Plasma N-Terminal Pro-Brain Natriuretic Peptide and Adrenomedullin: New Neurohormonal Predictors of Left Ventricular Function and Prognosis After Myocardial Infarction," Circulation-Journal of the American Heart Association, 1998; 97; 1921-1929—Downloaded from circ.ahajournals.org on Jan. 19, 2010.
Qi, Y. F., et al., "Effects of Different Peptide Fragments Derived from Proadrenomedullin on Gene Expression of Adrenomedullin Gene," Peptides 23 (2002) 1141-1147.

FIG 2

SEQ ID NO: 21
YRQSMNNFQGLRSFGCRFGTCTVQKLAHQIYQFTDKDKDNVAPRSKISPQGY-NH₂

SEQ ID NO: 22
YRQSMNQGSRSNGCRFGTCTFQKLAHQIYQLTDKDKDGMAPRNKISPQGY-NH₂

SEQ ID NO: 23
YRQSMNNFQGLRSFGCRFGTC

SEQ ID NO: 24
YRQSMNNFQGLRSFGCRFGTCTVQKLAHQIYQFTDKDKDNVA

SEQ ID NO: 25
PRSKISPQGY-NH2

SEQ ID NO: 26
YRQSMNNFQGLRSF

SEQ ID NO: 27
YRQSMNNFQG

SEQ ID NO: 28
YRQSMN

SEQ ID NO: 29
YRQSMNNFQGLRSFGCRFGTCTVQKLAHQIYQ

SEQ ID NO: 30
YRQSMNQGSRSNGCRFGTCTFQKLAHQIYQLTDKDKDGMA

SEQ ID NO: 31
YRQSMNQGSRSNGCRFGTCTFQKLAHQIYQL hADM-concentration (pg/ml)

FIG. 6

**IGHV1-69*11:**
QVQLVQSGAEVKKPGSSVKVSCKASGGTFSSYAISWVRQAPGQGLEWMGRIIPIL
GTANYAQKFQGRVTITADESTSTAYMELSSLRSEDTAVYYCARYYYYYGMDVW
GQGTTVTVSS
HB3:
QVQLQQSGAELMKPGASVKISCKATGYTFSRYWIEWVKQRPGHGLEWIGEILPGS
GSTNYNEKFKGKATITADTSSNTAYMQLSSLTSEDSAVYYCTEGYEYDGFDYWG
QGTTLTVSS

Alignment (ClustalW2): Identical amino acids are illustrated by stars; points indicate conservative changes.

```
IGHV1:

QVQLVQSGAEVKKPGSSVKVSCKASGGTFSSYAISWVRQAPGQGLEWMGRIIPILGTANYAQKFQ
        GR VTITADESTSTAYMELSSLRSEDTAVYYCARYYYYYGMDVWGQGTTVTVSS

HB3:

QVQLQQSGAELMKPGASVKISCKATGYTFSRYWIEWVKQRPGHGLEWIGEILPGSGSTNYNEKFK
        GK ATITADTSSNTAYMQLSSLTSEDSAVYYCTEGYEYDGFDYWGQGTTLTVSS

**** *****: ***:***:****:* *** * *.**:* **:****:*.*:*  *::**
        :**:*: .***** *:.****:**** ***:*****:. * * *;* *****:****
```

Fluid balance p = 0.001 p = 0.001 p = 0.004 p = 0.027 p = 0.005

METHOD OF MODULATING THE ACTIVITY OF ADRENOMEDULLIN IN A SUBJECT IN NEED OF THERAPEUTIC INTERVENTION FOR ORGAN DYSFUNCTION OR ORGAN FAILURE ASSOCIATED WITH ADRANOMEDULLIN (ADM) ACTIVITY BY ADMINISTERING AN ANTI-ADRENOMEDULLIN (ADM) ANTIBODY OR AN ANTI-ADM ANTIBODY FRAGMENT TO THE SUBJECT

FIELD OF THE INVENTION

Subject matter of the present invention is an anti-adrenomedullin (ADM) antibody or an anti-adrenomedullin antibody fragment or an anti-ADM non-Ig scaffold for use in therapy of a chronical or acute disease or acute condition of a patient for prevention or reduction of organ dysfunction or organ failure.

In a preferred embodiment subject matter of the invention is an anti-ADM antibody or an anti-adrenomedullin antibody fragment or an anti-ADM non-Ig scaffold for use in therapy of a chronical or acute disease or acute condition of a patient for prevention or reduction of kidney dysfunction or kidney failure or for prevention or reduction of liver dysfunction or liver failure.

BACKGROUND

The peptide adrenomedullin (ADM) was described for the first time in 1993 (Kitamura, K., et al., "Adrenomedullin: A Novel Hypotensive Peptide Isolated From Human Pheochromocytoma", Biochemical and Biophysical Research Communications, Vol. 192 (2), pp. 553-560 (1993)) as a novel hypotensive peptide comprising 52 amino acids, which had been isolated from a human pheochromocytome; SEQ ID NO: 21. In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "preproadrenomedullin" (pre-proADM). In the present description, all amino acid positions specified usually relate to the pre-proADM which comprises the 185 amino acids. The peptide adrenomedullin (ADM) is a peptide which comprises 52 amino acids (SEQ ID NO: 21) and which comprises the amino acids 95 to 146 of pre-proADM, from which it is formed by proteolytic cleavage. To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM. The discovery and characterization of ADM in 1993 triggered intensive research activity, the results of which have been summarized in various review articles, in the context of the present description, reference being made in particular to the articles to be found in an issue of "Peptides" devoted to ADM in particular (Editorial, Takahashi, K., "Adrenomedullin: from a pheochromocytoma to the eyes", Peptides, Vol. 22, p. 1691 (2001)) and (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)). A further review is (Hinson, et al., "Adrenomedullin, a Multifunctional Regulatory Peptide", Endocrine Reviews, Vol. 21(2), pp. 138-167 (2000)). In the scientific investigations to date, it has been found, inter alia, that ADM may be regarded as a polyfunctional regulatory peptide. It is released into the circulation in an inactive form extended by glycine (Kitamura, K., et al., "The intermediate form of glycine-extended adrenomedullin is the major circulating molecular form in human plasma", Biochem. Biophys. Res. Commun., Vol. 244(2), pp. 551-555 (1998). Abstract Only). There is also a binding protein (Pio, R., et al., "Complement Factor H is a Serum-binding Protein for adrenomedullin, and the Resulting Complex Modulates the Bioactivities of Both Partners", The Journal of Biological Chemistry, Vol. 276(15), pp. 12292-12300 (2001)) which is specific for ADM and probably likewise modulates the effect of ADM. Those physiological effects of ADM as well as of PAMP which are of primary importance in the investigations to date were the effects influencing blood pressure.

Hence, ADM is an effective vasodilator, and thus it is possible to associate the hypotensive effect with the particular peptide segments in the C-terminal part of ADM. It has furthermore been found that the abovementioned further physiologically active peptide PAMP formed from pre-proADM likewise exhibits a hypotensive effect, even if it appears to have an action mechanism differing from that of ADM (cf. in addition to the abovementioned review articles (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)) and (Hinson, et al., "Adrenomedullin, a Multifunctional Regulatory Peptide", Endocrine Reviews, Vol. 21(2), pp. 138-167 (2000)) also (Kuwasako, K., et al., "Purification and characterization of PAMP-12 (PAMP-20) in porcine adrenal medulla as a major endogenous biologically active peptide", FEBS Lett, Vol. 414(1), pp. 105-110 (1997). Abstract only), (Kuwasaki, K., et al., "Increased plasma proadrenomedullin N-terminal 20 peptide in patients with essential hypertension", Ann. Clin. Biochem., Vol. 36 (Pt. 5), pp. 622-628 (1999). Abstract only) or (Tsuruda, T., et al., "Secretion of proadrenomedullin N-terminal 20 peptide from cultured neonatal rat cardiac cells", Life Sci., Vol. 69(2), pp. 239-245 (2001). Abstract only) and EP-A2 0 622 458). It has furthermore been found that the concentrations of ADM which can be measured in the circulation and other biological liquids are, in a number of pathological states, significantly above the concentrations to be found in healthy control persons. Thus, the ADM level in patients with congestive heart failure, myocardial infarction, kidney diseases, hypertensive disorders, Diabetes mellitus, in the acute phase of shock and in sepsis and septic shock are significantly increased, although to different extents. The PAMP concentrations are also increased in some of said pathological states, but the plasma levels are lower relative to ADM ((Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)); page 1702). It is furthermore known that unusually high concentrations of ADM are to be observed in sepsis, and the highest concentrations in septic shock (cf. (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)) and (Hirata, et al., "Increased Circulating Adrenomedullin, a Novel Vasodilatory Peptide, in Sepsis", Journal of Clinical Endocrinology and Metabolism, Vol. 81(4), pp. 1449-1453 (1996)), (Ehlenz, K., et al., "High levels of circulating adrenomedullin in severe illness: Correlation with C-reactive protein and evidence against the adrenal medulla as site of origin", Exp Clin Endocrinol Diabetes, Vol. 105, pp. 156-162 (1997)), (Tomoda, Y., et al., "Regulation of adrenomedullin secretion from cultured cells", Peptides, Vol. 22, pp. 1783-1794 (2001)), (Ueda, S., et al., "Increased Plasma Levels of Adrenomedullin in Patients with Systemic Inflammatory Response Syndrome", Am. J. Respir. Crit. Care Med., Vol. 160, pp. 132-136 (1999)) and (Wang, P., "Adrenomedullin and cardiovascular responses in sepsis", Peptides, Vol. 22, pp. 1835-1840 (2001))).

Known in the art is further a method for identifying adrenomedullin immunoreactivity in biological liquids for diagnostic purposes and, in particular within the scope of sepsis diagnosis, cardiac diagnosis and cancer diagnosis. According to the invention, the midregional partial peptide of the proadrenomedullin, which contains amino acids (45-92) of the entire preproadrenomedullin, is measured, in particular, with an immunoassay which works with at least one labeled antibody that specifically recognizes a sequence of the mid-proADM. (WO2004/090546).

WO-A1 2004/097423 describes the use of an antibody against adrenomedullin for diagnosis, prognosis, and treatment of cardiovascular disorders. Treatment of diseases by blocking the ADM receptor are also described in the art, (e.g. WO-A1 2006/027147, PCT/EP2005/012844) said diseases may be sepsis, septic shock, cardiovascular diseases, infections, dermatological diseases, endocrinological diseases, metabolic diseases, gastroenterological diseases, cancer, inflammation, hematological diseases, respiratory diseases, muscle skeleton diseases, neurological diseases, urological diseases.

It is reported for the early phase of sepsis that ADM improves heart function and the blood supply in liver, spleen, kidney and small intestine. ADM-neutralizing antibodies neutralize the before mentioned effects during the early phase of sepsis (Wang, P., "Adrenomedullin and cardiovascular responses in sepsis", Peptides, Vol. 22, pp. 1835-1840 (2001).

In the later phase of sepsis, the hypodynamical phase of sepsis, ADM constitutes a risk factor that is strongly associated with the mortality of patients in septic shock. (Schütz et al., "Circulating Precursor levels of endothelin-1 and adrenomedullin, two endothelium-derived, counteracting substances, in sepsis", Endothelium, 14:345-351, (2007)). Methods for the diagnosis and treatment of critically ill patients, e.g. in the very late phases of sepsis, and the use of endothelin and endothelin agonists with vasoconstrictor activity for the preparation of medicaments for the treatment of critically ill patients have been described in WO-A1 2007/062676. It is further described in WO-A1 2007/062676 to use, in place of endothelin and/or endothelin agonists, or in combination therewith, adrenomedullin antagonists, i.e. molecules which prevent or attenuate the vasodilating action of adrenomedulin, e.g. by blocking its relevant receptors, or substances preventing the binding of adrenomedullin to its receptor (e.g. specific binders as e.g. antibodies binding to adrenomedullin and blocking its receptor bindings sites; "immunological neutralization"). Such use, or combined use, including a subsequent or preceding separate use, has been described in certain cases to be desirable for example to improve the therapeutic success, or to avoid undesirable physiological stress or side effects. Thus, it is reported that neutralizing ADM antibodies may be used for the treatment of sepsis in the late stage of sepsis.

Administration of ADM in combination with ADM-binding-Protein-1 is described for treatment of sepsis and septic shock in the art. It is assumed that treatment of septic animals with ADM and ADM-binding-Protein-1 prevents transition to the late phase of sepsis. It has to be noted that in a living organism ADM binding protein (complement factor H) is present in the circulation of said organism in high concentrations (Pio et al.: Identification, characterization, and physiological actions of complement factor H as an Adrenomedullin binding Protein present in Human Plasma; Microscopy Res. and Technique, 55:23-27 (2002) and Martinez et al.; Mapping of the Adrenomedullin-Binding domains in Human Complement factor H; Hypertens Res Vol. 26, Suppl (2003), S56-59).

In accordance with the invention the ADM-binding-Protein-1 may be also referred to as ADM-binding-Protein-1 (complement factor H).

Prevention or reduction of organ dysfunction or organ failure is very important when treating a patient having a chronic or acute disease or acute condition, especially a life threatening disease or condition.

BRIEF DESCRIPTION OF THE DRAWINGS

FIG. 2—
hADM 1-52 (SEQ ID NO: 21)
mADM 1-50 (SEQ ID NO: 22)
aa 1-21 of human ADM (SEQ ID NO: 23)
aa 1-42 of human ADM (SEQ ID NO: 24)
aa 43-52 of human ADM (SEQ ID NO: 25)
aa 1-14 of human ADM (SEQ ID NO: 26)
aa 1-10 of human ADM (SEQ ID NO: 27)
aa 1-6 of human ADM (SEQ ID NO: 28)
aa 1-32 of human mature human ADM (SEQ ID NO: 29)
aa 1-40 of mature murine ADM (SEQ ID NO: 30)
aa 1-31 of mature murine ADM (SEQ ID NO: 31)
FIG. 3A—Dose response curve of human ADM. Maximal cAMP stimulation was adjusted to 100% activation.

FIG. 6—Alignment of the Fab with homologous human framework sequences.

DESCRIPTION OF THE INVENTION

Figure 1A:
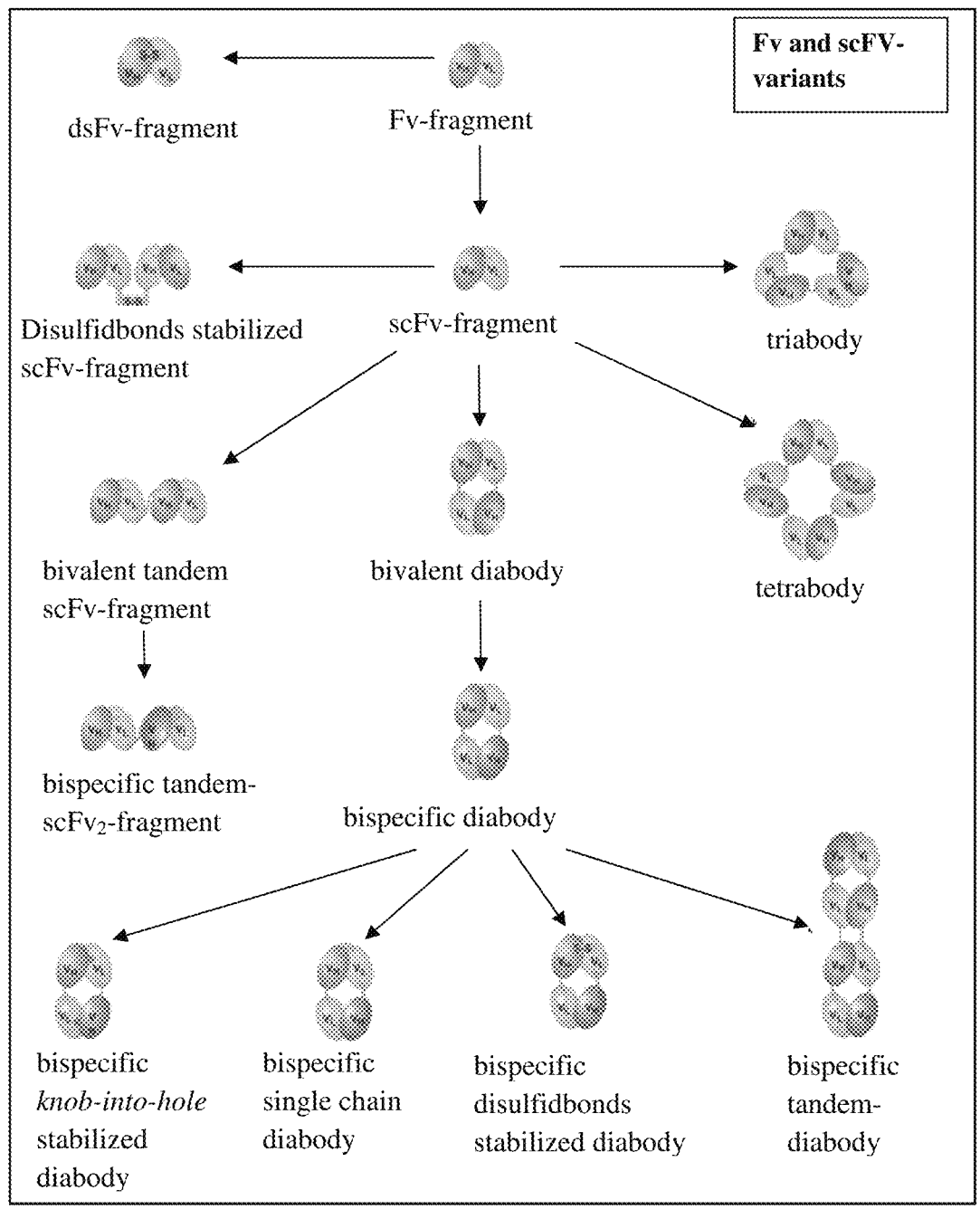
FIG. 1A—Illustration of antibody formats—Fv and scFv-Variants.

Subject matter of the present invention is an anti-adrenomedullin (ADM) antibody or an anti-adrenomedullin antibody fragment or anti-ADM non-Ig scaffold for use in therapy of a chronic or acute disease or acute condition of a patient for prevention or reduction of organ dysfunction or organ failure. In a preferred embodiment subject matter of the invention is an anti-ADM antibody or an anti-adrenomedullin antibody fragment or anti-ADM non-Ig scaffold for use in therapy of a chronic or acute disease or acute condition of a patient for prevention or reduction of kidney dysfunction or kidney failure or liver dysfunction or liver failure. Said organ may be selected from the group comprising heart, kidney, liver, lungs, pancreas, small intestines and spleen. Anti-ADM antibody or an anti-adrenomedullin antibody fragment or anti-ADM non-Ig scaffold may be administered at any point of time before the occurrence of dysfunction or failure or after the occurrence of dysfunction or failure.

"Organ dysfunction" denotes a condition or a state of health where an organ does not perform its expected function. "Organ failure" denotes an organ dysfunction to such a degree that normal homeostasis cannot be maintained without external clinical intervention.

By contrast, organ function represents the expected function of the respective organ within physiologic ranges. The person skilled in the art is aware of the respective function of an organ during medical examination. Therefore, in the following only basic information in regard to particular organs within the scope of the invention is provided:

The heart is a chambered muscular organ that pumps blood received from the veins into the arteries. Thereby the heart is maintaining the flow of blood through the circulatory system entirely to supply oxygen to the body.

The kidneys is a pair of organs that function to maintain adequate water and electrolyte balance, they regulate acid-base concentration, and further filter the blood of metabolic wastes, which are afterwards excreted as urine.

The liver is a large organ that secretes bile and is active in the formation of certain blood proteins and in the metabolism of carbohydrates, fats, and proteins.

The lungs are functioning to remove carbon dioxide from the blood and provide it with oxygen.

The pancreas secretes pancreatic juice into the duodenum and insulin, glucagon, and somatostatin into the bloodstream.

The small intestines are the part of the digestive tract, in which the process of digestion is practically completed. It is narrow and contorted, and consists of three parts, the duodenum, jejunum, and ileum.

The spleen plays important roles in regard to erythrocytes—the red blood cells—and the immune system. Specifically, the spleen removes old red blood cells and holds a reserve of blood in case of hemorrhagic shock while also recycling iron. Further, it metabolizes hemoglobin removed from senescent erythrocytes. The globin portion of hemoglobin is degraded to its constitutive amino acids, and the heme portion is metabolized to bilirubin, which is subsequently shuttled to the liver for its removal. In addition, the spleen synthesizes antibodies in its white pulp and removes antibody-coated bacteria along with antibody-coated blood cells by way of blood and lymph node circulation.

It should be emphasized that the provided anti-adrenomedullin (ADM) antibody or an anti-adrenomedullin antibody fragment or anti-ADM non-Ig scaffold are intended by the present invention to be applied for sake of prevention or reduction of organ dysfunction and organ failure, and thus are not necessarily intended for any methods of primary treatment or first line treatment to the chronic or acute disease or acute condition itself, which therefore can be termed as underlying disease(s). This means the present invention does not provide for a therapy of healing/curing e.g. infections, cancer, or tumors located in the respective organ, but for resuscitating the respective organ towards physiologic function. Accordingly, the therapy for a chronic or acute disease or acute condition of a patient within the scope of the invention is related to any kind of organ insufficiency, or poor organ function as an acute event.

Specifically according to the invention it has to be understood that in case of any organ dysfunction or organ failure of pancreas that is e.g. due to diabetes mellitus, the herein provided anti-ADM antibody, anti-ADM antibody fragment, or anti-ADM non-Ig scaffold are not intended for first line treatment of diabetes, but for resuscitating pancreas' physiologic function.

Specifically according to the invention it has to be understood that in case of any organ dysfunction or organ failure of e.g. pancreas, lung, liver, kidney, spleen, small intestine, heart that is due to cancerous tumors or cancer, the herein provided anti-ADM antibody, anti-ADM antibody fragment, or anti-ADM non-Ig scaffold are not intended for first line treatment of cancerous tumors or cancer in the respective organ, but for resuscitating the respective organ's physiologic function.

The patient group(s) addressed by the instant invention can be defined as set out below.

In the following, clinical criteria are mentioned for respective organs that are prone to dysfunction or failure, and thus represent the patient group(s) of having a chronic or acute disease or acute condition in accordance with the invention:

The criteria orientate on the clinical SOFA score.

The SOFA system was created in a consensus meeting of the European Society of Intensive Care Medicine in 1994 and further revised in 1996.

The SOFA is a six-organ dysfunction/failure score measuring multiple organ failure daily. Each organ is graded from 0 (normal) to 4 (the most abnormal), providing a daily score of 0 to 24 points. The objective of the SOFA is to create a simple, reliable, and continuous score for clinical staff.

Sequential assessment of organ dysfunction during the first few days of intensive care unit (ICU) or hospital admission is a good indicator of prognosis. Both the mean and highest SOFA scores are particularly useful predictors of outcome.

| SOFA score | 0 | 1 | 2 | 3 | 4 |
|---|---|---|---|---|---|
| Respiration | | | | | |
| $PaO_2/FIO_2$ (mm Hg) $SaO_2/FIO_2$ | >400 | <400 221-301 | <300 142-220 | <200 67-141 | <100 <67 |
| Coagulation | | | | | |
| Platelets $10^3/mm^3$ | >150 | <150 | <100 | <50 | <20 |
| Liver | | | | | |
| Bilirubin (mg/dL) | <1.2 | 1.2-1.9 | 2.0-5.9 | 6.0-11.9 | >12.0 |
| Cardiovascular[b] | | | | | |
| Hypotension | No hypotension | MAP <70 | Dopamine </=5 or dobutamine (any) | Dopamine >5 or norepinephrine </=0.1 | Dopamine >15 or norepinephrine >0.1 |
| CNS | | | | | |
| Glasgow Coma Score | 15 | 13-14 | 10-12 | 6-9 | <6 |
| Renal | | | | | |
| Creatinine (mg/dL) or urine output mL/d | <1.2 | 1.2-1.9 | 2.0-3.4 | 3.5-4.9 or <500 | >5.0 or <200 |

MAP, mean arterial pressure; CNS, central nervous system; $SaO_2$, peripheral arterial oxygen saturation.
[a] $PaO_2/FIO_2$ ratio was used preferentially. If not available, the $SaO_2/FIO_2$ ratio was used;
[b] vasoactive mediations administered for at least 1 hr (dopamine and norepinephrine µg/kg/min).

REFERENCES FOR SOFA SCORE

1. Jones A E, Trzeciak S, Kline J A. The Sequential Organ Failure Assessment score for predicting outcome in patients with severe sepsis and evidence of hypoperfusion at the time of emergency department presentation. Crit Care Med. 2009 May; 37(5):1649-54.
2. Ferreira F L, Bota D P, Bross A, Mélot C, Vincent J L. Serial evaluation of the SOFA score to predict outcome in critically ill patients. JAMA. 2001 Oct. 10; 286(14):1754-8.
3. Vincent J L, Moreno R, Takala J, Willatts S, De Mendonça A, Bruining H, Reinhart C K, Suter P M, Thijs L G. The SOFA (Sepsis-related Organ Failure Assessment) score to describe organ dysfunction/failure. On behalf of the Working Group on Sepsis-Related Problems of the European Society of Intensive Care Medicine. Intensive Care Med. 1996 July; 22(7):707-10.

In a specific embodiment the patient group pursuant to the invention is having as lower threshold at least one SOFA score, being it 1 for one the clinical criteria respiration, or liver, or coagulation, or cardiovascular, or CNS, or renal on day of admission to hospital or Intensive Care Unit (ICU). Thus, said patient group is in need of therapeutic intervention pursuant to the invention, and thus in need for prevention or reduction of organ dysfunction or organ failure In another specific embodiment the patient group pursuant to the invention is having as lower threshold at least two SOFA scores, being it 1 each for the clinical criteria respiration, and/or liver, and/or coagulation, and/or cardiovascular, and/or CNS, and/or renal on day of admission to hospital or Intensive Care Unit (ICU). Thus, said patient group is in need of therapeutic intervention pursuant to the invention, and thus in need for prevention or reduction of organ dysfunction or organ failure.

In another specific embodiment the patient group pursuant to the invention is having as lower threshold at least three SOFA scores, being it 1 each for the clinical criteria respiration, and/or liver, and/or coagulation, and/or cardiovascular, and/or CNS, and/or renal on day of admission to hospital or Intensive Care Unit (ICU). Thus, said patient group is in need of therapeutic intervention pursuant to the invention, and thus in need for prevention or reduction of organ dysfunction or organ failure.

In another specific embodiment the patient group pursuant to the invention is having as lower threshold at least four SOFA scores, being it 1 each for the clinical criteria respiration, and/or liver, and/or coagulation, and/or cardiovascular, and/or CNS, and/or renal on day of admission to hospital or Intensive Care Unit (ICU). Thus, said patient group is in need of therapeutic intervention pursuant to the invention, and thus in need for prevention or reduction of organ dysfunction or organ failure.

In another specific embodiment the patient group in need for prevention or reduction of renal organ dysfunction or renal organ failure pursuant to the invention is having a renal SOFA score of at least 1, or of 2, or of 3, or of 4.

In another specific embodiment the patient group in need for prevention or reduction of liver organ dysfunction or liver organ failure pursuant to the invention is having a liver SOFA score of at least 1, or of 2, or of 3, or of 4.

In another specific embodiment the patient group in need for prevention or reduction of heart organ dysfunction or heart organ failure pursuant to the invention is having a cardiovascular SOFA score of at least 1, or of 2, or of 3, or of 4.

In another specific embodiment the patient group in need for prevention or reduction of lung organ dysfunction or lung organ failure pursuant to the invention is having a respiratory SOFA score of at least 1, or of 2, or of 3, or of 4.

Independent of the initial score, generally an increase in SOFA score during the first 48 hours in the ICU or in the hospital predicts a mortality rate of at least 50%.

Thus, in another specific embodiment the patient group in need of therapeutic intervention for organ dysfunction/failure in accordance with invention is characterized by having at least one SOFA score increased within the initial 48 hours after admission to hospital or ICU.

Patient Group—Kidney Dysfunction/Failure

In the following, said clinical criteria denote the patient group(s) for kidney dysfunction/failure:
  Patients at risk for kidney dysfunction/failure: GFR decrease >25%, serum creatinine increased 1.5 times or urine production of <0.5 ml/kg/hr for 6 hours
  Patients with present kidney injury: GFR decrease >50%, doubling of creatinine or urine production<0.5 ml/kg/hr for 12 hours
  Patients with kidney failure: GFR decrease >75%, tripling of creatinine or creatinine>355 µmol/l (with a rise of >44) (>4 mg/dl) or urine output below 0.3 ml/kg/hr for 24 hours
  Patients with loss of kidney function: persistent acute kidney injury (AKI) or complete loss of kidney function for more than 4 weeks
  end-stage renal disease: complete loss of kidney function for more than 3 months.
Patient Group—Liver Dysfunction/Failure The patient group for liver dysfunction/failure is characterized by a lower threshold of Bilirubin of >1.2 mg/dL, preferably >1.9 mg/dL, more preferably >5.9 mg/dL.

Oxygen Depletion

The person skilled in the art is aware that sepsis is associated with mitochondrial dysfunction, which inevitably leads to impaired oxygen consumption and ultimately to sepsis-induced multiple organ failure.

This holds especially true for raised tissue oxygen tensions in septic patients, suggesting reduced ability of the organs to use oxygen. Because ATP production by mitochondrial oxidative phosphorylation accounts for more than 90% of total oxygen consumption mitochondrial dysfunction may directly results in organ failure, possibly due to nitric oxide, which is known to inhibit mitochondrial respiration in vitro and is produced in excess in sepsis.

Therefore, in a very specific embodiment of the invention the anti-ADM antibody or the anti-ADM antibody fragment or anti-ADM non-Ig scaffold are particularly intended to be used in methods of prevention for organ dysfunction and failure in SIRS, sepsis, severe sepsis, shock and septic shock patients.

Oxygene depletion may be also caused by ischemic events as e.g. by pass surgery.

The anti-ADM antibody or the anti-ADM antibody fragment or anti-ADM non-Ig scaffold may be also administered preventively before the patient exhibits any signs of dysfunction or failure of an organ. This might be the case if the patient has a chronic or acute disease or acute condition where dysfunction or failure problems may be expected, e.g. comprising severe infections as e.g. meningitis, Systemic inflammatory Response-Syndrome (SIRS) sepsis; other diseases as diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata, poisoning. The anti-ADM antibody or the anti-ADM antibody fragment or anti-ADM non-Ig scaffold may be also administered preventively or therapeutically before, or during or after chemotherapy. The same applies for surgeries where ischemic damages may occur to certain organs which may result in dysfunction or failure of an organ. Preventively means before an organ damage occurs and therapeutically means that an organ damage has been already occurred. Especially useful is the antibody or fragment or scaffold according to the present invention for reducing the risk of organ dysfunction or failure during sepsis and septic shock, i.e. late phases of sepsis.

Acute disease or acute conditions may be selected from the group but are not limited to the group comprising severe infections as e.g. meningitis, Systemic inflammatory Response-Syndrome (SIRS), or sepsis; other diseases as diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata, poisoning, damages induced by chemotherapy.

Especially useful is the antibody or fragment or scaffold according to the present invention for reducing the risk of mortality during sepsis and septic shock, i.e. late phases of sepsis.

In the following clinical criteria for SIRS, sepsis, severe sepsis, septic shock will be defined.

1) Systemic inflammatory host response (SIRS) characterized by at least two of the following symptoms
  patients exhibit hypotension (mean arterial pressure is <65 mm Hg)
  elevated serum lactate level being >4 mmol/L
  blood glucose>7.7 mmol/L (in absence of diabetes)
  central venous pressure is not within the range 8-12 mm Hg
  urine output is <0.5 mL×kg$^{-1}$×hr$^{-1}$
  central venous (superior vena cava) oxygen saturation is <70% or mixed venous<65%
  heart rate is >90 beats/min
  temperature<36° C. or >38° C.
  respiratory rate>20/min
  white cell count<4 or >12×10$^9$/L (leucocytes); >10% immature neutrophils 2) Sepsis
Following at least two of the symptoms mentioned under 1), and additionally a clinical suspicion of new infection, being:
  cough/sputum/chest pain
  abdominal pain/distension/diarrhoea
  line infection
  endocarditis
  dysuria
  headache with neck stiffness
  cellulitis/wound/joint infection
  positive microbiology for any infection 3) Severe sepsis
Provided that sepsis is manifested in patient, and additionally a clinical suspicion of any organ dysfunction, being:
  blood pressure systolic<90/mean; <65 mmHG
  lactate>2 mmol/L
  Bilirubine>34 µmol/L
  urine output<0.5 mL/kg/h for 2 h
  creatinine>177 µmol/L
  platelets<100×10$^9$/L
  SpO$_2$>90% unless O$_2$ given 4) Septic shock
At least one sign of end-organ dysfunction as mentioned under 3) is manifested. Septic shock is indicated, if there is refractory hypotension that does not respond to treatment and intravenous systemic fluid administration alone is insufficient to maintain a patient's blood pressure from becoming hypotensive also provides for an administration of an anti-ADM antibody or an anti-ADM antibody fragment or an anti-ADM non-Ig scaffold in accordance with the present invention.

Thus, acute disease or acute conditions may be selected from the group but are not limited to the group comprising severe infections as e.g. meningitis, Systemic inflammatory Response-Syndrome (SIRS), or sepsis; other diseases as diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata, poisoning, damages induced by chemotherapy. Especially useful is the antibody or fragment or scaffold according to the present invention for reducing the risk of mortality during sepsis and septic shock, i.e. late phases of sepsis.

In one embodiment of the present invention the patient is not suffering from SIRS, a severe infection, sepsis, shock as e.g. septic shock. Said severe infection denotes e.g. meningitis, Systemic inflammatory Response-Syndrome (SIRS), sepsis, severe sepsis, and shock as e.g. septic shock. In this regard, a severe sepsis is characterized in that sepsis is manifested in said patient, and additionally a clinical suspicion of any organ dysfunction is present, being it:
  blood pressure systolic<90/mean; <65 mmHG
  lactate>2 mmol/L
  Bilirubine>34 µmol/L
  urine output<0.5 mL/kg/h for 2 h
  creatinine>177 µmol/L
  platelets<100×10$^9$/L
  SpO$_2$>90% unless O$_2$ given In another specific embodiment said acute disease or acute condition is not sepsis, severe sepsis or is not SIRS or is not shock, or septic shock.

In another embodiment said acute disease or acute condition is not sepsis.

In another embodiment said acute disease or acute condition is selected from the group comprising meningitis, diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata, poisoning, damages induced by chemotherapy.

It should be emphasized that the herein provided anti-ADM antibody, anti-ADM antibody fragment or anti-ADM non-Ig scaffold is not intended for first line treatment of any organ associated diseases such as nephroliths, renal cancer, nephritis, liver cirrhosis, fatty liver, hepatic cancer, or e.g. hepatitis. The anti-ADM antibody or an anti-ADM antibody fragment or an anti-ADM non-Ig scaffold in accordance with the invention are intended to prevent from or address a malfunction in the respective organ's physiologic function.

The organ protecting effect of the anti-ADM antibody or the anti-ADM antibody fragment or anti-ADM non-Ig scaffold is thus supporting the primary therapy of said chronic or acute disease or acute condition. In case of a chronic or acute disease or acute condition like a severe infection, SIRS, sepsis or the like the primary therapy would be e.g. the administration of antibiotics. The anti-ADM antibody or the anti-ADM antibody fragment or anti-ADM non-Ig scaffold would protect the organ and would help to prevent worsening of the critical condition of said patient until the e.g. antibiotic administration takes effect. As before mentioned the anti-ADM antibody or the anti-ADM antibody fragment or anti-ADM non-Ig scaffold may be administered in a preventive way or in a therapeutic way, this means in order to prevent dysfunction or failure problems or in order to reduce organ dysfunction when dysfunction problems are present in a said patient.

In another specific embodiment of the invention the expression "the anti-ADM antibody or the anti-ADM antibody fragment or anti-ADM non-Ig scaffold may be administered in a preventive way or in a therapeutic way" denotes systemic administration to a patient.

In one embodiment of the invention an Anti-adrenomedullin (ADM) antibody or an anti-ADM antibody fragment or anti-ADM non-Ig scaffold is to be used in combination with vasopressors e.g. catecholamine wherein said combination is for use in therapy of a chronic or acute disease or acute condition of a patient for protecting an organ of said patient.

Subject matter of the invention in one specific embodiment is, thus, an anti-ADM (ADM) antibody or an anti- ADM antibody fragment or anti-ADM non-Ig scaffold for use in therapy of a patient in need of an administration of vasopressors e.g. of catecholamine administration.

Furthermore, in one embodiment of the invention an anti-adrenomedullin (ADM) antibody or an anti-adrenomedullin antibody fragment or an anti-ADM non-Ig scaffold is to be used in combination with fluids administered intravenously, wherein said combination is for use in therapy of a patient having a chronic or acute disease or acute condition of a patient for protecting the organs of said patient. It should be emphasized that said fluids to be administered intravenously are administered systemically.

In one embodiment of the invention said patient having a chronic or acute disease or condition being in need for protecting its organs is characterized by the need of said patient to get intravenous fluids.

It should be noted that in accordance with the invention administration of fluids is in the meaning of systemic administration of fluids.

Subject matter of the invention in one specific embodiment is, thus, an anti-adrenomedullin (ADM) antibody or an anti-adrenomedullin antibody fragment or anti-ADM non-Ig scaffold for use in therapy of a patient in need of intravenous fluids. Even with restoration of adequate blood pressure and normal or supranormal cardiac output, signs of tissue hypoperfusion may persist. This is often called "distributive shock" and may be related to maldistribution and blood flow at the regional or microvascular level and/or a cellular inability to utilize oxygen despite adequate oxygen delivery. It is clinically important that tissue hypoperfusion be recognized, despite what may appear to be "normal" blood pressures, and should trigger timely intervention. According to the present invention such an intervention is the administration of an anti-adrenomedullin (ADM) antibody or an anti-adrenomedullin antibody fragment or anti-ADM non-Ig scaffold for use in therapy of a chronic or acute disease or acute condition of a patient for prevention or reduction of organ dysfunction.

An antibody according to the present invention is a protein including one or more polypeptides substantially encoded by immunoglobulin genes that specifically binds an antigen. The recognized immunoglobulin genes include the kappa, lambda, alpha (IgA), gamma (IgG$_1$, IgG$_2$, IgG$_3$, IgG$_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.*, 85:5879-5883, 1988; Bird et al., Science 242:423-426, 1988; Hood et al., *Immunology*, Benjamin, N.Y., 2nd ed., 1984; Hunkapiller and Hood, *Nature* 323:15-16, 1986). An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741).

Thus, the anti-ADM antibody or an anti-adrenomedullin antibody fragment may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')$_2$-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

Furthermore, in one embodiment of the invention an anti-Adrenomedullin (ADM) antibody or an anti-adrenomedullin antibody fragment or an anti-ADM non-Ig scaffold is mono specific.

Mono specific anti-Adrenomedullin (ADM) antibody or mono specific anti-adrenomedullin antibody fragment or monospecific anti-ADM non-Ig scaffold means that said antibody or antibody fragment or non-Ig scaffold binds to one specific region encompassing at least 5 amino acids within the target ADM.

Mono specific anti-Adrenomedullin (ADM) antibody or mono specific anti-adrenomedullin antibody fragment or monospecific anti-ADM non-Ig scaffold are anti-Adrenomedullin (ADM) antibodies or anti-adrenomedullin antibody fragments or anti-ADM non-Ig scaffolds that all have affinity for the same antigen.

In another preferred embodiment of the invention an anti-Adrenomedullin (ADM) antibody or an anti-adrenomedullin antibody fragment or an anti-ADM non-Ig scaffold is monospecific.

Mono specific anti-Adrenomedullin (ADM) antibody or mono specific anti-adrenomedullin antibody fragment or monospecific anti-ADM non-Ig scaffold means that said antibody or antibody fragment or non-Ig scaffold binds to one specific region encompassing at least 4 amino acids within the target ADM.

In another special embodiment the anti-ADM antibody or the antibody fragment binding to ADM is a monospecific antibody. Monospecific means that said antibody or antibody fragment binds to one specific region encompassing at least 5 amino acids within the target ADM.

In another special and preferred embodiment the anti-ADM antibody or the antibody fragment binding to ADM is a monospecific antibody. Monospecific means that said antibody or antibody fragment binds to one specific region encompassing at least 4 amino acids within the target ADM.

Monospecific antibodies or fragments are antibodies or fragments that all have affinity for the same antigen. Monoclonal antibodies are monospecific, but monospecific antibodies may also be produced by other means than producing them from a common germ cell.

Figure 1B:
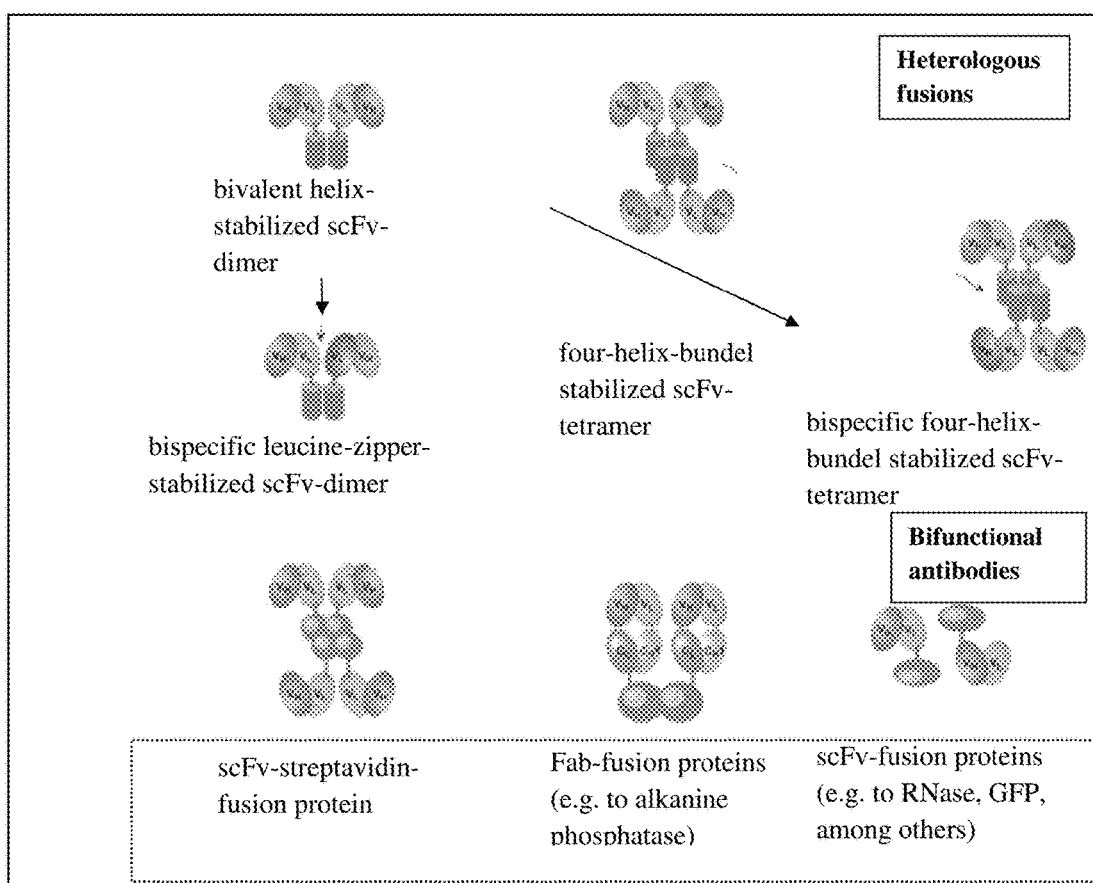
FIG. 1B—Illustration of antibody formats—heterologous fusions and bifunctional antibodies.
Figure 1C:
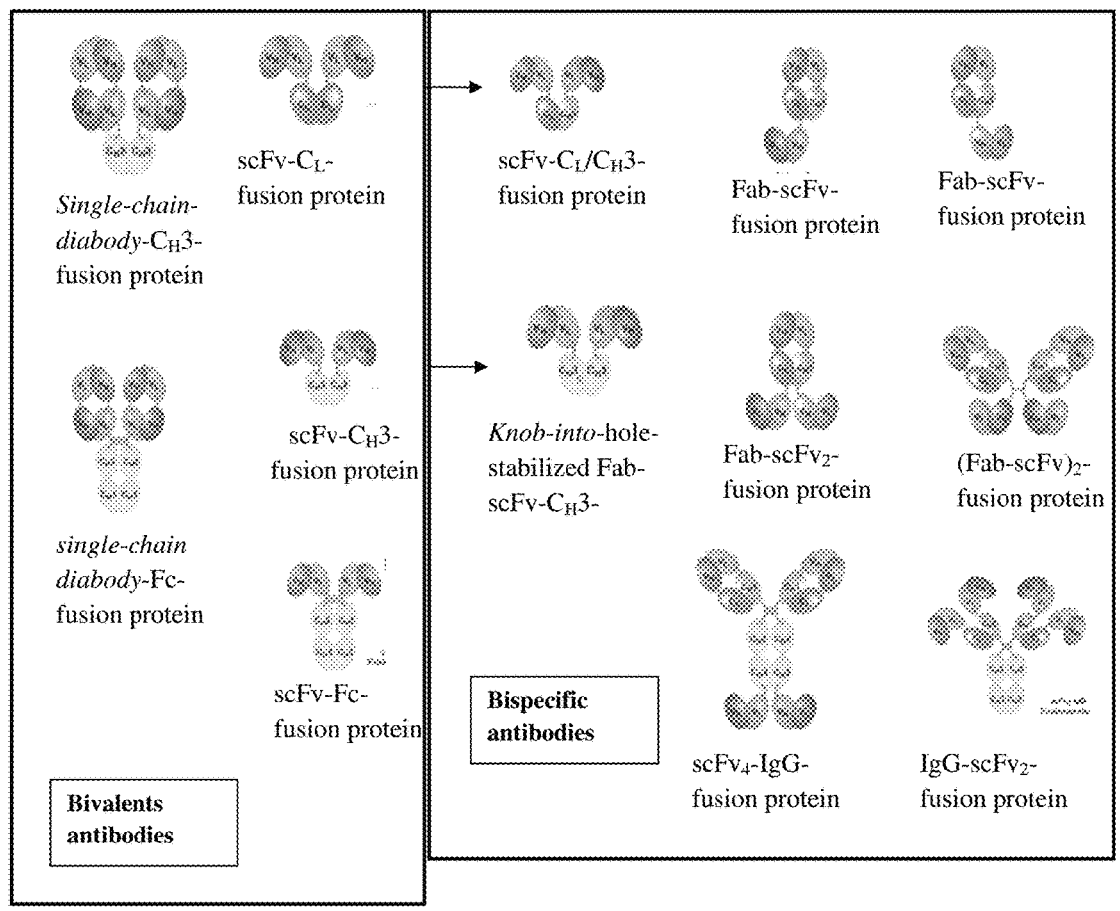
FIG. 1C—Illustration of antibody formats—bivalental antibodies and bispecific antibodies.
Figure 3A:
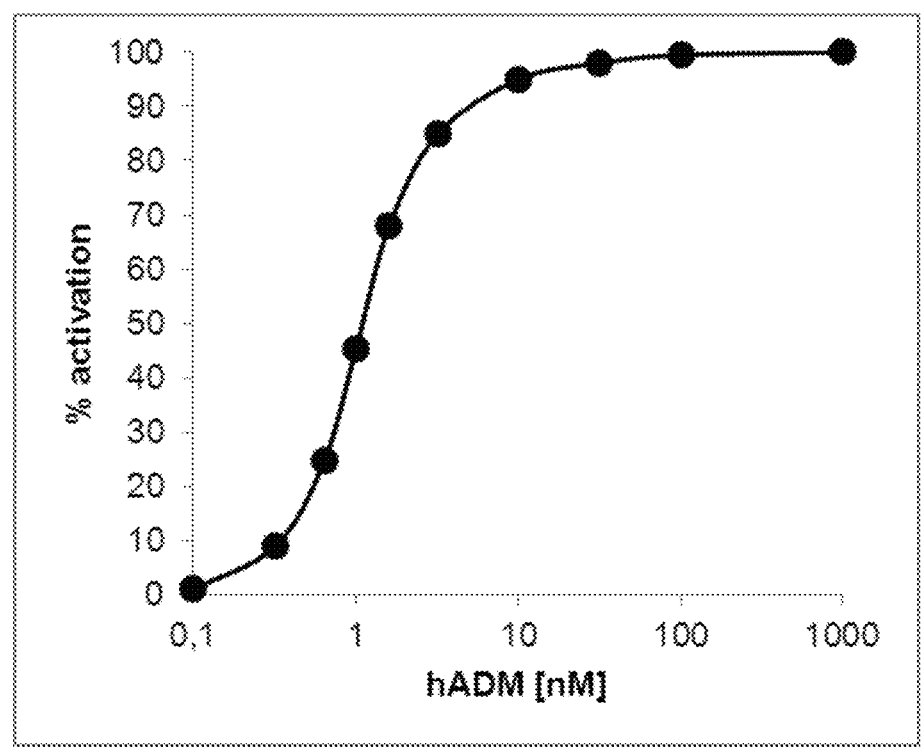
FIG. 3B—Dose/inhibition curve of human ADM 22-52 (ADM-receptor antagonist) in the presence of 5.63 nM hADM.
FIG. 3C—Dose/inhibition curve of CT-H in the presence of 5.63 nM hADM.
FIG. 3D—Dose/inhibition curve of MR-H in the presence of 5.63 nM hADM.
FIG. 3E—Dose/inhibition curve of NT-H in the presence of 5.63 nM hADM.
FIG. 3F—Dose response curve of mouse ADM. Maximal cAMP stimulation was adjusted to 100% activation.
FIG. 3G—Dose/inhibition curve of human ADM 22-52 (ADM-receptor antagonist) in the presence of 0.67 nM mADM.
FIG. 3H—Dose/inhibition curve of CT-M in the presence of 0.67 nM mADM.
FIG. 3I—Dose/inhibition curve of MR-M in the presence of 0.67 nM mADM.
FIG. 3J—Dose/inhibition curve of NT-M in the presence of 0.67 nM mADM.
FIG. 3K—shows the inhibition of ADM by F(ab)2 NT-M and by Fab NT-M.
FIG. 3L—shows the inhibition of ADM by F(ab)2 NT-M and by Fab NT-M.
Figure 3B:
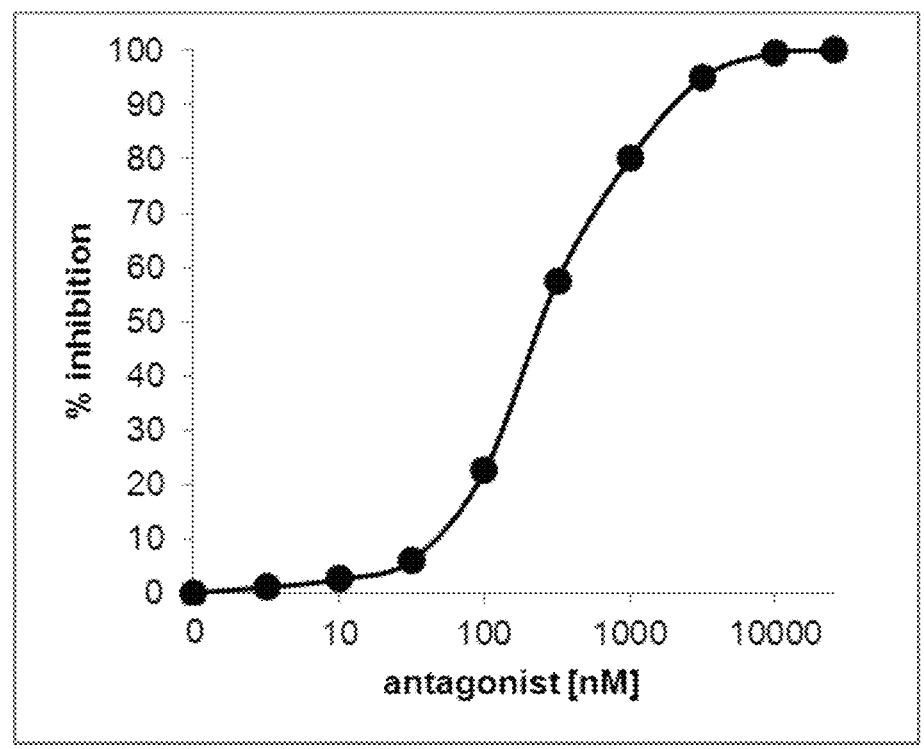
Figure 3C:
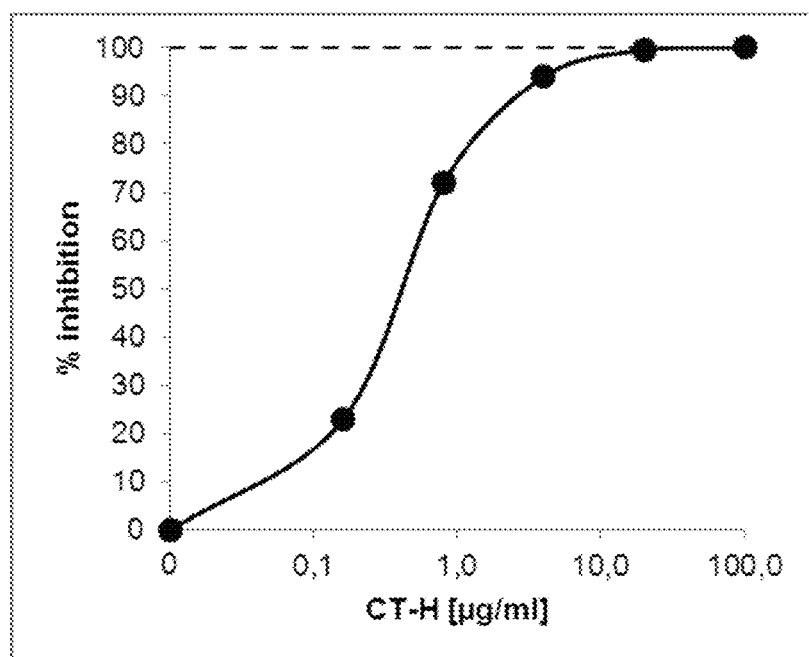
Figure 3D:
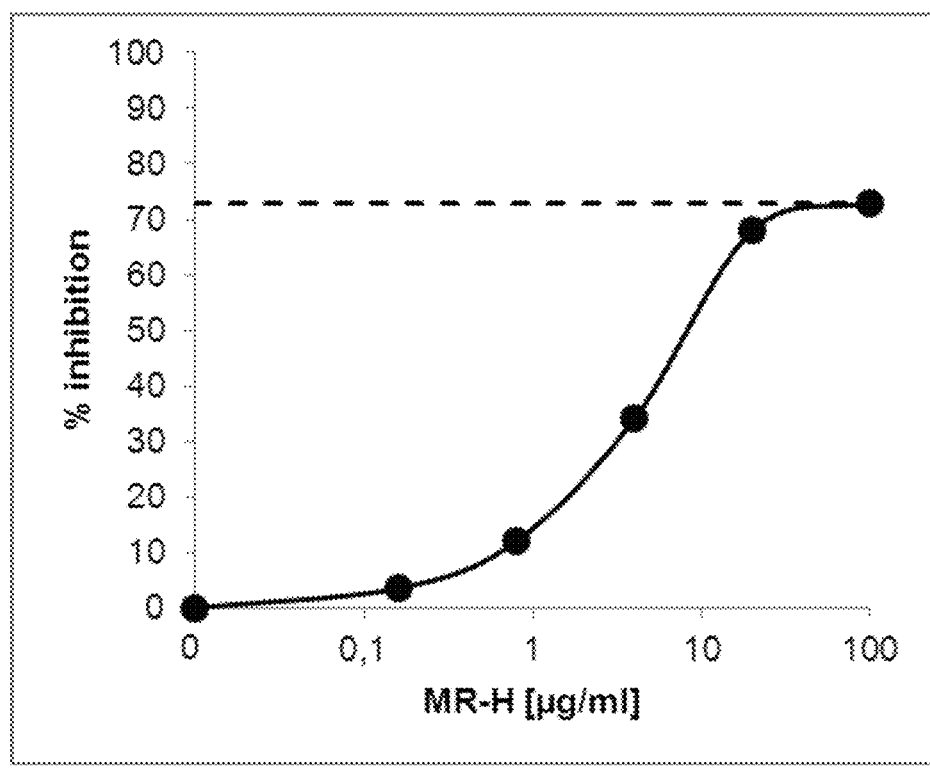
Figure 3E:
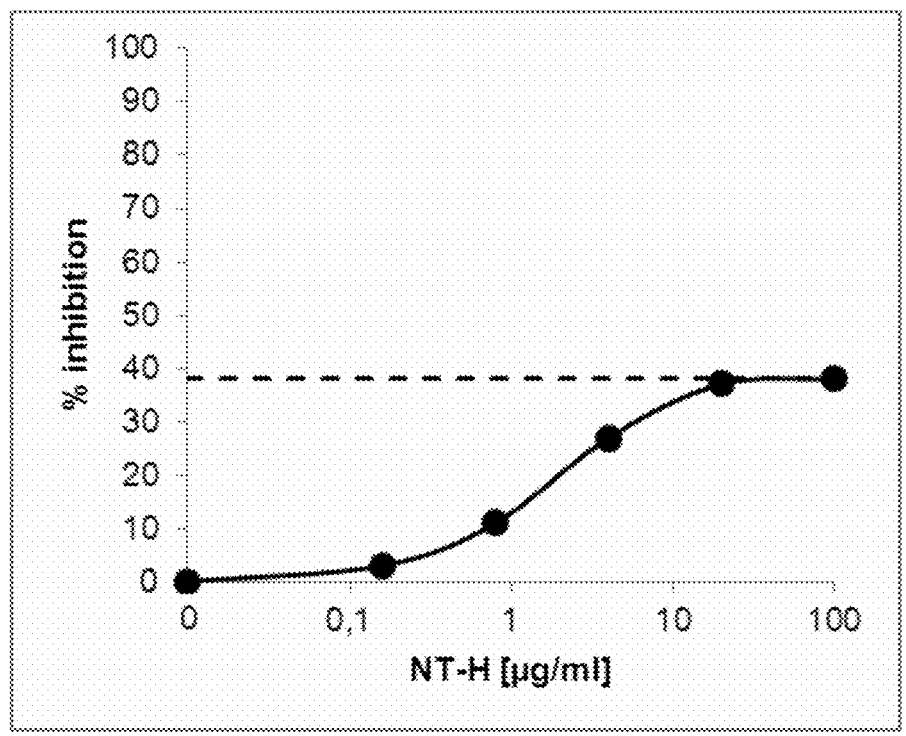
Figure 3F:
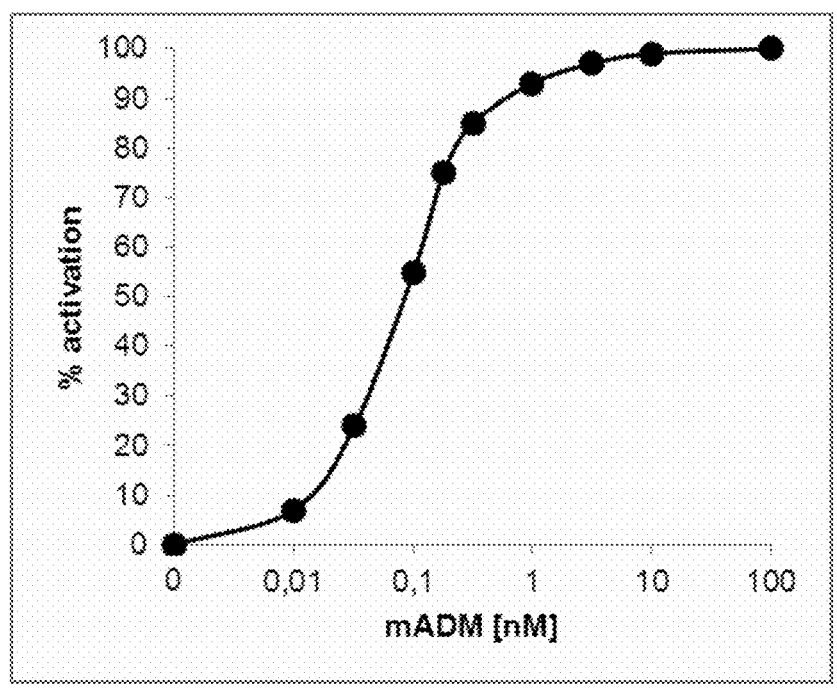
Figure 3G:
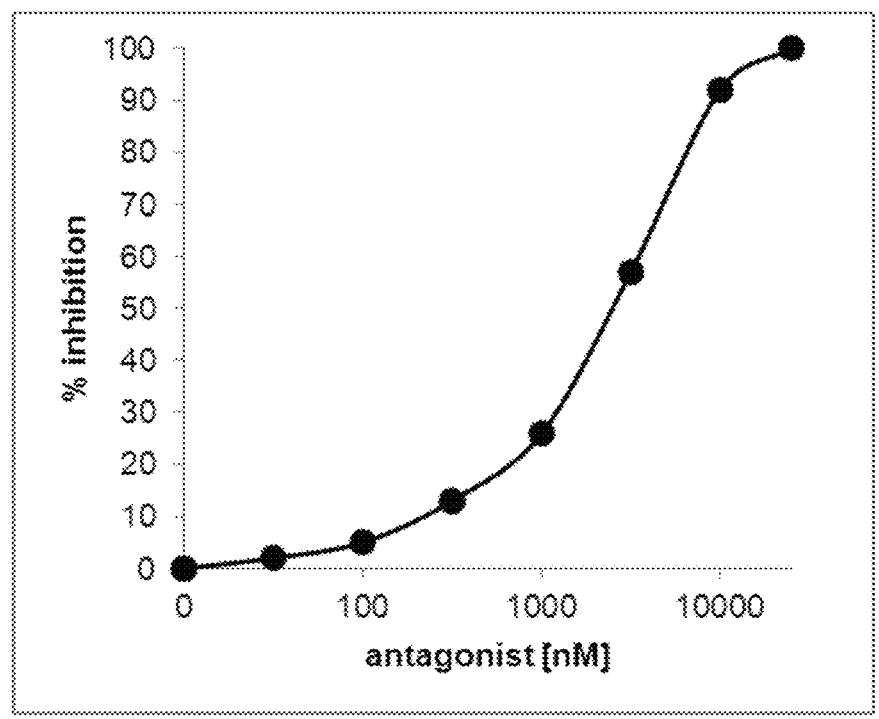
Figure 3H:
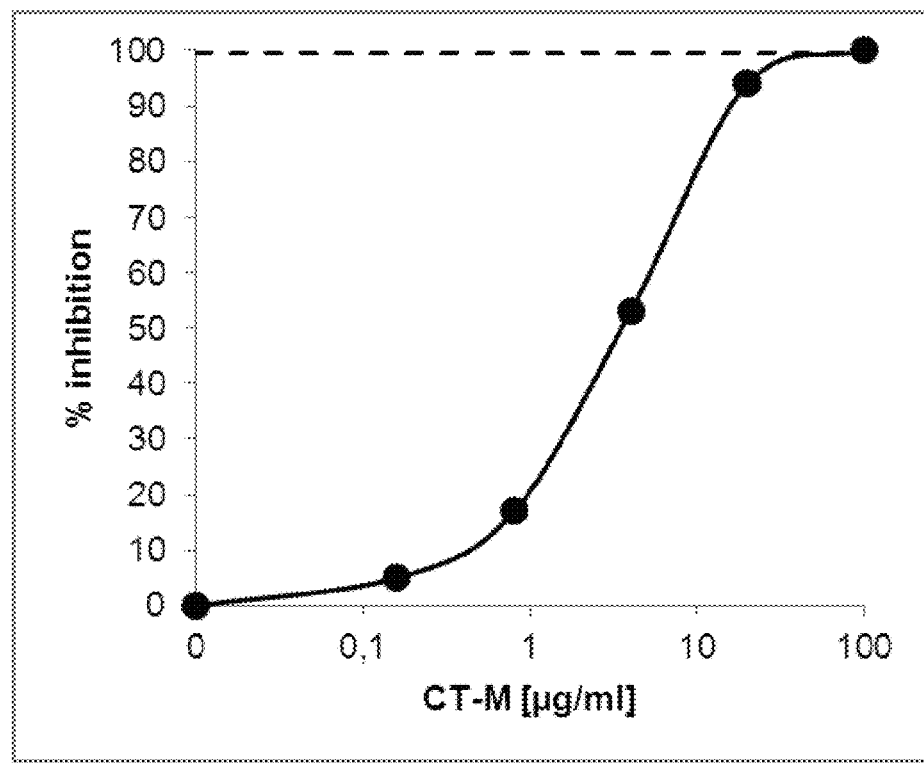
Figure 3I:
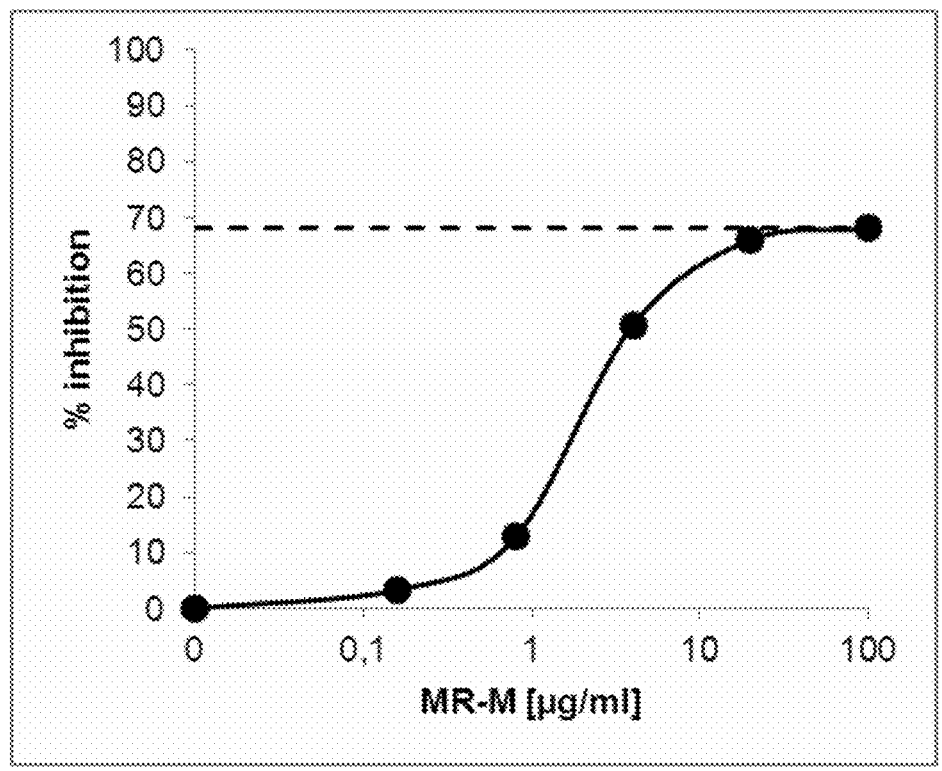
Figure 3J:
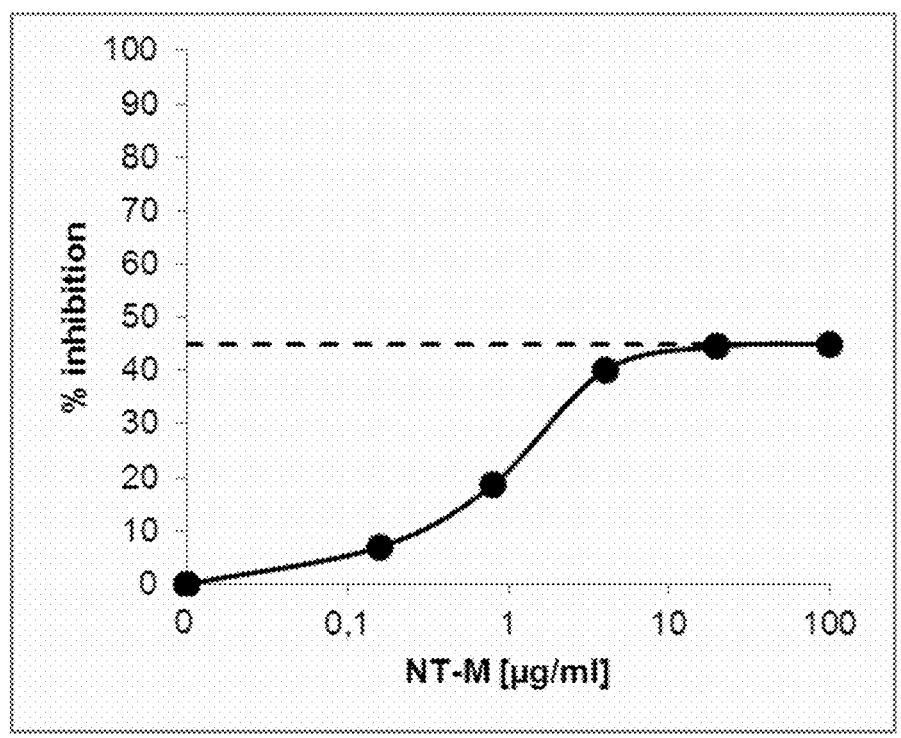
Figure 3K:
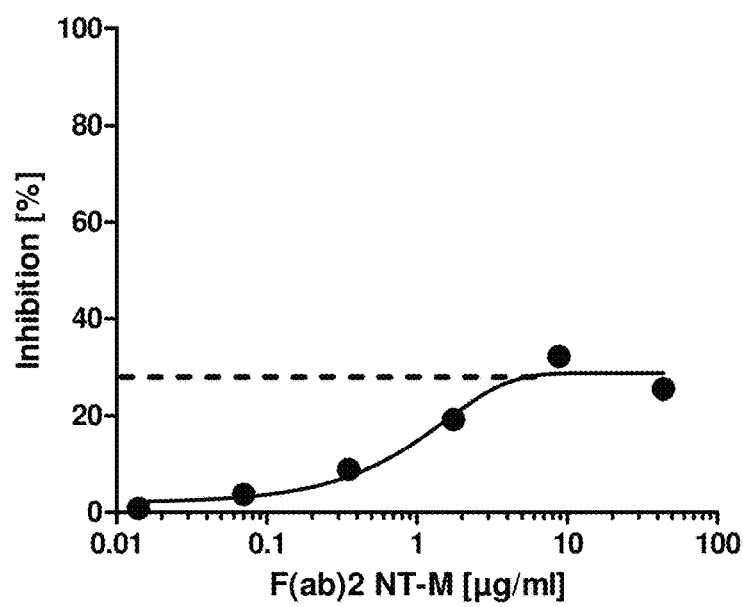
Figure 3L:
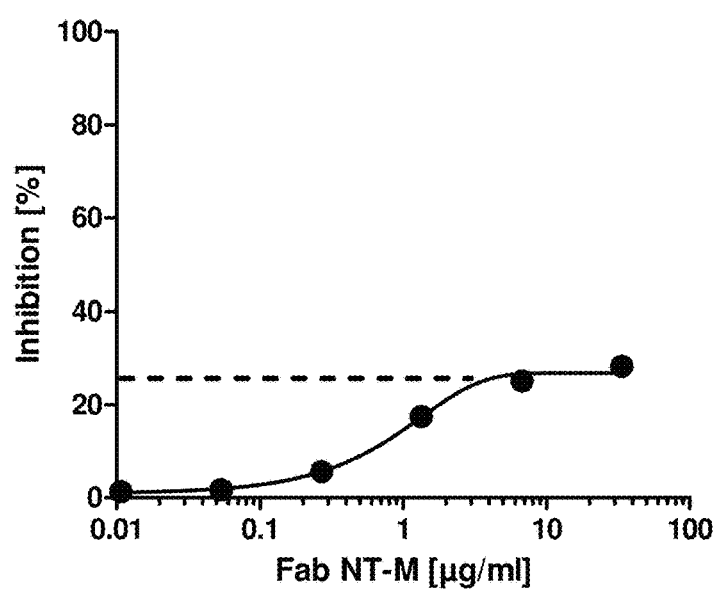

In addition to anti-ADM antibodies other biopolymer scaffolds are well known in the art to complex a target molecule and have been used for the generation of highly target specific biopolymers. Examples are aptamers, spiegelmers, anticalins and conotoxins. For illustration of antibody formats please see FIGS. 1A, 1B and 1C.

In a preferred embodiment the anti-ADM antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

In one embodiment of the invention anti-ADM antibodies according to the present invention may be produced as follows:

A Balb/c mouse was immunized with 100 µg ADM-Peptide (antigen)-BSA-Conjugate at day 0 and 14 (emulsified in 1000 complete Freund's adjuvant) and 50 µg at day 21 and 28 (in 1000 incomplete Freund's adjuvant). Three days before the fusion experiment was performed, the animal received 50 µg of the conjugate dissolved in 100 µl saline, given as one intraperitoneal and one intra-venous injection.

Spenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined. (see also Lane, R. D. (1985). A short-duration polyethylene glycol fusion technique for increasing production of monoclonal antibody-secreting hybridomas. J. Immunol. Meth. 81: 223-228; Ziegler, B. et al. (1996) Glutamate decarboxylase (GAD) is not detectable on the surface of rat islet cells examined by cytofluorometry and complement-dependent antibody-mediated cytotoxicity of monoclonal GAD antibodies, Horm. Metab. Res. 28: 11-15).

Antibodies may be produced by means of phage display according to the following procedure:

The human naive antibody gene libraries HAL7/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust, M., Meyer, T., Voedisch, B., Rülker, T., Thie, H., El-Ghezal, A., Kirsch, M. I., Schütte, M., Helmsing, S., Meier, D., Schirrmann, T., Dübel, S., 2011. A human scFv antibody generation pipeline for proteome research. Journal of Biotechnology 152, 159-170; Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of *Aspergillus fumigatus*. PLoS One 4, e6625)

Humanization of murine antibodies may be conducted according to the following procedure:

For humanization of an antibody of murine origin the antibody sequence is analyzed for the structural interaction of framework regions (FR) with the complementary determining regions (CDR) and the antigen. Based on structural modeling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling. (Almagro J C, Fransson J., 2008. Humanization of antibodies. Front Biosci. 2008 Jan. 1; 13:1619-33.)

In a preferred embodiment the ADM antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is scFab format.

In another preferred embodiment, the anti-ADM antibody, anti-ADM antibody fragment, or anti-ADM non-Ig scaffold is a full length antibody, antibody fragment, or non-Ig scaffold.

In a preferred embodiment the anti-ADM antibody or an anti-adrenomedullin antibody fragment or anti-ADM non-Ig scaffold is directed to and can bind to an epitope of at least 5 amino acids in length contained in ADM.

In a more preferred embodiment the anti-ADM antibody or an anti-adrenomedullin antibody fragment or anti-ADM non-Ig scaffold is directed to and can bind to an epitope of at least 4 amino acids in length contained in ADM.

In a preferred embodiment of the present invention said anti-ADM antibody or an anti-adrenomedullin antibody fragment or anti-ADM non-Ig scaffold binds to a region of ADM that is located in the N-terminal part (aa 1-21) of adrenomedullin, (see FIG. 2).

In another preferred embodiment said antibody or an anti-adrenomedullin antibody fragment or anti-ADM non-Ig scaffold recognizes and binds to the N-terminal end (aa1) of adrenomedullin. N-terminal end means that the amino acid 1, that is "Y" of SEQ ID NO: 21 or 23; is mandatory for binding. The antibody or fragment or scaffold would neither bind N-terminal extended nor N-terminal modified adrenomedullin nor N-terminal degraded adrenomedullin.

In one specific embodiment of the invention the anti-Adrenomedullin (ADM) antibody or anti-ADM antibody fragment binding to adrenomedullin or anti-ADM non-Ig scaffold binding to adrenomedullin is provided for use in therapy of an acute disease or acute condition of a patient wherein said antibody or antibody fragment or non-Ig scaffold binds to a region of preferably at least 4, or at least 5 amino acids within the sequence of aa 1-42 of mature human ADM:

SEQ ID NO: 24
YRQSMNNFQGLRSFGCRFGTCTVQKLAHQIYQFT-DKDKDNVA.

In one specific embodiment of the invention the anti-Adrenomedullin (ADM) antibody or anti-ADM antibody fragment binding to adrenomedullin or anti-ADM non-Ig scaffold binding to adrenomedullin is provided for use in therapy of an acute disease or acute condition of a patient wherein said antibody or fragment or scaffold binds to a region of preferably at least 4, or at least 5 amino acids within the sequence of aa 1-21 of mature human ADM:

SEQ ID NO: 23
YRQSMNNFQGLRSFGCRFGTC.

In another specific embodiment pursuant to the invention the herein provided anti-ADM antibody or anti-ADM antibody fragment or anti-ADM non-Ig scaffold does not bind to the C-terminal portion of ADM, i.e. the aa 43-52 of ADM (SEQ ID NO: 25)
PRSKISPQGY-NH2
(SEQ ID NO: 25).

In one specific embodiment it is preferred to use an anti-ADM antibody or an anti-adrenomedullin antibody fragment or anti-ADM non-Ig scaffold according to the present invention, wherein said anti-adrenomedullin antibody or said anti-adrenomedullin antibody fragment or non-Ig scaffold is an ADM stabilizing antibody or an adrenomedullin stabilizing antibody fragment or an adrenomedullin stabilizing non-Ig scaffold that enhances the half life ($t_{1/2}$; half retention time) of adrenomedullin in serum, blood, plasma at least 10%, preferably at least 50%, more preferably >50%, most preferably >100%.

The half life (half retention time) of ADM may be determined in human plasma in absence and presence of an ADM stabilizing antibody or an adrenomedullin stabilizing antibody fragment or an adrenomedullin stabilizing non-Ig scaffold, respectively, using an immunoassay for the quantification of ADM.

The following steps may be conducted:
ADM may be diluted in human citrate plasma in absence and presence of an ADM stabilizing antibody or an adrenomedullin stabilizing antibody fragment or an adrenomedullin stabilizing non-Ig scaffold, respectively, and may be incubated at 24° C.

Aliquots are taken at selected time points (e.g. within 24 hours) and degradation of ADM may be stopped in said aliquots by freezing at −20° C.

The quantity of ADM may be determined by an hADM immunoassay directly, if the selected assay is not influenced by the stabilizing antibody. Alternatively, the aliquot may be treated with denaturing agents (like HCl) and, after clearing the sample (e.g. by centrifugation) the pH can be neutralized and the ADM-quantified by an ADM immunoassay. Alternatively, non-immunoassay technologies (e.g. rpHPLC) can be used for ADM-quantification The half life of ADM is calculated for ADM incubated in absence and presence of an ADM stabilizing antibody or an adrenomedullin stabilizing antibody fragment or an adrenomedullin stabilizing non-Ig scaffold, respectively, The enhancement of half life is calculated for the stabilized ADM in comparison to ADM that has been incubated in absence of an ADM stabilizing antibody or an adrenomedullin stabilizing antibody fragment or an adrenomedullin stabilizing non-Ig scaffold.

A two-fold increase of the half life of ADM is an enhancement of half life of 100%.

Half Life (half retention time) is defined as the period over which the concentration of a specified chemical or drug takes to fall to half baseline concentration in the specified fluid or blood.

An assay that may be used for the determination of the Half life (half retention time) of adrenomedullin in serum, blood, plasma is described in Example 3.

For some diseases blocking of ADM may be beneficial to a certain extent. However, it might also be detrimental if ADM is totally neutralized as a certain amount of ADM may be required for several physiological functions. In many reports it was emphasized that the administration of ADM may be beneficial in certain diseases. In contrast thereto in other reports ADM was reported as being life threatening when administered in certain conditions.

In a preferred embodiment said anti-ADM antibody, anti-ADM antibody fragment or anti-ADM non-Ig scaffold is a non-neutralizing antibody, fragment or scaffold. A neutralizing anti-ADM antibody, anti-ADM antibody fragment or anti-ADM non-Ig scaffold would block the bioactivity of ADM to nearly 100%, to at least more than 90%, preferably to at least more than 95%.

In contrast, a non-neutralizing anti-ADM antibody, or anti-ADM antibody fragment or anti-ADM non-Ig scaffold blocks the bioactivity of ADM less than 100%, preferably to less than 95%, preferably to less than 90%, more preferred to less than 80% and even more preferred to less than 50%. This means that the residual bioactivity of ADM bound to the non-neutralizing anti-ADM antibody, or anti-ADM antibody fragment or anti-ADM non-Ig scaffold would be more than 0%, preferably more than 5%, preferably more than 10%, more preferred more than 20%, more preferred more than 50%.

In this context (a) molecule(s), being it an antibody, or an antibody fragment or a non-Ig scaffold with "non-neutralizing anti-ADM activity", collectively termed here for simplicity as "non-neutralizing" anti-ADM antibody, antibody fragment, or non-Ig scaffold, that e.g. blocks the bioactivity of ADM to less than 80%, is defined as a molecule or molecules binding to ADM, which upon addition to a culture of an eukaryotic cell line, which expresses functional human recombinant ADM receptor composed of CRLR (calcitonin receptor like receptor) and RAMP3 (receptor-activity modifying protein 3), reduces the amount of cAMP produced by the cell line through the action of parallel added human synthetic ADM peptide, wherein said added human synthetic ADM is added in an amount that in the absence of the non-neutralizing antibody to be analyzed, leads to half-maximal stimulation of cAMP synthesis, wherein the reduction of cAMP by said molecule(s) binding to ADM takes place to an extent, which is not more than 80%, even when the non-neutralizing molecule(s) binding to ADM to be analyzed is added in an amount, which is 10-fold more than the amount, which is needed to obtain the maximal reduction of cAMP synthesis obtainable with the non-neutralizing antibody to be analyzed.

The same definition applies to the other ranges; 95%, 90%, 50% etc.

In a specific embodiment according to the present invention an anti-ADM antibody or an anti-adrenomedullin antibody fragment or anti-ADM non-Ig scaffold is used, wherein said antibody or an anti-adrenomedullin antibody fragment blocks the bioactivity of ADM to less than 80%, preferably less than 50% (of baseline values). This means the antibody, antibody fragment or non-Ig scaffold pursuant to the invention blocks the bioactivity of ADM to not more than 80%, or not more than 50%, respectively. By implication, this means at least 20% residual ADM bioactivity or at least 50% residual ADM bioactivity is present when using an antibody, antibody fragment or non-Ig scaffold in accordance with the invention. It has been understood that said limited blocking of the bioactivity of ADM occurs even at excess concentration of the antibody, fragment or scaffold, meaning an excess of the antibody, fragment or scaffold in relation to ADM. Said limited blocking is an intrinsic property of the ADM binder itself. This means that said antibody, fragment or scaffold has a maximal inhibition of 80% or 50% respectively. In a preferred embodiment said anti-ADM antibody, anti-ADM antibody fragment or anti-ADM non-Ig scaffold would block the bioactivity of ADM to at least 5%. By implication, this means approximately 95% residual ADM bioactivity is present.

The bioactivity is defined as the effect that a substance takes on a living organism or tissue or organ or functional unit in vivo or in vitro (e.g. in an assay) after its interaction. In case of ADM bioactivity this may be the effect of ADM in a human recombinant Adrenomedullin receptor cAMP functional assay. Thus, according to the present invention bioactivity is defined via an Adrenomedullin receptor cAMP functional assay. The following steps may be performed in order to determine the bioactivity of ADM in such an assay:

Dose response curves are performed with ADM in said human recombinant Adrenomedullin receptor cAMP functional assay.

The ADM-concentration of half-maximal cAMP stimulation may be calculated.

At constant half-maximal cAMP-stimulating ADM-concentrations dose response curves (up to 100 µg/ml final concentration) are performed by an ADM stabilizing antibody or an adrenomedullin stabilizing antibody fragment or an adrenomedullin stabilizing non-Ig scaffold, respectively, A maximal inhibition in said ADM bioassay of 50% means that said anti-ADM antibody or said anti-ADM antibody fragment or said anti-ADM non-Ig scaffold, respectively, blocks the bioactivity to 50% of baseline values. A maximal inhibition in said ADM bioassay of 80% means that said anti-ADM antibody or said anti-adrenomedullin antibody fragment or said anti-adrenomedullin non-Ig scaffold, respectively, blocks the bioactivity of ADM to 80%. This is in the sense of blocking the ADM bioactivity to not more than 80%. This means approximately 20% residual ADM bioactivity remains present.

However, by the present specification and in the above context the expression "blocks the bioactivity of ADM" in relation to the herein disclosed anti-ADM antibodies, anti-ADM antibody fragments, and anti-ADM non-Ig scaffolds should be understood as mere decreasing the bioactivity of ADM from 100% to 20% remaining ADM bioactivity at maximum, preferably decreasing the ADM bioactivity from 100% to 50% remaining ADM bioactivity; but in any case there is ADM bioactivity remaining that can be determined as detailed above.

The bioactivity of ADM may be determined in a human recombinant Adrenomedullin receptor cAMP functional assay (Adrenomedullin Bioassay) according to Example 2.

In a preferred embodiment a modulating anti-ADM antibody or a modulating anti-ADM antibody fragment is used in the treatment of sepsis. A modulating anti-ADM antibody or a modulating anti-adrenomedullin antibody fragment enhances the bioactivity of ADM in the early phase of sepsis and reduces the damaging effects of ADM in the late phase of sepsis. A "modulating" anti-ADM antibody or a modulating anti-adrenomedullin antibody fragment is an antibody that enhances the half life ($t_{1/2}$ half retention time) of adrenomedullin in serum, blood, plasma at least 10%, preferably at least, 50%, more preferably >50%, most preferably >100% and blocks the bioactivity of ADM to less than 80%, preferably less than 50%.

In a preferred embodiment a modulating anti-ADM antibody or a modulating anti-adrenomedullin antibody fragment or a modulating anti-adrenomedullin non-Ig scaffold is used in therapy of a chronic or acute disease or acute condition of a patient for stabilizing the circulation, in particular for stabilizing the systemic circulation.

Such a modulating antibody or a modulating anti-adrenomedullin antibody fragment or a modulating anti-adrenomedullin non-Ig scaffold may be especially useful in the treatment of sepsis. A modulating antibody or a modulating anti-adrenomedullin antibody fragment or a modulating anti-adrenomedullin non-Ig scaffold enhances the bioactivity of ADM in the early phase of sepsis and reduces the damaging effects of ADM in the late phase of sepsis.

In a preferred embodiment the anti-adrenomedullin antibody or an anti-adrenomedullin antibody fragment or anti-adrenomedullin non-Ig scaffold is directed to and can bind to an epitope of at least 5 amino acids in length contained in ADM, preferably in human ADM.

In a more preferred embodiment the anti-adrenomedullin antibody or an anti-adrenomedullin antibody fragment or anti-adrenomedullin non-Ig scaffold is directed to and can bind to an epitope of at least 4 amino acids in length contained in ADM, preferably in human ADM.

A "modulating" anti-ADM antibody or a modulating anti-adrenomedullin antibody fragment or a modulating anti-adrenomedullin non-Ig scaffold is an antibody or an anti-adrenomedullin antibody fragment or non-Ig scaffold that enhances the half life ($t_{1/2}$ half retention time) of adrenomedullin in serum, blood, plasma at least 10%, preferably at least, 50%, more preferably >50%, most preferably >100% and blocks the bioactivity of ADM to less than 80%, preferably less than 50% and wherein said anti-ADM antibody, anti-ADM antibody fragment or anti-ADM non-Ig scaffold would block the bioactivity of ADM to at least 5%. These values related to half-life and blocking of bioactivity have to be understood in relation to the before-mentioned assays in order to determine these values. This is in the sense of blocking the ADM of not more than 80% or not more than 50%, respectively.

Such a modulating anti-adrenomedullin antibody or a modulating anti-adrenomedullin antibody fragment or a modulating anti-adrenomedullin non-Ig scaffold offers the advantage that the dosing of the administration is facilitated. The combination of partially blocking or partially reducing Adrenomedullin bioactivity and increase of the in vivo half life (increasing the Adrenomedullin bioactivity) leads to beneficial simplicity of anti-adrenomedullin antibody or an anti-adrenomedullin antibody fragment or anti-adrenomedullin non-Ig scaffold dosing. In a situation of excess of endogenous Adrenomedullin (maximal stimulation, late sepsis phase, shock, hypodynamic phase) the activity lowering effect is the major impact of the antibody or fragment or scaffold, limiting the (negative) effect of Adrenomedullin. In case of low or normal endogenous Adrenomedullin concentrations, the biological effect of anti-adrenomedullin antibody or an anti-adrenomedullin antibody fragment or anti-ADM non-Ig scaffold is a combination of lowering (by partially blocking) and increase by increasing the Adrenomedullin half life. If the half life effect is stronger than the net blocking effect, the biological activity of endogenous Adrenomedullin is beneficially increased in early phases of Sepsis (low Adrenomedullin, hyperdynamic phase). Thus, the non-neutralizing and modulating anti-antibody or anti-adrenomedullin antibody fragment or anti-adrenomedullin non-Ig scaffold acts like an ADM bioactivity buffer in order to keep the bioactivity of ADM within a certain physiological range.

Thus, the dosing of the antibody/fragment/scaffold in e.g. sepsis may be selected from an excessive concentration, because both Sepsis phases (early and late) benefit from excessive anti-ADM antibody or an anti-ADM antibody fragment or anti-ADM non-Ig scaffold treatment in case of a modulating effect. Excessive means: The anti-adrenomedullin antibody or an anti-adrenomedullin antibody fragment or anti-ADM non-Ig scaffold concentration is higher than endogenous Adrenomedullin during late phase (shock) of e.g. sepsis. This means, in case of a modulating antibody or modulating fragment or modulating scaffold dosing in sepsis may be as follows:

The concentration of Adrenomedullin in septic shock is 226+/−66 fmol/ml (Nishio et al., "Increased plasma concentrations of adrenomedullin correlate with relaxation of vascular tone in patients with septic shock.", Crit Care Med. 1997, 25(6):953-7), an equimolar concentration of antibody or fragment or scaffold is 42.5 µg/l blood, (based on 6 l blood volume/80 kg body weight) 3.2 µg/kg body weight. Excess means at least double (mean) septic shock Adrenomedullin concentration, at least >3 µg anti-adrenomedullin antibody or an anti-adrenomedullin antibody fragment or anti-ADM non-Ig Scaffold/kg body weight, preferred at least 6.4 µg anti-adrenomedullin antibody or an anti-adrenomedullin antibody fragment anti-ADM non-Ig Scaffold/kg body weight. Preferred >10 µg/kg, more preferred >20 µg/kg, most preferred >100 µg anti-adrenomedullin antibody or an anti-adrenomedullin antibody fragment or anti-ADM non-Ig scaffold/kg body weight. This may apply to other severe and acute conditions than septic shock as well.

In a specific embodiment of the invention the antibody is a monoclonal antibody or a fragment thereof. In one embodiment of the invention the anti-ADM antibody or the anti-ADM antibody fragment is a human or humanized antibody or derived therefrom. In one specific embodiment one or more (murine) CDR's are grafted into a human antibody or antibody fragment.

Subject matter of the present invention in one aspect is a human CDR-grafted antibody or antibody fragment thereof that binds to ADM, wherein the human CDR-grafted antibody or antibody fragment thereof comprises an antibody heavy chain (H chain) comprising

GYTFSRYW                        SEQ ID NO: 1

ILPGSGST                        SEQ ID NO: 2 and/or

TEGYEYDGFDY                     SEQ ID NO: 3 and/or further comprises an antibody light chain (L chain) comprising:

QSIVYSNGNTY                     SEQ ID NO: 4

RVS                             SEQ ID NO: 5 and/or

FQGSHIPYT.                      SEQ ID NO: 6

In one specific embodiment of the invention subject matter of the present invention is a human monoclonal antibody that binds to ADM or an antibody fragment thereof wherein the heavy chain comprises at least one CDR selected from the group comprising:

GYTFSRYW                        SEQ ID NO: 1

ILPGSGST                        SEQ ID NO: 2

TEGYEYDGFDY                     SEQ ID NO: 3 and wherein the light chain comprises at least one CDR selected from the group comprising:

QSIVYSNGNTY                     SEQ ID NO: 4

RVS                             SEQ ID NO: 5

FQGSHIPYT.                      SEQ ID NO: 6

In a more specific embodiment of the invention subject matter of the invention is a human monoclonal antibody that binds to ADM or an antibody fragment thereof wherein the heavy chain comprises the sequences

GYTFSRYW                        SEQ ID NO: 1

ILPGSGST                        SEQ ID NO: 2

TEGYEYDGFDY                     SEQ ID NO: 3 and wherein the light chain comprises the sequences

QSIVYSNGNTY                     SEQ ID NO: 4

RVS                             SEQ ID NO: 5

FQGSHIPYT.                      SEQ ID NO: 6

In a very specific embodiment the anti-ADM antibody has a sequence selected from the group comprising: SEQ ID NO: 7, 8, 9, 10, 11, 12, 13 and 14.

The anti-ADM antibody or anti-ADM antibody fragment or anti-ADM non-Ig scaffold according to the present invention exhibits an affinity towards human ADM in such that affinity constant is greater than $10^{-7}$ M, preferred $10^{-8}$ M, preferred affinity is greater than $10^{-9}$ M, most preferred higher than $10^{-10}$ M. A person skilled in the art knows that it may be considered to compensate lower affinity by applying a higher dose of compounds and this measure would not lead out-of-the-scope of the invention. The affinity constants may be determined according to the method as described in Example 1.

In a preferred embodiment the anti-ADM antibody or the anti-ADM antibody fragment or the anti-ADM non-Ig scaffold is used for reducing the risk of mortality during said chronic or acute disease or acute condition of a patient.

Chronic or acute disease or acute condition according to the present invention may be a disease or condition selected from the group comprising severe infections as e.g. meningitis, Systemic inflammatory Response-Syndrome (SIRS) sepsis; other diseases as diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata, poisoning, damages by chemotherapy. Especially useful is the antibody or fragment or scaffold according to the present invention for reducing the risk of mortality during sepsis and septic shock, i.e. late phases of sepsis.

In a preferred embodiment the antibody or the antibody fragment is used for reducing the risk of mortality during said chronic or acute disease of a patient wherein said disease is selected from the group comprising sepsis, diabetis, cancer, acute anc chronic vascular diseases as e.g. heart failure, shock as e.g. septic shock and organ dysfunction as e.g. kidney dysfunction. Especially useful is the antibody or fragment according to the present invention for reducing the risk of mortality during sepsis and septic shock, i.e. late phases of sepsis.

In a preferred embodiment a modulating antibody or a modulating adrenomedullin antibody fragment is used in the treatment of sepsis. A modulating antibody enhances the bioactivity of ADM in the early phase of sepsis and reduces the damaging effects of ADM in the late phase of sepsis. A "modulating" antibody or an adrenomedullin antibody fragment is an antibody that enhances the $t_{1/2}$ half retention time of adrenomedullin in serum, blood, plasma at least 10%, preferably at least, 50%, more preferably >50%, most preferably >100% and blocks the bioactivity of ADM to less than 80%, preferably less than 50%.

In one embodiment the anti-ADM antibody or an anti-adrenomedullin antibody fragment or anti-ADM non-Ig Scaffold is used in therapy of a chronic or acute disease or acute condition of a patient according to the present invention wherein said patient is an ICU patient. In another embodiment the anti-ADM antibody or an anti-adrenomedullin antibody fragment or anti-ADM non-Ig scaffold is used in therapy of a chronic or acute disease of a patient according to the present invention wherein said patient is critically ill. Critically ill means a patient is having a disease or state in which death is possible or imminent.

Subject of the present invention is further an anti-ADM antibody or an anti-adrenomedullin antibody fragment or anti-ADM non-Ig scaffold for use in therapy of a chronic or acute disease or acute condition of a patient according to the present invention wherein said antibody or fragment or scaffold is to be used in combination of ADM binding protein. ADM binding protein is also naturally present in the circulation of said patient.

It should be emphasized that the term ADM binding protein also denotes ADM-binding-protein-1 (complement factor H), which however is not a non-neutralizing and modulating anti-ADM antibody, anti-ADM antibody fragment, or anti-ADM non-Ig scaffold as in accordance with the invention.

Subject of the present invention is further an anti-ADM antibody or an anti-ADM antibody fragment or anti-ADM non-Ig scaffold for use in therapy of a chronic or acute disease or acute condition of a patient according to the present invention wherein said antibody or fragment or scaffold is to be used in combination with further active ingredients.

Subject matter of the invention is also an anti-adrenomedullin (ADM) antibody or an anti-adrenomedullin antibody fragment or an anti-ADM non-Ig scaffold to be used in combination with a primary medicament wherein said combination is for use in therapy of a chronic or acute disease or acute condition of a patient for prevention or reduction of organ dysfunction or organ failure in said patient.

Primary medicament means a medicament that acts against the primary cause of said disease or condition said primary medicament may be antibiotics in case of infections.

In a specific embodiment of the before mentioned combinations said combinations are to be used in combination with vasopressors e.g. catecholamine wherein said further combination is for use in therapy of a chronic or acute disease or condition of a patient for prevention or reduction of organ dysfunction or organ failure in said patient.

In one embodiment of the invention said patient having a chronic or acute disease or chronic condition being in need for prevention or reduction of organ dysfunction or organ failure in said patient is characterized by the need of the patient to get administration of vasopressors e.g. catecholamine administration.

Subject matter of the invention in one specific embodiment is, thus, an anti-adrenomedullin (ADM) antibody or an anti-adrenomedullin antibody fragment or an anti-ADM non-Ig scaffold to be used in combination with ADM binding protein and/or further active ingredients for use in therapy of a patient in need of a treatment of vasopressors e.g. catecholamine treatment.

In a specific embodiment of the above mentioned combinations said combinations are to be used in combination with fluids administered intravenously, wherein said combination is for use in therapy of a chronic or acute disease or condition of a patient for prevention or reduction of organ dysfunction or organ failure in said patient.

In one embodiment of the invention said patient having a chronic or acute disease or acute condition being in need for prevention or reduction of organ dysfunction or organ failure in said patient is characterized by the need of the patient to get intravenous fluids.

Subject matter of the invention in one specific embodiment is, thus, an anti-adrenomedullin (ADM) antibody or an anti-adrenomedullin antibody fragment or anti-ADM non-Ig scaffold in combination with ADM binding protein and/or further active ingredients for use in therapy of a patient in need of intravenous fluids.

In accordance with the invention the ADM-binding-Protein-1 may be also referred to as ADM-binding-Protein-1 (complement factor H).

In one specific embodiment of the invention the anti-adrenomedullin (ADM) antibody or anti-ADM antibody fragment binding to adrenomedullin or anti-ADM non-Ig scaffold binding to adrenomedullin is provided for use in therapy of an acute disease or acute condition of a patient wherein said antibody or fragment or scaffold is not ADM-binding-Protein-1 (complement factor H).

It should be emphasized that the term ADM binding protein also denotes ADM-binding-protein-1 (complement factor H), which however is not a non-neutralizing and modulating anti-ADM antibody, anti-ADM antibody fragment, or anti-ADM non-Ig scaffold as in accordance with the invention.

Said anti-ADM antibody or an anti-adrenomedullin antibody fragment or anti-ADM non-Ig scaffold or combinations thereof with ADM binding protein and/or further active ingredients may be used in combination with vasopressors e.g. catecholamine and/or with fluids administered intravenously for use in a of a chronic or acute disease or acute condition of a patient for prevention or reduction of organ dysfunction or organ failure in said patient.

Subject matter of the invention is also an anti-ADM antibody or an anti-adrenomedullin antibody fragment or anti-ADM non-Ig scaffold according to the present invention to be used in combination with TNF-alpha-antibodies. TNF-alpha-antibodies are commercially available for the treatment of patients.

Subject of the present invention is further a pharmaceutical formulation comprising an antibody or fragment or scaffold according to the present invention. Subject of the present invention is further a pharmaceutical formulation according to the present invention wherein said pharmaceutical formulation is a solution, preferably a ready-to-use solution.

Said pharmaceutical formulation may be administered intra-muscular. Said pharmaceutical formulation may be administered intra-vascular. Said pharmaceutical formulation may be administered via infusion. In another embodiment subject of the present invention is further a pharmaceutical formulation according to the present invention wherein said pharmaceutical formulation is in a dried state to be reconstituted before use.

In another embodiment subject of the present invention is further a pharmaceutical formulation according to the present invention wherein said pharmaceutical formulation is in a freeze-dried state.

In another embodiment subject of the present invention is further a pharmaceutical formulation according to the present invention wherein said pharmaceutical formulation is administered intra-muscular.

In another embodiment subject of the present invention is further a pharmaceutical formulation according to the present invention wherein said pharmaceutical formulation is administered intra-vascular.

In another embodiment subject of the present invention is further a pharmaceutical formulation according to the present invention wherein said pharmaceutical formulation is administered via infusion.

It should be emphasized that the pharmaceutical formulation in accordance with the invention as may be administered intra-muscular, intra-vascular, or via infusion is preferably administered systemically to a patient for prevention or reduction of organ dysfunction or organ failure in a patient having a chronic or acute disease or acute condition.

Therefore, in another embodiment of the present invention the pharmaceutical formulation according to the present invention is to be administered systemically to a patient for prevention or reduction of organ dysfunction or organ failure in a patient having a chronic or acute disease or acute condition.

In another specific and preferred embodiment of the present invention the pharmaceutical formulation according to the present invention is to be administered systemically via infusion to a patient for prevention or reduction of organ dysfunction or organ failure in a patient having a chronic or acute disease or acute condition.

Further embodiments within the scope of the present invention are set out below:

1. Adrenomedullin ADM antibody or an adrenomedullin antibody fragment for use in therapy of a chronic or acute disease of a patient for the regulation of liquid balance.
2. ADM antibody or an adrenomedullin antibody fragment according to embodiment 1 wherein the antibody format is selected from the group comprising Fv fragment, scFv fragment, Fab fragment, scFab fragment, (Fab)2 fragment and scFv-Fc Fusion protein.
3. ADM antibody or an adrenomedullin antibody fragment according embodiment 1 or 2 wherein said antibody or fragment binds to the N-terminal part (aa 1-21) of adrenomedullin.
4. ADM antibody or an adrenomedullin antibody fragment according to any of embodiments 1 to 3, wherein said antibody or fragment recognizes and binds to the N-terminal end (aa1) of adrenomedullin.
5. ADM antibody or an adrenomedullin antibody fragment according to any of embodiments 1 to 4, wherein said antibody or fragment is an ADM stabilizing antibody or ADM stabilizing a antibody fragment that enhances the $t_{1/2}$ half retention time of adrenomedullin in serum, blood, plasma at least 10%, preferably at least 50%, more preferably >50%, most preferably >100%.
6. ADM antibody or an adrenomedullin antibody fragment according to any of embodiments 1 to 5, wherein said antibody or fragment blocks the bioactivity of ADM to less than 80%, preferably less than 50%.
7. ADM antibody or an adrenomedullin antibody fragment for use in therapy of a chronic or acute disease of a patient according to any of embodiments 1 to 6 wherein said disease is selected from the group comprising sepsis, diabetis, cancer, heart failure, shock and kidney dysfunction.
8. ADM antibody or an adrenomedullin antibody fragment for use in therapy of a chronic or acute disease of a patient according to any of embodiments 1 to 7 wherein said patient is an ICU patient.
9. ADM antibody or an adrenomedullin antibody fragment for use in therapy of a chronic or acute disease of a patient according to any of embodiments 1 to 7 wherein said antibody or fragment is a modulating antibody or fragment that enhances the $t_{1/2}$ half retention time of adrenomedullin in serum, blood, plasma at least 10%, preferably at least 50%, more preferably >50%, most preferably >100% and that blocks the bioactivity of ADM to less than 80%, preferably less than 50%.
10. Pharmaceutical formulation comprising an antibody or fragment according to any of embodiments 1 to 9.
11. Pharmaceutical formulation according to embodiment 10 wherein said pharmaceutical formulation is a solution, preferably a ready-to-use solution.
12. Pharmaceutical formulation according to embodiment 10 wherein said pharmaceutical formulation is in a freeze-dried state.
13. Pharmaceutical formulation according to any of embodiments 10 to 11, wherein said pharmaceutical formulation is administered intra-muscular.
14. Pharmaceutical formulation according to any of embodiments 10 to 11, wherein said pharmaceutical formulation is administered intra-vascular.
15. Pharmaceutical formulation according to embodiment 14, wherein said pharmaceutical formulation is administered via infusion.

Further embodiments within the scope of the present invention are set out below:

1. Adrenomedullin ADM antibody or an adrenomedullin antibody fragment an ADM non-Ig scaffold for use in therapy of a chronic or acute disease or acute condition of a patient for the regulation of fluid balance.
2. ADM antibody or an adrenomedullin antibody fragment or ADM non-IG scaffold according to embodiment 1 wherein said ADM antibody or an adrenomedullin antibody fragment or ADM non-IG scaffold is a non-neutralizing ADM antibody or a non-neutralizing adrenomedullin antibody fragment or a non-neutralizing ADM non-IG scaffold.
3. Adrenomedullin ADM antibody or an adrenomedullin antibody fragment or an ADM non-Ig scaffold for use in therapy of a chronic or acute disease or acute condition according to embodiment 1 or 2 for preventing or reducing edema in said patient.
4. ADM antibody or an adrenomedullin antibody fragment or ADM non-IG scaffold according to any of embodiments 1 to 3 wherein the antibody format is selected from the group comprising Fv fragment, scFv fragment, Fab fragment, scFab fragment, (Fab)2 fragment and scFv-Fc Fusion protein.
5. ADM antibody or an adrenomedullin antibody fragment or ADM non-IG scaffold according to any of embodiments 1 to 4, wherein said antibody or fragment or scaffold binds to the N-terminal part (aa 1-21) of adrenomedullin.
6. ADM antibody or an adrenomedullin antibody fragment or ADM non-IG scaffold according to any of embodiments 1 to 5, wherein said antibody or fragment scaffold recognizes and binds to the N-terminal end (aa 1) of adrenomedullin.
7. ADM antibody or an adrenomedullin antibody fragment or ADM non-IG scaffold according to any of embodiments 1 to 6, wherein said antibody or fragment or scaffold is an ADM stabilizing antibody or ADM stabilizing antibody fragment or ADM stabilizing non-IG scaffold that enhances the half life ($t_{1/2}$ half retention time) of adrenomedullin in serum, blood, plasma at least 10%, preferably at least 50%, more preferably >50%, most preferably >100%.

8. ADM antibody or an adrenomedullin antibody fragment or ADM non-IG scaffold according to any of embodiments 1 to 7, wherein said antibody or fragment blocks the bioactivity of ADM to less than 80%, preferably less than 50%.

9. ADM antibody or an adrenomedullin antibody fragment or ADM non-IG scaffold for use in therapy of a chronic or acute disease of a patient according to any of embodiments 1 to 8 wherein said disease is selected from the group comprising SIRS, sepsis, diabetis, cancer, heart failure, shock and kidney dysfunction 10. ADM antibody or an adrenomedullin antibody fragment according to any of embodiments 1 to 9, wherein said antibody or fragment is a human monoclonal antibody or fragment that binds to ADM or an antibody fragment thereof wherein the heavy chain comprises the sequences

SEQ ID NO: 1
GYTFSRYW

SEQ ID NO: 2
ILPGSGST

SEQ ID NO: 3
TEGYEYDGFDY and wherein the light chain comprises the sequences

SEQ ID NO: 4
QSIVYSNGNTY

SEQ ID NO: 5
RVS

SEQ ID NO: 6
FQGSHIPYT.

11. A human monoclonal antibody or fragment that binds to ADM or an antibody fragment thereof according to embodiment 10 wherein said antibody or fragment comprises a sequence selected from the group comprising:

(AM-VH-C)
SEQ ID NO: 7
QVQLQQSGAELMKPGASVKISCKATGYTFSRYWIEWVKQRPGHGLEWIGE

ILPGSGSTNYNEKFKGKATITADTSSNTAYMQLSSLTSEDSAVYYCTEGY

EYDGFDYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH1)
SEQ ID NO: 8
QVQLVQSGAEVKKPGSSVKVSCKASGYTFSRYWISWVRQAPGQGLEWMG

RILPGSGSTNYAQKFQGRVTITADESTSTAYMELSSLRSEDTAVYYCTEG

YEYDGFDYWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKHHHHHH (AM-VH2-E40)
SEQ ID NO: 9
QVQLVQSGAEVKKPGSSVKVSCKASGYTFSRYWIEWVRQAPGQGLEWM

GRILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKHHHHHH (AM-VH3-T26-E55)
SEQ ID NO: 10
QVQLVQSGAEVKKPGSSVKVSCKATGYTFSRYWISWVRQAPGQGLEWM

GEILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKHHHHHH (AM-VH4-T26-E40-E55)
SEQ ID NO: 11
QVQLVQSGAEVKKPGSSVKVSCKATGYTFSRYWIEWVRQAPGQGLEWM

GEILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKHHHHHH (AM-VL-C)
SEQ ID NO: 12
DVLLSQTPLSLPVSLGDQATISCRSSQSIVYSNGNTYLEWYLQKPGQSPK

LLIYRVSNRFSGVPDRFSGSGSGTDFTLKISRVEAEDLGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC (AM-VL1)
SEQ ID NO: 13
DVVMTQSPLSLPVTLGQPASISCRSSQSIVYSNGNTYLNWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC (AM-VL2-E40)
SEQ ID NO: 14
DVVMTQSPLSLPVTLGQPASISCRSSQSIVYSNGNTYLEWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

12. ADM antibody or an adrenomedullin antibody fragment or ADM non-IG scaffold for use in therapy of a chronic or acute disease of a patient according to any of embodiments 1 to 9 wherein said patient is an ICU patient.
13. ADM antibody or an adrenomedullin antibody fragment or ADM non-IG scaffold for use in therapy of a chronic or acute disease of a patient according to any of embodiments 1 to 12 wherein said antibody or fragment or scaffold is a modulating antibody or fragment or scaffold that enhances the half life ($t_{1/2}$ half retention time) of adrenomedullin in serum, blood, plasma at least 10%, preferably at least 50%, more preferably >50%, most preferably >100% and that blocks the bioactivity of ADM to less than 80%, preferably less than 50%.
14. ADM antibody or an adrenomedullin antibody fragment or ADM non-IG scaffold for use in therapy of a chronic or acute disease of a patient according to any of the embodiments 1 to 13 to be used in combination with catecholamine and/or fluids administered intravenously.
15. ADM antibody or adrenomedullin antibody fragment or ADM non-IG scaffold for use in therapy of a chronic or acute disease of a patient according to any of the embodiments 1 to 13 or a combination according to embodiments 12 to be used in combination with ADM binding protein and/or further active ingredients.
16. Pharmaceutical formulation comprising an antibody or fragment or scaffold according to any of embodiments 1 to 15.
17. Pharmaceutical formulation according to embodiment 16 wherein said pharmaceutical formulation is a solution, preferably a ready-to-use solution.
18. Pharmaceutical formulation according to embodiment 16 wherein said pharmaceutical formulation is in a freeze-dried state.
19. Pharmaceutical formulation according to any of embodiments 16 to 17, wherein said pharmaceutical formulation is administered intra-muscular.
20. Pharmaceutical formulation according to any of embodiments 16 to 17, wherein said pharmaceutical formulation is administered intra-vascular.
21. Pharmaceutical formulation according to embodiment 20, wherein said pharmaceutical formulation is administered via infusion.

Further embodiments within the scope of the present invention are set out below:
1. Adrenomedullin (ADM) antibody or an adrenomedullin antibody fragment for use in therapy of a chronic or acute disease of a patient for stabilizing the circulation.
2. ADM antibody or an adrenomedullin antibody fragment according to embodiment 1 wherein said antibody or fragment reduces the catecholamine requirement of said patient.
3. ADM antibody or an adrenomedullin antibody fragment according to embodiment 1 or 2 wherein the antibody format is selected from the group comprising Fv fragment, scFv fragment, Fab fragment, scFab fragment, (Fab)2 fragment and scFv-Fc Fusion protein.
4. ADM antibody or an adrenomedullin antibody fragment according to any of embodiment 1 to 3 wherein said antibody or fragment binds to the N-terminal part (aa 1-21) of adrenomedullin.
5. ADM antibody or an adrenomedullin antibody fragment according to any of embodiment 1 to 4, wherein said antibody or fragment recognizes and binds to the N-terminal end (aa1) of adrenomedullin.
6. ADM antibody or an adrenomedullin antibody fragment according to any of embodiments 1 to 5, wherein said antibody or fragment is an ADM stabilizing antibody that enhances the t1/2 half retention time of adrenomedullin in serum, blood, plasma at least 10%, preferably at least, 50%, more preferably >50%, most preferably >100%.
7. ADM antibody or an adrenomedullin antibody fragment according to any of embodiments 1 to 6, wherein said antibody or fragment blocks the bioactivity of ADM to less than 80%, preferably less than 50%.
8. ADM antibody or an adrenomedullin antibody fragment according to any of embodiments 1 to 7, wherein said antibody or fragment is a modulating ADM antibody or a modulating adrenomedullin antibody fragment that enhances the t1/2 half retention time of adrenomedullin in serum, blood, plasma at least 10%, preferably at least, 50%, more preferably >50%, most preferably >100% and that blocks the bioactivity of ADM to less than 80%, preferably less than 50%:
9. ADM antibody or an adrenomedullin antibody fragment for use in therapy of a chronic or acute disease of a patient according to any of the embodiments 1 to 8 wherein said disease is selected from the group comprising sepsis, diabetis, cancer, acute and chronic vascular diseases as e.g. heart failure, shock as e.g. septic shock and organ dysfunction as e.g. kidney dysfunction.
10. Pharmaceutical formulation comprising an antibody according to any of embodiments 1 to 9.
11. Pharmaceutical formulation according to embodiments 10 wherein said pharmaceutical formulation is a solution, preferably a ready-to-use solution.
12. Pharmaceutical formulation according to embodiment 10 wherein said pharmaceutical formulation is in a freeze-dried state.
13. Pharmaceutical formulation according to any of embodiments 10 to 11, wherein said pharmaceutical formulation is administered intra-muscular.
14. Pharmaceutical formulation according to any of embodiments 10 to 11, wherein said pharmaceutical formulation is administered intra-vascular.
15. Pharmaceutical formulation according to embodiment 14, wherein said pharmaceutical formulation is administered via infusion.

Further embodiments within the scope of the present invention are set out below:
1. Adrenomedullin (ADM) antibody or an adrenomedullin antibody fragment or an ADM non-IG scaffold for use in therapy of a chronic or acute disease or condition of a patient for stabilizing the circulation.
2. ADM antibody or an adrenomedullin antibody fragment or ADM non-IG scaffold according to embodiment 1 wherein said antibody or fragment or scaffold reduces the vasopressor requirement, e.g. catecholamine requirement of said patient.
3. ADM antibody or an adrenomedullin antibody fragment or ADM non-IG scaffold according to embodiment 1 or 2 wherein said ADM antibody or an adrenomedullin antibody fragment or ADM non-IG scaffold is a non-neutralizing ADM antibody or a non-neutralizing adrenomedullin antibody fragment or a non-neutralizing ADM non-IG scaffold.
4. ADM antibody or an adrenomedullin antibody fragment according to any of embodiments 1 to 3 wherein the antibody format is selected from the group comprising Fv fragment, scFv fragment, Fab fragment, scFab fragment, (Fab)2 fragment and scFv-Fc Fusion protein.

5. ADM antibody or an adrenomedullin antibody fragment or ADM non-IG scaffold according to any of embodiments 1 to 4 wherein said antibody or fragment or scaffold binds to the N-terminal part (aa 1-21) of adrenomedullin.
6. ADM antibody or an adrenomedullin antibody fragment or ADM non-IG scaffold according to any of embodiments 1 to 5, wherein said antibody or fragment or scaffold recognizes and binds to the N-terminal end (aa1) of adrenomedullin.
7. ADM antibody or an adrenomedullin antibody fragment or ADM non-IG scaffold according to any of embodiments 1 to 6, wherein said antibody or fragment or scaffold is an ADM stabilizing antibody or fragment or scaffold that enhances the half life (t1/2 half retention time) of adrenomedullin in serum, blood, plasma at least 10%, preferably at least, 50%, more preferably >50%, most preferably >100%.
8. ADM antibody or an adrenomedullin antibody fragment or ADM non-IG scaffold according to any of embodiments 1 to 7, wherein said antibody or fragment or scaffold blocks the bioactivity of ADM to less than 80%, preferably less than 50%.
9. ADM antibody or an adrenomedullin antibody fragment or ADM non-IG scaffold according to any of embodiments 1 to 8, wherein said antibody or fragment or scaffold is a modulating ADM antibody or a modulating adrenomedullin antibody fragment or scaffold that enhances the half life (t1/2 half retention time) of adrenomedullin in serum, blood, plasma at least 10%, preferably at least, 50%, more preferably >50%, most preferably >100% and that blocks the bioactivity of ADM to less than 80%, preferably less than 50%:
10. ADM antibody or an adrenomedullin antibody fragment according to any of embodiments 1 to 9, wherein said antibody or fragment is a human monoclonal antibody or fragment that binds to ADM or an antibody fragment thereof wherein the heavy chain comprises the sequences

```
                                    SEQ ID NO: 1
GYTFSRYW

SEQ ID NO: 2
ILPGSGST

SEQ ID NO: 3
TEGYEYDGFDY
``` and wherein the light chain comprises the sequences

```
                                    SEQ ID NO: 4
QSIVYSNGNTY

SEQ ID NO: 5
RVS

SEQ ID NO: 6
FQGSHIPYT.
```

11. A human monoclonal antibody or fragment that binds to ADM or an antibody fragment thereof according to embodiment 10 wherein said antibody or fragment comprises a sequence selected from the group comprising:

```
(AM-VH-C)
                                    SEQ ID NO: 7
QVQLQQSGAELMKPGASVKISCKATGYTFSRYWIEWVKQRPGHGLEWIGE

ILPGSGSTNYNEKFKGKATITADTSSNTAYMQLSSLTSEDSAVYYCTEGY

EYDGFDYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH1)
                                    SEQ ID NO: 8
QVQLVQSGAEVKKPGSSVKVSCKASGYTFSRYWISWVRQAPGQGLEWMGR

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH2-E40)
                                    SEQ ID NO: 9
QVQLVQSGAEVKKPGSSVKVSCKASGYTFSRYWIEWVRQAPGQGLEWMGR

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH3-T26-E55)
                                    SEQ ID NO: 10
QVQLVQSGAEVKKPGSSVKVSCKATGYTFSRYWISWVRQAPGQGLEWMGE

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH4-T26-E40-E55)
                                    SEQ ID NO: 11
QVQLVQSGAEVKKPGSSVKVSCKATGYTFSRYWIEWVRQAPGQGLEWMGE

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VL-C)
                                    SEQ ID NO: 12
DVLLSQTPLSLPVSLGDQATISCRSSQSIVYSNGNTYLEWYLQKPGQSPK

LLIYRVSNRFSGVPDRFSGSGSGTDFTLKISRVEAEDLGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC (AM-VL1)
                                    SEQ ID NO: 13
DVVMTQSPLSLPVTLGQPASISCRSSQSIVYSNGNTYLNWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

-continued (AM-VL2-E40)
SEQ ID NO: 14
DVVMTQSPLSLPVTLGQPASISCRSSQSIVYSNGNTYLEWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

12. ADM antibody or an adrenomedullin antibody fragment or ADM non-IG scaffold for use in therapy of a chronic or acute disease of a patient according to any of the embodiments 1 to 11 wherein said disease is selected from the group comprising SIRS, sepsis, diabetis, cancer, acute and chronic vascular diseases as e.g. heart failure, shock as e.g. septic shock and organ dysfunction as e.g. kidney dysfunction.
13. ADM antibody or an adrenomedullin antibody fragment or ADM non-IG scaffold for use in therapy of a chronic or acute disease of a patient according to any of the embodiments 1 to 12 to be used in combination with catecholamine and/or fluids administered intravenously.
14. ADM antibody or adrenomedullin antibody fragment or ADM non-IG scaffold for use in therapy of a chronic or acute disease of a patient according to any of the embodiments 1 to 13 or a combination according to claim 10 to be used in combination with ADM binding protein and/or further active ingredients.
15. Pharmaceutical formulation comprising an antibody or fragment or non-IG scaffold according to any of embodiments 1 to 14.
16. Pharmaceutical formulation according to embodiments 15 wherein said pharmaceutical formulation is a solution, preferably a ready-to-use solution.
17. Pharmaceutical formulation according to embodiment 15 wherein said pharmaceutical formulation is in a freeze-dried state.
18. Pharmaceutical formulation according to any of embodiments 15 to 16, wherein said pharmaceutical formulation is administered intra-muscular.
19. Pharmaceutical formulation according to any of embodiments 14 to 16, wherein said pharmaceutical formulation is administered intra-vascular.
20. Pharmaceutical formulation according to embodiment 16, wherein said pharmaceutical formulation is administered via infusion.

Further embodiments within the scope of the present invention are set out below:

1. Adrenomedullin antibody or an adrenomedullin antibody fragment for use in a treatment of a chronic or acute disease wherein said antibody or said fragment is an ADM stabilizing antibody or fragment that enhances the $t_{1/2}$ half retention time of adrenomedullin in serum, blood, plasma at least 10%, preferably at least, 50%, more preferably >50%, most preferably 100% and/or wherein said antibody blocks the bioactivity of ADM to less than 80%, preferably to less than 50%.
2. Adrenomedullin antibody or an adrenomedullin antibody fragment for use in a treatment of a chronic or acute disease wherein said antibody or said fragment is a modulating ADM antibody or fragment that enhances the $t_{1/2}$ half retention time of adrenomedullin in serum, blood, plasma at least 10%, preferably at least, 50%, more preferably >50%, most preferably 100% and that blocks the bioactivity of ADM to less than 80%, preferably to less than 50%.
3. Adrenomedullin antibody or an adrenomedullin antibody fragment for use in a treatment of a chronic or acute disease according to embodiment 1 or 2, wherein said antibody or fragment binds to the N-terminal part (aa 1-21) of adrenomedullin.
4. Adrenomedullin antibody or an adrenomedullin antibody fragment for use in a treatment of a chronic or acute disease wherein said antibody or said fragment according to embodiment 3 binds to the N-terminal end of adrenomedullin.
5. Adrenomedullin antibody or an adrenomedullin antibody fragment for use in use in a treatment of a chronic or acute disease according to any of embodiments 1 to 4, wherein said antibody or said fragment is an ADM stabilizing antibody or fragment that enhances the $t_{1/2}$ half retention time of adrenomedullin in serum, blood, plasma at least 10%, preferably at least, 50%, more preferably >50%, most preferably 100%.
6. Adrenomedullin antibody or an adrenomedullin antibody fragment for use in a treatment of a chronic or acute disease according to any of embodiments 1 to 5, wherein said antibody or said fragment blocks the bioactivity of ADM to less than 80%, preferably to less than 50%.
7. Adrenomedullin antibody or an adrenomedullin antibody fragment according to any of the embodiments 1 to 6 for use in a treatment of a chronic or acute disease wherein said disease is selected from the group comprising SIRS, sepsis, septic shock, diabetis, cancer, heart failure, shock, organ failure, kidney dysfunction, acute liquid dysbalance, and low blood pressure.
8. Adrenomedullin antibody or an adrenomedullin antibody fragment according to any of the embodiments 1 to 7 for use in a treatment of a chronic or acute disease wherein said disease is septic shock or sepsis.
9. Adrenomedullin antibody or an adrenomedullin antibody fragment for use in a treatment of a chronic or acute disease according to any of the embodiments 1 to 8 wherein said antibody or fragment regulates the liquid balance of said patient.
10. Adrenomedullin antibody or an adrenomedullin antibody fragment for use in a treatment of a chronic or acute disease according to any of the embodiments 1 to 9 wherein said antibody or fragment used for prevention of organ dysfunction or organ failure.
11. Adrenomedullin antibody or an adrenomedullin antibody fragment for use in a treatment of a chronic or acute disease according to embodiments 10 wherein said antibody or fragment is used for prevention of kidney dysfunction or kidney failure.
12. Adrenomedullin (ADM) antibody or an adrenomedullin antibody fragment for use in a treatment of a chronic or acute disease in a patient according to embodiments 1 to 11 wherein said antibody or fragment is used for stabilizing the circulation.
13. ADM antibody or an adrenomedullin antibody fragment for use in a treatment of a chronic or acute disease in a patient according to embodiment 12 wherein said antibody or fragment reduces the catecholamine requirement of said patient.
14. ADM antibody or an adrenomedullin antibody fragment for use in a treatment of a chronic or acute disease in a patient according to any of embodiments 1 to 13 for the reduction of the mortality risk for said patient.

15. ADM antibody or an adrenomedullin antibody fragment for use in a treatment of a chronic or acute disease in a patient according to any of embodiments 1 to 14 wherein said antibody or fragment may be administered in a dose of at least 3 µg/Kg body weight.
16. Pharmaceutical composition comprising an antibody or fragment according to any of embodiments 1 to 15.

Further embodiments within the scope of the present invention are set out below:

1. Adrenomedullin antibody or an adrenomedullin antibody fragment or ADM non-Ig scaffold wherein said antibody or said fragment or scaffold is a non-neutralizing antibody.
2. Adrenomedullin antibody or an adrenomedullin antibody fragment or ADM non-Ig scaffold wherein said antibody or said fragment or scaffold is an ADM stabilizing antibody or fragment or scaffold that enhances the half life ($t_{1/2}$ half retention time) of adrenomedullin in serum, blood, plasma at least 10%, preferably at least 50%, more preferably >50%, most preferably 100% and/or wherein said antibody or fragment or scaffold blocks the bioactivity of ADM to less than 80%, preferably to less than 50%.
3. Adrenomedullin antibody or an adrenomedullin antibody fragment or ADM non-Ig scaffold wherein said antibody or said fragment is a modulating ADM antibody or fragment or scaffold that enhances the half life ($t_{1/2}$ half retention time) of adrenomedullin in serum, blood, plasma at least 10%, preferably at least, 50%, more preferably >50%, most preferably 100% and that blocks the bioactivity of ADM to less than 80%, preferably to less than 50%.
4. Adrenomedullin antibody or an adrenomedullin antibody fragment or ADM non-Ig scaffold according to embodiment 1 or 2, wherein said antibody or fragment or scaffold binds to the N-terminal part (aa 1-21) of adrenomedullin.
5. Adrenomedullin antibody or an adrenomedullin antibody fragment or ADM non-Ig scaffold wherein said antibody or said fragment or scaffold according to embodiment 3 binds to the N-terminal end of adrenomedullin.
6. Adrenomedullin antibody or an adrenomedullin antibody fragment ADM non-Ig scaffold according to any of embodiments 1 to 4, wherein said antibody or said fragment or said scaffold is an ADM stabilizing antibody or fragment that enhances the $t_{1/2}$ half retention time of adrenomedullin in serum, blood, plasma at least 10%, preferably at least, 50%, more preferably >50%, most preferably 100%.
7. Adrenomedullin antibody or an adrenomedullin antibody fragment or ADM non-Ig scaffold according to any of the embodiments 1 to 6 for use as an active pharmaceutical substance.
8. Adrenomedullin antibody or an adrenomedullin antibody fragment ADM non-Ig scaffold according to any of the embodiments 1 to 7 for use in a treatment of a chronic or acute disease or acute condition wherein said disease or condition is selected from the group comprising severe infections as e.g. meningitis, systemic inflammatory Response-Syndrome (SIRS) sepsis; other diseases as diabetes, cancer, acute and chronic vascular diseases as e.g. heart failure, myocardial infarction, stroke, atherosclerosis; shock as e.g. septic shock and organ dysfunction as e.g. kidney dysfunction, liver dysfunction, burnings, surgery, traumata.
9. Adrenomedullin antibody or an adrenomedullin antibody fragment or ADM non-Ig scaffold according to any of the embodiments 1 to 8 for use in a treatment of a chronic or acute disease or acute condition wherein said disease is septic shock or sepsis.
10. ADM antibody or an adrenomedullin antibody fragment according to any of embodiments 1 to 9, wherein said antibody or fragment is a human monoclonal antibody or fragment that binds to ADM or an antibody fragment thereof wherein the heavy chain comprises at least one of the sequences:

```
                                        SEQ ID NO: 1
            GYTFSRYW

SEQ ID NO: 2
            ILPGSGST

SEQ ID NO: 3
            TEGYEYDGFDY
```

And/or wherein the light chain comprises the at least one of the sequences

```
                                        SEQ ID NO: 4
            QSIVYSNGNTY

SEQ ID NO: 5
            RVS

SEQ ID NO: 6
            FQGSHIPYT.
```

11. A human monoclonal antibody or fragment that binds to ADM or an antibody fragment thereof according to embodiment 10 wherein said antibody or fragment comprises a sequence selected from the group comprising:

```
(AM-VH-C)
                                        SEQ ID NO: 7
QVQLQQSGAELMKPGASVKISCKATGYTFSRYWIEWVKQRPGHGLEWIGE

ILPGSGSTNYNEKFKGKATITADTSSNTAYMQLSSLTSEDSAVYYCTEGY

EYDGFDYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH1)
                                        SEQ ID NO: 8
QVQLVQSGAEVKKPGSSVKVSCKASGYTFSRYWISWVRQAPGQGLEWMGR

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH2-E40)
                                        SEQ ID NO: 9
QVQLVQSGAEVKKPGSSVKVSCKASGYTFSRYWIEWVRQAPGQGLEWMGR

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH
```

-continued (AM-VH3-T26-E55)
SEQ ID NO: 10
QVQLVQSGAEVKKPGSSVKVSCKATGYTFSRYWISWVRQAPGQGLEWMGE

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VH4-T26-E40-E55)
SEQ ID NO: 11
QVQLVQSGAEVKKPGSSVKVSCKATGYTFSRYWIEWVRQAPGQGLEWMGE

ILPGSGSTNYAQKFQGRVTITADESTSTAYMELSSLRSEDTAVYYCTEGY

EYDGFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKHHHHHH (AM-VL-C)
SEQ ID NO: 12
DVLLSQTPLSLPVSLGDQATISCRSSQSIVYSNGNTYLEWYLQKPGQSPK

LLIYRVSNRFSGVPDRFSGSGSGTDFTLKISRVEAEDLGVYYCFQGSHIP

YTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC (AM-VL1)
SEQ ID NO: 13
DVVMTQSPLSLPVTLGQPASISCRSSQSIVYSNGNTYLNWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC (AM-VL2-E40)
SEQ ID NO: 14
DVVMTQSPLSLPVTLGQPASISCRSSQSIVYSNGNTYLEWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

12. Adrenomedullin antibody or an adrenomedullin antibody fragment or ADM non-Ig scaffold according to any of the embodiments 1 to 11 for regulating the fluid balance in a patient having a chronic or acute disease or acute condition.
13. Adrenomedullin antibody or an adrenomedullin antibody fragment or ADM non-Ig scaffold according to any of the embodiments 1 to 11 for preventing or reducing organ dysfunction or organ failure in a patient having in a chronic or acute disease or acute condition.
14. Adrenomedullin antibody or an adrenomedullin antibody fragment or ADM non-Ig scaffold according to embodiment 10 wherein organ is kidney or liver.
15. Adrenomedullin (ADM) antibody or an adrenomedullin antibody fragment or ADM non-Ig scaffold according to embodiments 1 to 14 for stabilizing the circulation in a patient having a chronic or acute disease or acute condition.
16. ADM antibody or an adrenomedullin antibody fragment or ADM non-Ig scaffold for use in a treatment of a chronic or acute disease in a patient according to embodiment 15 wherein said antibody or fragment reduces the catecholamine requirement of said patient.
17. Adrenomedullin antibody or an adrenomedullin antibody fragment or ADM non-Ig scaffold according to any of the embodiments 1 to 16 to be used in combination with vasopressors e.g. catecholamine.
18. Adrenomedullin antibody or an adrenomedullin antibody fragment or ADM non-Ig scaffold according to any of the embodiments 1 to 17 to be used in combination with intravenous fluid administration.
19. Adrenomedullin antibody or an adrenomedullin antibody fragment or ADM non-Ig scaffold according to any of the embodiments 1 to 18 to be used in combination with an TNF-alpha-antibody.
20. ADM antibody or an adrenomedullin antibody fragment or non-Ig-scaffold according to any of embodiments 1 to 19 for use in a treatment of a patient in need thereof wherein said antibody or fragment may be administered in a dose of at least 3 µg/Kg body weight.
21. Pharmaceutical composition comprising an antibody or fragment or scaffold according to any of embodiments 1 to 20.
22. ADM antibody or an adrenomedullin antibody fragment or non-Ig-scaffold according to any of embodiments 1 to 20 for use in a treatment of a chronic or acute disease or chronic condition.
23. ADM antibody or an adrenomedullin antibody fragment or non-Ig-scaffold according to embodiment 22 wherein said disease is sepsis.

Further embodiments within the scope of the present invention are set out below:

1. Adrenomedullin ADM antibody or an adrenomedullin antibody fragment for use in therapy of a severe chronical or acute disease of a patient for the reduction of the mortality risk for said patient.
2. ADM antibody or an adrenomedullin antibody fragment according to embodiment 1 wherein the antibody format is selected from the group comprising Fv fragment, scFv fragment, Fab fragment, scFab fragment, (Fab)2 fragment and scFv-Fc Fusion protein.
3. ADM antibody or an adrenomedullin antibody fragment according embodiment 1 or 2 wherein said antibody or fragment binds to the N-terminal part (aa 1-21) of adrenomedullin.
4. ADM antibody or an adrenomedullin antibody fragment according to any of embodiments 1 to 3, wherein said antibody or fragment recognizes and binds to the N-terminal end (aa1) of adrenomedullin.
5. ADM antibody or an adrenomedullin antibody fragment according to any of embodiments 1 to 4, wherein said antibody or fragment is an ADM stabilizing antibody or fragment that enhances the t1/2 half retention time of adrenomedullin in serum, blood, plasma at least 10%, preferably at least, 50%, more preferably >50%, most preferably >100%.
6. ADM antibody or an adrenomedullin antibody fragment according to any of embodiments 1 to 5, wherein said antibody or fragment blocks the bioactivity of ADM to less than 80%, preferably less than 50%.
7. ADM antibody or an adrenomedullin antibody fragment for use in therapy of a chronical or acute disease of a patient according to any of embodiments 1 to 6 wherein said disease is selected from the group comprising sepsis, diabetis, cancer, heart failure, shock and kidney dysfunction.
8. ADM antibody or an adrenomedullin antibody fragment for use in therapy of a chronical or acute disease of a patient according to any of embodiments 1 to 7 wherein said patient is an ICU patient.
9. ADM antibody or an adrenomedullin antibody fragment for use in therapy of a chronical or acute disease of a patient according to any of embodiments 1 to 8 wherein the mortality risk is reduced by preventing adverse event wherein the latter are selected from the group comprising SIRS, sepsis, septic shock, organ failure, kidney failure, liquid dysbalance and low blood pressure.
10. ADM antibody or an adrenomedullin antibody fragment for use in therapy of a chronical or acute disease of a patient according to any of embodiments 1 to 8 wherein said antibody or fragment is to be used in combination of ADM binding protein.
11. Pharmaceutical formulation comprising an antibody or fragment according to any of embodiments 1 to 10.
12. Pharmaceutical formulation according to embodiment 11 wherein said pharmaceutical formulation is a solution, preferably a ready-to-use solution.
13. Pharmaceutical formulation according to embodiment 11 wherein said pharmaceutical formulation is in a freeze-dried state.
14. Pharmaceutical formulation according to any of embodiments 11 to 12, wherein said pharmaceutical formulation is administered intra-muscular.
15. Pharmaceutical formulation according to any of embodiments 11 to 12, wherein said pharmaceutical formulation is administered intra-vascular.
16. Pharmaceutical formulation according to embodiment 15, wherein said pharmaceutical formulation is administered via infusion.

Further embodiments within the scope of the present invention are set out below:
1. Adrenomedullin (ADM) antibody or an adrenomedullin antibody fragment or ADM non-Ig scaffold for use in therapy of a severe chronical or acute disease or acute condition of a patient for the reduction of the mortality risk for said patient wherein said antibody or fragment or scaffold is a non-neutralizing ADM antibody or a non-neutralizing adrenomedullin antibody fragment or a non-neutralizing ADM non-Ig scaffold.
2. ADM antibody or an adrenomedullin antibody fragment according to embodiment 1 wherein the antibody format is selected from the group comprising Fv fragment, scFv fragment, Fab fragment, scFab fragment, (Fab)2 fragment and scFv-Fc Fusion protein.
3. ADM antibody or an adrenomedullin antibody fragment or an ADM non-Ig scaffold according embodiment 1 or 2 wherein said antibody or fragment or scaffold binds to the N-terminal part (aa 1-21) of adrenomedullin.
4. ADM antibody or an adrenomedullin antibody fragment or an ADM non-Ig scaffold according to any of embodiments 1 to 3, wherein said antibody or fragment or scaffold recognizes and binds to the N-terminal end (aa 1) of adrenomedullin.
5. ADM antibody or an adrenomedullin antibody fragment or an ADM non-Ig scaffold according to any of embodiments 1 to 4, wherein said antibody or fragment or scaffold is an ADM stabilizing antibody or fragment or scaffold that enhances the half life (t1/2 half retention time) of adrenomedullin in serum, blood, plasma at least 10%, preferably at least, 50%, more preferably >50%, most preferably >100%.
6. ADM antibody or an adrenomedullin antibody fragment or an ADM non-Ig scaffold according to any of embodiments 1 to 5, wherein said antibody or fragment or scaffold blocks the bioactivity of ADM to less than 80%, preferably less than 50%.
7. ADM antibody or an adrenomedullin antibody fragment or an ADM non-Ig scaffold for use in therapy of a chronical or acute disease of a patient according to any of embodiments 1 to 6 wherein said disease is selected from the group comprising severe infections as e.g. meningitis, Systemic inflammatory Response-Syndrome (SIRS) sepsis; other diseases as diabetis, cancer, acute and chronic vascular diseases as e.g. heart failure, myocardial infarction, stroke, atherosclerosis; shock as e.g. septic shock and organ dysfunction as e.g. kidney dysfunction, liver dysfunction; burnings, surgery, traumata.
8. ADM antibody or an adrenomedullin antibody fragment or an ADM non-Ig scaffold for use in therapy of a chronical or acute disease of a patient according to any of embodiments 1 to 7 wherein said disease is selected from the group comprising SIRS, a severe infection, sepsis, shock e.g. septic shock.
9. ADM antibody or an adrenomedullin antibody fragment or an ADM non-Ig scaffold for use in therapy of a chronical or acute disease or acute condition of a patient according to any of embodiments 1 to 8 wherein said patient is an ICU patient. ADM antibody or an adrenomedullin antibody fragment or an ADM non-Ig scaffold for use in therapy of a chronical or acute disease or acute condition of a patient according to any of embodiments 1 to 9 wherein the mortality risk is reduced by preventing an adverse event wherein the latter are selected from the group comprising SIRS, sepsis, shock as e.g. septic shock, acute and chronic vascular diseases as e.g. acute heart failure, myocardial infarction, stroke; organ failure as e.g, kidney failure, liver failure, fluid dysbalance and low blood pressure.
10. ADM antibody or an adrenomedullin antibody fragment according to any of embodiments 1 to 9, wherein said antibody or fragment is a human monoclonal antibody or fragment that binds to ADM or an antibody fragment thereof wherein the heavy chain comprises the sequences

```
                            SEQ ID NO: 1
        GYTFSRYW

SEQ ID NO: 2
        ILPGSGST

SEQ ID NO: 3
        TEGYEYDGFDY
``` and wherein the light chain comprises the sequences

```
                            SEQ ID NO: 4
        QSIVYSNGNTY

SEQ ID NO: 5
        RVS

SEQ ID NO: 6
        FQGSHIPYT.
```

12. A human monoclonal antibody or fragment that binds to ADM or an antibody fragment thereof according to embodiment 10 wherein said antibody or fragment comprises a sequence selected from the group comprising:

(AM-VH-C)
SEQ ID NO: 7
QVQLQQSGAELMKPGASVKISCKATGYTFSRYWIEWVKQRPGHGLEWIGE
ILPGSGSTNYNEKFKGKATITADTSSNTAYMQLSSLTSEDSAVYYCTEGY
EYDGFDYWGQGTTLTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH1)
SEQ ID NO: 8
QVQLVQSGAEVKKPGSSVKVSCKASGYTFSRYWISWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH2-E40)
SEQ ID NO: 9
QVQLVQSGAEVKKPGSSVKVSCKASGYTFSRYWIEWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH3-T26-E55)
SEQ ID NO: 10
QVQLVQSGAEVKKPGSSVKVSCKATGYTFSRYWISWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH4-T26-E40-E55)
SEQ ID NO: 11
QVQLVQSGAEVKKPGSSVKVSCKATGYTFSRYWIEWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VL-C)
SEQ ID NO: 12
DVLLSQTPLSLPVSLGDQATISCRSSQSIVYSNGNTYLEWYLQKPGQSPK
LLIYRVSNRFSGVPDRFSGSGSGTDFTLKISRVEAEDLGVYYCFQGSHIP
YTFGGGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC (AM-VL1)
SEQ ID NO: 13
DVVMTQSPLSLPVTLGQPASISCRSSQSIVYSNGNTYLNWFQQRPGQSPR
RLIYRVSNRDSGVPDRFSGSGSGTDFTLKISRVEAEDVGVYYCFQGSHIP
YTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC (AM-VL2-E40)
SEQ ID NO: 14
DVVMTQSPLSLPVTLGQPASISCRSSQSIVYSNGNTYLEWFQQRPGQSPR
RLIYRVSNRDSGVPDRFSGSGSGTDFTLKISRVEAEDVGVYYCFQGSHIP
YTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

13. ADM antibody or an adrenomedullin antibody fragment or ADM non-IG scaffold for use in therapy of a chronic or acute disease of a patient according to any of the embodiments 1 to 12 to be used in combination with vasopressors e.g. catecholamine and/or fluids administered intravenously.

14. ADM antibody or adrenomedullin antibody fragment or ADM non-IG scaffold for use in therapy of a chronic or acute disease of a patient according to any of the embodiments 1 to 13 or a combination according to embodiment 10 to be used in combination with ADM binding protein and/or further active ingredients.

15. Pharmaceutical formulation comprising an antibody or fragment or scaffold according to any of embodiments 1 to 14.

16. Pharmaceutical formulation according to embodiment 15 wherein said pharmaceutical formulation is a solution, preferably a ready-to-use solution.

17. Pharmaceutical formulation according to embodiment 15 wherein said pharmaceutical formulation is in a freeze-dried state.

18. Pharmaceutical formulation according to any of embodiments 15 to 16, wherein said pharmaceutical formulation is administered intra-muscular.

19. Pharmaceutical formulation according to any of embodiments 15 to 16, wherein said pharmaceutical formulation is administered intra-vascular.

20. Pharmaceutical formulation according to embodiment 19, wherein said pharmaceutical formulation is administered via infusion.

21. ADM antibody or an Adrenomedullin antibody fragment or AM non-Ig scaffold, wherein said antibody or fragment or scaffold binds to the N-terminal part (aa 1-21) of Adrenomedullin in, preferably human ADM.

22. Antibody or fragment or scaffold according to embodiment 2, wherein said antibody or fragment or scaffold recognizes and binds to the N-terminal end (aa 1) of Adrenomedullin.

Further embodiments within the scope of the present invention are set out below:

1. Adrenomedullin (ADM) antibody or an adrenomedullin antibody fragment for use in therapy of a chronical or acute disease of a patient for prevention of organ dysfunction or organ failure.

2. ADM antibody or an adrenomedullin antibody fragment for use in therapy of a chronical or acute disease according to embodiment 1 wherein said organ is kidney.

3. ADM antibody or an adrenomedullin antibody fragment according to embodiment 1 wherein the antibody format is selected from the group comprising Fv fragment, scFv fragment, Fab fragment, scFab fragment, (Fab)2 fragment and scFv-Fc Fusion protein.
4. ADM antibody or an adrenomedullin antibody fragment according any of embodiment 1 to 3 wherein said antibody or fragment binds to the N-terminal part (aa 1-21) of adrenomedullin.
5. ADM antibody or an adrenomedullin antibody fragment according to any of embodiments 1 to 4, wherein said antibody or fragment recognizes and binds to the N-terminal end (aa1) of adrenomedullin.
6. ADM antibody or an adrenomedullin antibody fragment according to any of embodiments 1 to 5, wherein said antibody or said fragment is an ADM stabilizing antibody or fragment that enhances the t1/2 half retention time of adrenomedullin in serum, blood, plasma at least 10%, preferably at least 50%, more preferably >50%, most preferably >100%.
7. ADM antibody or an adrenomedullin antibody fragment according to any of embodiments 1 to 6, wherein said antibody blocks the bioactivity of ADM to less than 80%, preferably less than 50%.
8. ADM antibody or an adrenomedullin antibody fragment for use in therapy of a chronical or acute disease of a patient according to any of embodiments 1 to 7 wherein said disease is selected from the group comprising sepsis, diabetis, cancer, heart failure, and shock.
9. ADM antibody or an adrenomedullin antibody fragment for use in therapy of a chronical or acute disease of a patient according to any of embodiments 1 to 8 wherein said patient is an ICU patient.
10. ADM antibody or an adrenomedullin antibody fragment for use in therapy of a chronical or acute disease of a patient according to any of embodiments 1 to 9 wherein said antibody or fragment is a modulating antibody or fragment that enhances the t1/2 half retention time of adrenomedullin in serum, blood, plasma at least 10%, preferably at least 50%, more preferably >50%, most preferably >100% and that blocks the bioactivity of ADM to less than 80%, preferably less than 50%.
11. Pharmaceutical formulation comprising an antibody or fragment according to any of embodiments 1 to 10.
12. Pharmaceutical formulation according to embodiment 11 wherein said pharmaceutical formulation is a solution, preferably a ready-to-use solution.
13. Pharmaceutical formulation according to embodiment 11 wherein said pharmaceutical formulation is in a freeze-dried state.
14. Pharmaceutical formulation according to any of embodiment 11 to 12, wherein said pharmaceutical formulation is administered intra-muscular.
15. Pharmaceutical formulation according to any of embodiment 11 to 12, wherein said pharmaceutical formulation is administered intra-vascular.
16. Pharmaceutical formulation according to embodiment 15, wherein said pharmaceutical formulation is administered via infusion.

Further embodiments within the scope of the present invention are set out below:
1. Adrenomedullin (ADM) antibody or an adrenomedullin antibody fragment or ADM non-Ig scaffold for use in therapy of a chronical or acute disease or acute condition of a patient for prevention or reduction of organ dysfunction or prevention of organ failure in said patient.
2. ADM antibody or an adrenomedullin antibody fragment or ADM non-Ig scaffold for use in therapy of a chronical or acute disease or acute disease according to embodiment 1 wherein said organ is kidney or liver.
3. ADM antibody or an adrenomedullin antibody fragment or ADM non-IG scaffold according to embodiment 1 or 2 wherein said ADM antibody or an adrenomedullin antibody fragment or ADM non-IG scaffold is a non-neutralizing ADM antibody or a non-neutralizing adrenomedullin antibody fragment or a non-neutralizing ADM non-IG scaffold
4. ADM antibody or an adrenomedullin antibody fragment or ADM non-IG scaffold according to any of embodiments 1 or 3 wherein the antibody format is selected from the group comprising Fv fragment, scFv fragment, Fab fragment, scFab fragment, (Fab)2 fragment and scFv-Fc Fusion protein.
5. ADM antibody or an adrenomedullin antibody fragment or ADM non-IG scaffold according any of embodiments 1 to 4 wherein said antibody or fragment or scaffold binds to the N-terminal part (aa 1-21) of adrenomedullin.
6. ADM antibody or an adrenomedullin antibody fragment or ADM non-IG scaffold according to any of embodiments 1 to 5, wherein said antibody or fragment or scaffold recognizes and binds to the N-terminal end (aa1) of adrenomedullin.
7. ADM antibody or an adrenomedullin antibody fragment or ADM non-IG scaffold according to any of embodiments 1 to 6, wherein said antibody or said fragment or scaffold is an ADM stabilizing antibody or fragment or scaffold that enhances the half life (t1/2 half retention time) of adrenomedullin in serum, blood, plasma at least 10%, preferably at least 50%, more preferably >50%, most preferably >100%.
8. ADM antibody or an adrenomedullin antibody fragment or ADM non-IG scaffold according to any of embodiments 1 to 7, wherein said antibody or fragment or scaffold blocks the bioactivity of ADM to less than 80%, preferably less than 50%.
9. ADM antibody or an adrenomedullin antibody fragment or ADM non-IG scaffold for use in therapy of a chronical or acute disease or acute condition of a patient according to any of embodiments 1 to 8 wherein said disease is selected from the group comprising sepsis, diabetis, cancer, heart failure, and shock.
10. ADM antibody or an adrenomedullin antibody fragment according to any of embodiments 1 to 9, wherein said antibody or fragment is a human monoclonal antibody or fragment that binds to ADM or an antibody fragment thereof wherein the heavy chain comprises the sequences

```
                                          SEQ ID NO: 1
         GYTFSRYW

SEQ ID NO: 2
         ILPGSGST

SEQ ID NO: 3
         TEGYEYDGFDY
``` and wherein the light chain comprises the sequences

```
                                          SEQ ID NO: 4
         QSIVYSNGNTY

SEQ ID NO: 5
         RVS

SEQ ID NO: 6
         FQGSHIPYT.
```

11. A human monoclonal antibody or fragment that binds to ADM or an antibody fragment thereof according to embodiments 10 wherein said antibody or fragment comprises a sequence selected from the group comprising:

(AM-VH-C)
SEQ ID NO: 7
QVQLQQSGAELMKPGASVKISCKATGYTFSRYWIEWVKQRPGHGLEWIGE
ILPGSGSTNYNEKFKGKATITADTSSNTAYMQLSSLTSEDSAVYYCTEGY
EYDGFDYWGQGTTLTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH1)
SEQ ID NO: 8
QVQLVQSGAEVKKPGSSVKVSCKASGYTFSRYWISWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH2-E40)
SEQ ID NO: 9
QVQLVQSGAEVKKPGSSVKVSCKASGYTFSRYWIEWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CCNVNHKPSNTKVDKRVEPKHHHHHH (AM-VH3-T26-E55)
SEQ ID NO: 10
QVQLVQSGAEVKKPGSSVKVSCKATGYTFSRYWISWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VH4-T26-E40-E55)
SEQ ID NO: 11
QVQLVQSGAEVKKPGSSVKVSCKATGYTFSRYWIEWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH (AM-VL-C)
SEQ ID NO: 12
DVLLSQTPLSLPVSLGDQATISCRSSQSIVYSNGNTYLEWYLQKPGQSPK
LLIYRVSNRFSGVPDRFSGSGSGTDFTLKISRVEAEDLGVYYCFQGSHIP
YTFGGGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC (AM-VL1)
SEQ ID NO: 13
DVVMTQSPLSLPVTLGQPASISCRSSQSIVYSNGNTYLNWFQQRPGQSPR
RLIYRVSNRDSGVPDRFSGSGSGTDFTLKISRVEAEDVGVYYCFQGSHIP
YTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC (AM-VL2-E40)
SEQ ID NO: 14
DVVMTQSPLSLPVTLGQPASISCRSSQSIVYSNGNTYLEWFQQRPGQSPR
RLIYRVSNRDSGVPDRFSGSGSGTDFTLKISRVEAEDVGVYYCFQGSHIP
YTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

12. ADM antibody or an adrenomedullin antibody fragment or ADM non-IG scaffold for use in therapy of a chronical or acute disease of a patient according to any of embodiments 1 to 11 wherein said antibody or fragment or scaffold is a modulating antibody or fragment or scaffold that enhances the half life (t1/2 half retention time) of adrenomedullin in serum, blood, plasma at least 10%, preferably at least 50%, more preferably >50%, most preferably >100% and that blocks the bioactivity of ADM to less than 80%, preferably less than 50%.

13. ADM antibody or an adrenomedullin antibody fragment or ADM non-IG scaffold for use in therapy of a chronic or acute disease or acute condition of a patient according to any of the embodiments 1 to 12 to be used in combination with vasopressors e.g. catecholamine and/or fluids administered intravenously.

14. ADM antibody or adrenomedullin antibody fragment or ADM non-IG scaffold for use in therapy of a chronic or acute disease or acute condition of a patient according to any of the embodiments 1 to 13 or a combination according to embodiment 13 to be used in combination with ADM binding protein and/or further active ingredients.

15. Pharmaceutical formulation comprising an antibody or fragment according to any of embodiments 1 to 13.

16. Pharmaceutical formulation according to embodiment 14 wherein said pharmaceutical formulation is a solution, preferably a ready-to-use solution.

17. Pharmaceutical formulation according to embodiment 14 wherein said pharmaceutical formulation is in a freeze-dried state.

18. Pharmaceutical formulation according to any of embodiments 14 to 15, wherein said pharmaceutical formulation is administered intra-muscular.

19. Pharmaceutical formulation according to any of embodiments 14 to 15, wherein said pharmaceutical formulation is administered intra-vascular.

20. Pharmaceutical formulation according to embodiment 18, wherein said pharmaceutical formulation is administered via infusion.

EXAMPLES

It should be emphasized that the antibodies, antibody fragments and non-Ig scaffolds of the example portion in accordance with the invention are binding to ADM, and thus should be considered as anti-ADM antibodies/antibody fragments/non-Ig scaffolds.

Example 1

Generation of Antibodies and Determination of their Affinity Constants

Several human and murine antibodies were produced and their affinity constants were determined (see tables 1 and 2).

Peptides/Conjugates for Immunization:

Peptides for immunization were synthesized, see Table 1, (JPT Technologies, Berlin, Germany) with an additional N-terminal Cystein (if no Cystein is present within the selected ADM-sequence) residue for conjugation of the peptides to Bovine Serum Albumin (BSA). The peptides were covalently linked to BSA by using Sulfolink-coupling gel (Perbio-science, Bonn, Germany). The coupling procedure was performed according to the manual of Perbio.

The murine antibodies were generated according to the following method:

A Balb/c mouse was immunized with 100 μg Peptide-BSA-Conjugate at day 0 and 14 (emulsified in 1000 complete Freund's adjuvant) and 50 μg at day 21 and 28 (in 1000 incomplete Freund's adjuvant). Three days before the fusion experiment was performed, the animal received 50 μg of the conjugate dissolved in 1000 saline, given as one intraperitoneal and one intra-venous injection.

Spenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined.

(see also Lane, R. D. "A short-duration polyethylene glycol fusion technique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Mouse Monoclonal Antibody Production:

Antibodies were produced via standard antibody production methods (Marx et al, Monoclonal Antibody Production, ATLA 25, 121, 1997) and purified via Protein A. The antibody purities were >95% based on SDS gel electrophoresis analysis.

Human Antibodies

Human Antibodies were produced by means of phage display according to the following procedure:

The human naive antibody gene libraries HALT/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust, M., Meyer, T., Voedisch, B., Rülker, T., Thie, H., El-Ghezal, A., Kirsch, M. I., Schütte, M., Helmsing, S., Meier, D., Schirrmann, T., Dübel, S., 2011. A human scFv antibody generation pipeline for proteome research. Journal of Biotechnology 152, 159-170; Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of *Aspergillus fumigatus*. PLoS One 4, e6625).

Positive clones have been selected based on positive ELISA signal for antigen and negative for streptavidin coated micro titer plates. For further characterizations the scFv open reading frame has been cloned into the expression plasmid pOPE107 (Hust et al., J. Biotechn. 2011), captured from the culture supernatant via immobilised metal ion affinity chromatography and purified by a size exclusion chromatography.

Affinity Constants

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (Lorenz et al., "Functional Antibodies Targeting IsaA of *Staphylococcus aureus* Augment Host Immune Response and Open New Perspectives for Antibacterial Therapy"; Antimicrob Agents Chemother. 2011 January; 55(1): 165-173.)

The monoclonal antibodies were raised against the below depicted ADM regions of human and murine ADM, respectively. The following table represents a selection of obtained antibodies used in further experiments. Selection was based on target region:

TABLE 1

| Sequence Number | Antigen/Immunogen | ADM Region | Designation | Affinity constants Kd (M) |
|---|---|---|---|---|
| SEQ ID: 15 | YRQSMNNFQGLRSFGCRFGTC | 1-21 | NT-H | $5.9 \times 10^{-9}$ |
| SEQ ID: 16 | CTVQKLAHQIYQ | 21-32 | MR-H | $2 \times 10^{-9}$ |

TABLE 1-continued

| Sequence Number | Antigen/Immunogen | ADM Region | Designation | Affinity constants Kd (M) |
|---|---|---|---|---|
| SEQ ID: 17 | CAPRSKISPQGY-NH2 | C-42-52 | CT-H | $1.1 \times 10^{-9}$ |
| SEQ ID: 18 | YRQSMNQGSRSNGCRFGTC | 1-19 | NT-M | $3.9 \times 10^{-9}$ |
| SEQ ID: 19 | CTFQKLAHQIYQ | 19-31 | MR-M | $4.5 \times 10^{-10}$ |
| SEQ ID: 20 | CAPRNKISPQGY-NH2 | C-40-50 | CT-M | $9 \times 10^{-9}$ |

The following is a list of further obtained monoclonal antibodies:
List of Anti-ADM-Antibodies

TABLE 2

| Target | Source | Klone number | Affinity (M) | max inhibition bioassay (%) (see example 2) |
|---|---|---|---|---|
| NT-M | Mouse | ADM/63 | $5.8 \times 10^{-9}$ | 45 |
| | Mouse | ADM/364 | $2.2 \times 10^{-8}$ | 48 |
| | Mouse | ADM/365 | $3.0 \times 10^{-8}$ | |
| | Mouse | ADM/366 | $1.7 \times 10^{-8}$ | |
| | Mouse | ADM/367 | $1.3 \times 10^{-8}$ | |
| | Mouse | ADM/368 | $1.9 \times 10^{-8}$ | |
| | Mouse | ADM/369 | $2.0 \times 10^{-8}$ | |
| | Mouse | ADM/370 | $1.6 \times 10^{-8}$ | |
| | Mouse | ADM/371 | $2.0 \times 10^{-8}$ | |
| | Mouse | ADM/372 | $2.5 \times 10^{-8}$ | |
| | Mouse | ADM/373 | $1.8 \times 10^{-8}$ | |
| | Mouse | ADM/377 | $1.5 \times 10^{-8}$ | |
| | Mouse | ADM/378 | $2.2 \times 10^{-8}$ | |
| | Mouse | ADM/379 | $1.6 \times 10^{-8}$ | |
| | Mouse | ADM/380 | $1.8 \times 10^{-8}$ | |
| | Mouse | ADM/381 | $2.4 \times 10^{-8}$ | |
| | Mouse | ADM/382 | $1.6 \times 10^{-8}$ | |
| | Mouse | ADM/383 | $1.8 \times 10^{-8}$ | |
| | Mouse | ADM/384 | $1.7 \times 10^{-8}$ | |
| | Mouse | ADM/385 | $1.7 \times 10^{-8}$ | |
| | Mouse | ADM/403 | $1.2 \times 10^{-8}$ | |
| | Mouse | ADM/395 | $1.2 \times 10^{-8}$ | |
| | Mouse | ADM/396 | $3.0 \times 10^{-8}$ | |
| | Mouse | ADM/397 | $1.5 \times 10^{-8}$ | |
| MR-M | Mouse | ADM/38 | $4.5 \times 10^{-10}$ | 68 |
| MR-M | Mouse | ADM/39 | $5.9 \times 10^{-9}$ | 72 |
| CT-M | Mouse | ADM/65 | $9.0 \times 10^{-9}$ | 100 |
| CT-M | Mouse | ADM/66 | $1.6 \times 10^{-8}$ | 100 |
| NT-H | Mouse | ADM/33 | $5.9 \times 10^{-8}$ | 38 |
| NT-H | Mouse | ADM/34 | $1.6 \times 10^{-8}$ | 22 |
| MR-H | Mouse | ADM/41 | $1.2 \times 10^{-8}$ | 67 |
| MR-H | Mouse | ADM/42 | $<1 \times 10^{-8}$ | |
| MR-H | Mouse | ADM/43 | $2.0 \times 10^{-9}$ | 73 |
| MR-H | Mouse | ADM/44 | $<1 \times 10^{-8}$ | |
| CT-H | Mouse | ADM/15 | $<1 \times 10^{-8}$ | |
| CT-H | Mouse | ADM/16 | $1.1 \times 10^{-9}$ | 100 |
| CT-H | Mouse | ADM/17 | $3.7 \times 10^{-9}$ | 100 |
| CT-H | Mouse | ADM/18 | $<1 \times 10^{-8}$ | |
| hADM | Phage display | ADM/A7 | $<1 \times 10^{-8}$ | |
| | Phage display | ADM/B7 | $<1 \times 10^{-8}$ | |
| | Phage display | ADM/C7 | $<1 \times 10^{-8}$ | |
| | Phage display | ADM/G3 | $<1 \times 10^{-8}$ | |
| | Phage display | ADM/B6 | $<1 \times 10^{-8}$ | |
| | Phage display | ADM/B11 | $<1 \times 10^{-8}$ | |
| | Phage display | ADM/D8 | $<1 \times 10^{-8}$ | |
| | Phage display | ADM/D11 | $<1 \times 10^{-8}$ | |
| | Phage display | ADM/G12 | $<1 \times 10^{-8}$ | |

Generation of Antibody Fragments by Enzymatic Digestion:

The generation of Fab and F(ab)$_2$ fragments was done by enzymatic digestion of the murine full length antibody NT-M. Antibody NT-M was digested using a) the pepsin-based F(ab)$_2$ Preparation Kit (Pierce 44988) and b) the papain-based Fab Preparation Kit (Pierce 44985). The fragmentation procedures were performed according to the instructions provided by the supplier. Digestion was carried out in case of F(ab)$_2$-fragmentation for 8 h at 37° C. The Fab-fragmentation digestion was carried out for 16 h, respectively.

Procedure for Fab Generation and Purification:

The immobilized papain was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated Immobilized Papain. Incubation time of the digestion reaction was done for 16 h on a tabletop rocker at 37° C. The column was centrifuged at 5000×g for 1 minute to separate digest from the Immobilized Papain. Afterwards the resin was washed with 0.5 ml PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 ml of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments.

(References: Coulter, A. and Harris, R. (1983). J. Immunol. Meth. 59, 199-203; Lindner I. et al. (2010) {alpha}2-Macroglobulin inhibits the malignant properties of astrocytoma cells by impeding {beta}-catenin signaling. Cancer Res. 70, 277-87; Kaufmann B. et al. (2010) Neutralization of West Nile virus by cross-linking of its surface proteins with Fab fragments of the human monoclonal antibody CR4354. PNAS. 107, 18950-5; Chen X. et al. (2010) Requirement of open headpiece conformation for activation of leukocyte integrin αxβ2. PNAS. 107, 14727-32; Uysal H. et al. (2009) Structure and pathogenicity of antibodies specific for citrullinated collagen type II in experimental arthritis. J. Exp. Med. 206, 449-62; Thomas G. M. et al. (2009) Cancer cell-derived microparticles bearing P-selectin glycoprotein ligand 1 accelerate thrombus formation in vivo. J. Exp. Med. 206, 1913-27; Kong F. et al. (2009) Demonstration of catch bonds between an integrin and its ligand. J. Cell Biol. 185, 1275-84.)

Procedure for Generation and Purification of F(ab')$_2$ Fragments:

The immobilized Pepsin was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated Immobilized Pepsin. Incubation time of the digestion reaction was done for 16 h on a tabletop rocker at 37° C. The column was centrifuged at 5000×g for 1 minute to separate digest from the Immobilized Papain. Afterwards the resin was washed with 0.5 mL PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 mL of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments.

(References: Mariani, M., et al. (1991). A new enzymatic method to obtain high-yield F(ab')2 suitable for clinical use from mouse IgG1. Mol. Immunol. 28: 69-77; Beale, D. (1987). Molecular fragmentation: Some applications in immunology. Exp Comp Immunol 11:287-96; Ellerson, J. R., et al. (1972). A fragment corresponding to the CH2 region of immunoglobulin G (IgG) with complement fixing activity. FEBS Letters 24(3):318-22; Kerbel, R. S. and Elliot, B. E. (1983). Detection of Fc receptors. Meth Enzymol 93:113-147; Kulkarni, P. N., et al. (1985). Conjugation of methotrexate to IgG antibodies and their F(ab')2 fragments and the effect of conjugated methotrexate on tumor growth in vivo. Cancer Immunol Immunotherapy 19:211-4; Lamoyi, E. (1986). Preparation of F(ab')2 Fragments from mouse IgG of various subclasses. Meth Enzymol 121:652-663; Parham, P., et al. (1982). Monoclonal antibodies: purification, fragmentation and application to structural and functional studies of class I MHC antigens. J Immunol Meth 53:133-73; Raychaudhuri, G., et al. (1985). Human IgG1 and its Fc fragment bind with different affinities to the Fc receptors on the human U937, HL-60 and ML-1 cell lines. Mol Immunol 22(9):1009-19; Rousseaux, J., et al. (1980). The differential enzyme sensitivity of rat immunoglobulin G subclasses to papain an pepsin. Mol Immunol 17:469-82; Rousseaux, J., et al. (1983). Optimal condition for the preparation of Fab and F(ab')2 fragments from monoclonal IgG of different rat IgG subclasses. J Immunol Meth 64:141-6; Wilson, K. M., et al. (1991). Rapid whole blood assay for HIV-1 seropositivity using an Fab-peptide conjugate. J Immunol Meth 138:111-9.)

NT-H-Antibody Fragment Humanization

The antibody fragment was humanized by the CDR-grafting method (Jones, P. T., Dear, P. H., Foote, J., Neuberger, M. S., and Winter, G. (1986) Replacing the complementarity-determining regions in a human antibody with those from a mouse. Nature 321, 522-525).

The Following Steps where Done to Achieve the Humanized Sequence:

Total RNA extraction: Total RNA was extracted from NT-H hybridomas using the Qiagen kit.

First-round RT-PCR: QIAGEN® OneStep RT-PCR Kit (Cat No. 210210) was used. RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers.

Reaction Setup: 5× QIAGEN® OneStep RT-PCR Buffer 5.0 µl, dNTP Mix (containing 10 mM of each dNTP) 0.8 µl, Primer set 0.5 µl, QIAGEN® OneStep RT-PCR Enzyme Mix 0.8 µl, Template RNA 2.0 µl, RNase-free water to 20.0 µl, Total volume 20.0 µl PCR condition: Reverse transcription: 50° C., 30 min; Initial PCR activation: 95° C., 15 min Cycling: 20 cycles of 94° C., 25 sec; 54° C., 30 sec; 72° C., 30 sec; Final extension: 72° C., 10 min Second-round semi-nested PCR: The RT-PCR products from the first-round reactions were further amplified in the second-round PCR. 12 individual heavy chain and 11 light chain RT-PCR reactions were set up using semi-nested primer sets specific for antibody variable regions.

Reaction Setup: 2×PCR mix 10 µl; Primer set 2 µl; First-round PCR product 8 µl; Total volume 20 µl; Hybridoma Antibody Cloning Report PCR condition: Initial denaturing of 5 min at 95° C.; 25 cycles of 95° C. for 25 sec, 57° C. for 30 sec, 68° C. for 30 sec; Final extension is 10 min 68° C.

After PCR is finished, run PCR reaction samples onto agarose gel to visualize DNA fragments amplified. After sequencing more than 15 cloned DNA fragments amplified by nested RT-PCR, several mouse antibody heavy and light chains have been cloned and appear correct. Protein sequence alignment and CDR analysis identifies one heavy chain and one light chain. After alignment with homologous human framework sequences the resulting humanized sequence for the variable heavy chain is the following: see FIG. 6 (As the amino acids on positions 26, 40 and 55 in the variable heavy chain and amino acid on position 40 in the variable light are critical to the binding properties, they may be reverted to the murine original. The resulting candidates are depicted below) (Padlan, E. A. (1991) A possible procedure for reducing the immunogenicity of antibody variable domains while preserving their ligand-binding properties. Mol. Immunol. 28, 489-498; Harris, L. and Bajorath, J. (1995) Profiles for the analysis of immunoglobulin sequences: Comparison of V gene subgroups. Protein Sci. 4, 306-310).

Annotation for the antibody fragment sequences (SEQ ID NO: 7-14): bold and underline are the CDR 1, 2, 3 in chronologically arranged; italic are constant regions; hinge regions are highlighted with bold letters and the histidine tag with bold and italic letters; framework point mutation have a grey letter-background.

(AM-VH-C)

SEQ ID NO: 7

QVQLQQSGAELMKPGASVKISCKATGYTFSRYWIEWVKQRPGHGLEWIGEILPG
SGSTNYNEKFKGKATITADTS*SNTAYMQLSSLTSEDSAVYYC*TEGYEYDGFDY*WGQ*
*GTTLTVSSASTKGPSVFPLAPSSKSTSGGTAALGCLVKDYFPEPVTVSWNSGALTSGVHT*
*FPAVLQSSGLYSLSSVVTVPSSSLGTQTYICNVNHKPSNTKVDKRV*EPKHHHHHH

(AM-VH1)

SEQ ID NO: 8

QVQLVQSGAEVKKPGSSVKVSCKASGYTFSRYWISWVRQAPGQGLEWMGRILP
GSGSTNYAQKFQGRVTITADE*STSTAYMELSSLRSEDTAVYYC*TEGYEYDGFDY*WGQ*
*GTTVTVSSASTKGPSVFPLAPSSKSTSGGTAALGCLVKDYFPEPVTVSWNSGALTSGVHT*
*FPAVLQSSGLYSLSSVVTVPSSSLGTQTYICNVNHKPSNTKVDKRV*EPKHHHHHH

(AM-VH2-E40)

SEQ ID NO: 9

QVQLVQSGAEVKKPGSSVKVSCKASGYTFSRYWIEWVRQAPGQGLEWMGRILP
GSGSTNYAQKFQGRVTITADE*STSTAYMELSSLRSEDTAVYYC*TEGYEYDGFDY*WGQ*
*GTTVTVSSASTKGPSVFPLAPSSKSTSGGTAALGCLVKDYFPEPVTVSWNSGALTSGVHT*
*FPAVLQSSGLYSLSSVVTVPSSSLGTQTYICNVNHKPSNTKVDKRV*EPKHHHHHH

(AM-VH3-T26-E55)

SEQ ID NO: 10

QVQLVQSGAEVKKPGSSVKVSCKATGYTFSRYWISWVRQAPGQGLEWMGEILP
GSGSTNYAQKFQGRVTITADE*STSTAYMELSSLRSEDTAVYYC*TEGYEYDGFDY*WGQ*
*GTTVTVSSASTKGPSVFPLAPSSKSTSGGTAALGCLVKDYFPEPVTVSWNSGALTSGVHT*
*FPAVLQSSGLYSLSSVVTVPSSSLGTQTYICNVNHKPSNTKVDKRV*EPKHHHHHH

(AM-VH4-T26-E40-E55)

SEQ ID NO: 11

QVQLVQSGAEVKKPGSSVKVSCKATGYTFSRYWIEWVRQAPGQGLEWMGEILP
GSGSTNYAQKFQGRVTITADE*STSTAYMELSSLRSEDTAVYYC*TEGYEYDGFDY*WGQ*
*GTTVTVSSASTKGPSVFPLAPSSKSTSGGTAALGCLVKDYFPEPVTVSWNSGALTSGVHT*
*FPAVLQSSGLYSLSSVVTVPSSSLGTQTYICNVNHKPSNTKVDKRV*EPKHHHHHH

(AM-VL-C)

SEQ ID NO: 12

DVLLSQTPLSLPVSLGDQATISCRSSQSIVYSNGNTYLEWYLQKPGQSPKLLIYRV
SNRFSGVPDRFSGSGSGTDFTLKISRVEAEDLGVYYCFQGSHIPYTFGGGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (AM-VL1)

SEQ ID NO: 13

DVVMTQSPLSLPVTLGQPASISCRSSQSIVYSNGNTYLNWFQQRPGQSPRRLIYRV
SNRDSGVPDRFSGSGSGTDFTLKISRVEAEDVGVYYCFQGSHIPYTFGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (AM-VL2-E40)

SEQ ID NO: 14

DVVMTQSPLSLPVTLGQPASISCRSSQSIVYSNGNTYLEWFQQRPGQSPRRLIYRV
SNRDSGVPDRFSGSGSGTDFTLKISRVEAEDVGVYYCFQGSHIPYTFGQGTKLEIK

-continued

RTVAAPSVFIFPPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

Example 2

Effect of Selected Anti-ADM-Antibodies on Anti-ADM-Bioactivity

The effect of selected ADM-antibodies on ADM-bioactivity was tested in an human recombinant Adrenomedullin receptor cAMP functional assay (Adrenomedullin Bioassay).

Testing of Antibodies Targeting Human or Mouse Adrenomedullin in Human Recombinant Adrenomedullin Receptor cAMP Functional Assay (Adrenomedullin Bioassay)

Materials:

Cell line: CHO-K1

Receptor: Adrenomedullin (CRLR+RAMP3)

Receptor Accession Number Cell line: CRLR: U17473; RAMP3: AJ001016

CHO-K1 cells expressing human recombinant adrenomedullin receptor (FAST-027C) grown prior to the test in media without antibiotic were detached by gentle flushing with PBS-EDTA (5 mM EDTA), recovered by centrifugation and resuspended in assay buffer (KRH: 5 mM KCl, 1.25 mM MgSO4, 124 mM NaCl, 25 mM HEPES, 13.3 mM Glucose, 1.25 mM KH2PO4, 1.45 mM CaCl2, 0.5 g/l BSA).

Dose response curves were performed in parallel with the reference agonists (hADM or mADM).

Antagonist test (96 well):

For antagonist testing, 6 µl of the reference agonist (human (5.63 nM) or mouse (0.67 nM) adrenomedullin) was mixed with 6 µl of the test samples at different antagonist dilutions; or with 6 µl buffer. After incubation for 60 min at room temperature, 12 µl of cells (2,500 cells/well) were added. The plates were incubated for 30 min at room temperature. After addition of the lysis buffer, percentage of DeltaF will be estimated, according to the manufacturer specification, with the HTRF kit from Cis-Bio International (cat no 62AM2 PEB). hADM 22-52 was used as reference antagonist.

Antibodies Testing cAMP-HTRF Assay

The anti-h-ADM antibodies (NT-H, MR-H, CT-H) were tested for antagonist activity in human recombinant adrenomedullin receptor (FAST-027C) cAMP functional assay in the presence of 5.63 nM Human ADM 1-52, at the following final antibody concentrations: 100 µg/ml, 20 µg/ml, 4 µg/ml, 0.8 µg/ml, 0.16 µg/ml.

The anti-m-ADM antibodies (NT-M, MR-M, CT-M) were tested for antagonist activity in human recombinant adrenomedullin receptor (FAST-027C) cAMP functional assay in the presence of 0.67 nM Mouse ADM 1-50, at the following final antibody concentrations: 100 µg/ml, 20 µg/ml, 4 µg/ml, 0.8 µg/ml, 0.16 µg/ml. Data were plotted relative inhibition vs. antagonist concentration (see FIGS. 3A to 3L). The maximal inhibition by the individual antibody is given in table 3.

TABLE 3

| Antibody | Maximal inhibition of ADM bioactivity (ADM-Bioassay) (%) |
|---|---|
| NT-H | 38 |
| MR-H | 73 |
| CT-H | 100 |
| NT-M FAB | 26 |
| NT-M FAB2 | 28 |
| NT-M | 45 |
| MR-M | 66 |
| CT-M | 100 |
| Non specific mouse IgG | 0 |

Example 3

Data for Stabilization of hADM by the Anti-ADM Antibody

The stabilizing effect of human ADM by human ADM antibodies was tested using a hADM immunoassay.

Immunoassay for the Quantification of Human Adrenomedullin

The technology used was a sandwich coated tube luminescence immunoassay, based on Acridinium ester labelling.

Labelled Compound (Tracer):

100 µg (100 ul) CT-H (1 mg/ml in PBS, pH 7.4, AdrenoMed AGGermany) was mixed with 10 µl Acridinium NHS-ester (1 mg/ml in acetonitrile, InVent GmbH, Germany) (EP 0353971) and incubated for 20 min at room temperature. Labelled CT-H was purified by Gel-filtration HPLC on Bio-Sil® SEC 400-5 (Bio-Rad Laboratories, Inc., USA) The purified CT-H was diluted in (300 mmol/L potassiumphosphate, 100 mmol/L NaCl, 10 mmol/L Na-EDTA, 5 g/L Bovine Serum Albumin, pH 7.0). The final concentration was approx. 800.000 relative light units (RLU) of labelled compound (approx. 20 ng labeled antibody) per 200 µL. Acridiniumester chemiluminescence was measured by using an AutoLumat LB 953 (Berthold Technologies GmbH & Co. KG).

Solid Phase:

Polystyrene tubes (Greiner Bio-One International AG, Austria) were coated (18 h at room temperature) with MR-H (AdrenoMed AG, Germany) (1.5 µg MR-H/0.3 mL 100 mmol/L NaCl, 50 mmol/L TRIS/HCl, pH 7.8). After blocking with 5% bovine serum albumine, the tubes were washed with PBS, pH 7.4 and vacuum dried.

Calibration:

The assay was calibrated, using dilutions of hADM (BACHEM AG, Switzerland) in 250 mmol/L NaCl, 2 g/L Triton X-100, 50 g/L Bovine Serum Albumin, 20 tabs/L Protease Inhibitor Cocktail (Roche Diagnostics AG, Switzerland))

hADM Immunoassay:

50 µl of sample (or calibrator) was pipetted into coated tubes, after adding labeled CT-H (200 µl), the tubes were incubated for 4 h at 4° C. Unbound tracer was removed by washing 5 times (each 1 ml) with washing solution (20 mM PBS, pH 7.4, 0.1% Triton X-100).

Tube-Bound Chemiluminescence was Measured by Using the LB 953

Figure 4:
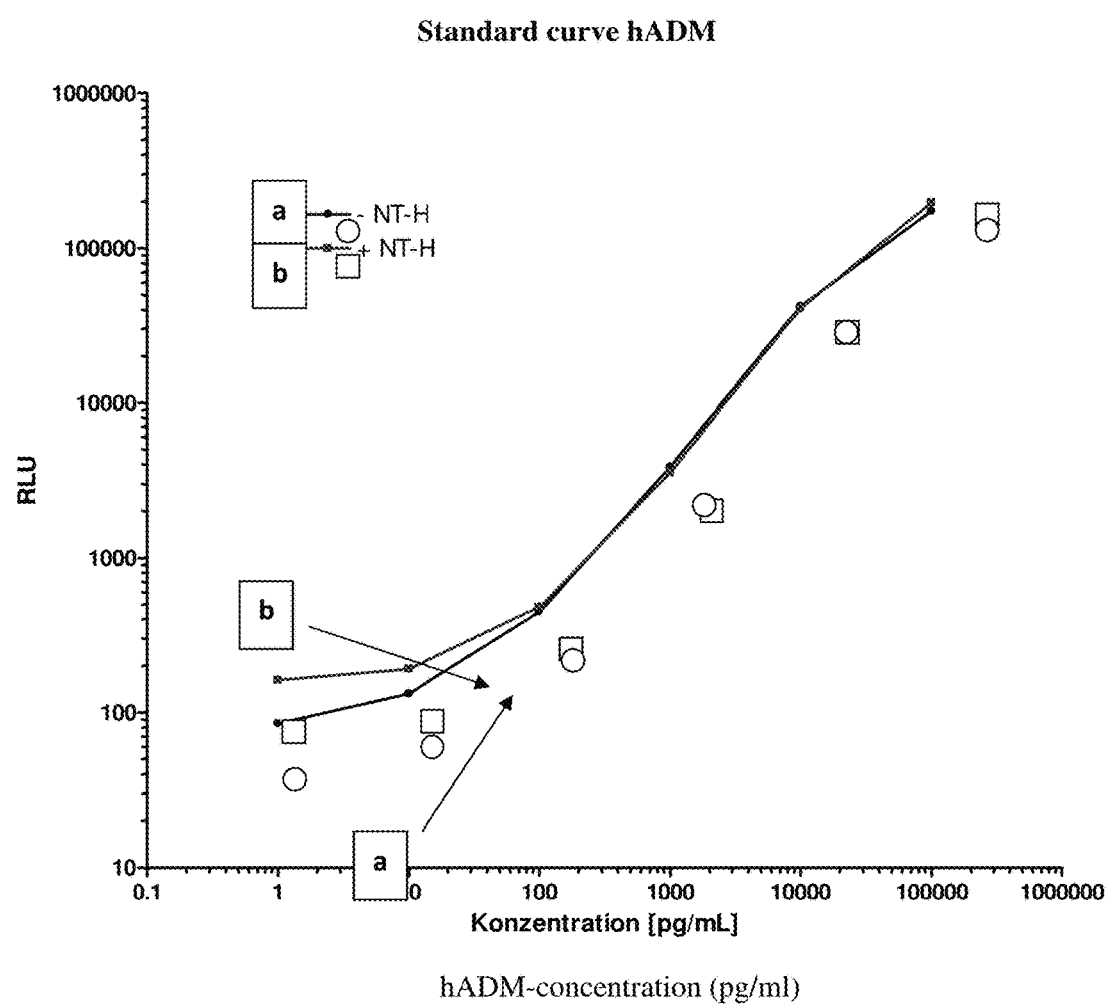
FIG. 4—This figure shows a typical hADM dose/signal curve. And an hADM dose signal curve in the presence of 100 µg/mL antibody NT-H.

FIG. 4 shows a typical hADM dose/signal curve. And an hADM dose signal curve in the presence of 100 μg/mL antibody NT-H.

NT-H did not affect the described hADM immunoassay.

Stability of Human Adrenomedullin:

Human ADM was diluted in human Citrate plasma (final concentration 10 nM) and incubated at 24° C. At selected time points, the degradation of hADM was stopped by freezing at −20° C. The incubation was performed in absence and presence of NT-H (100 μg/ml). The remaining hADM was quantified by using the hADM immunoassay described above.

Figure 5:
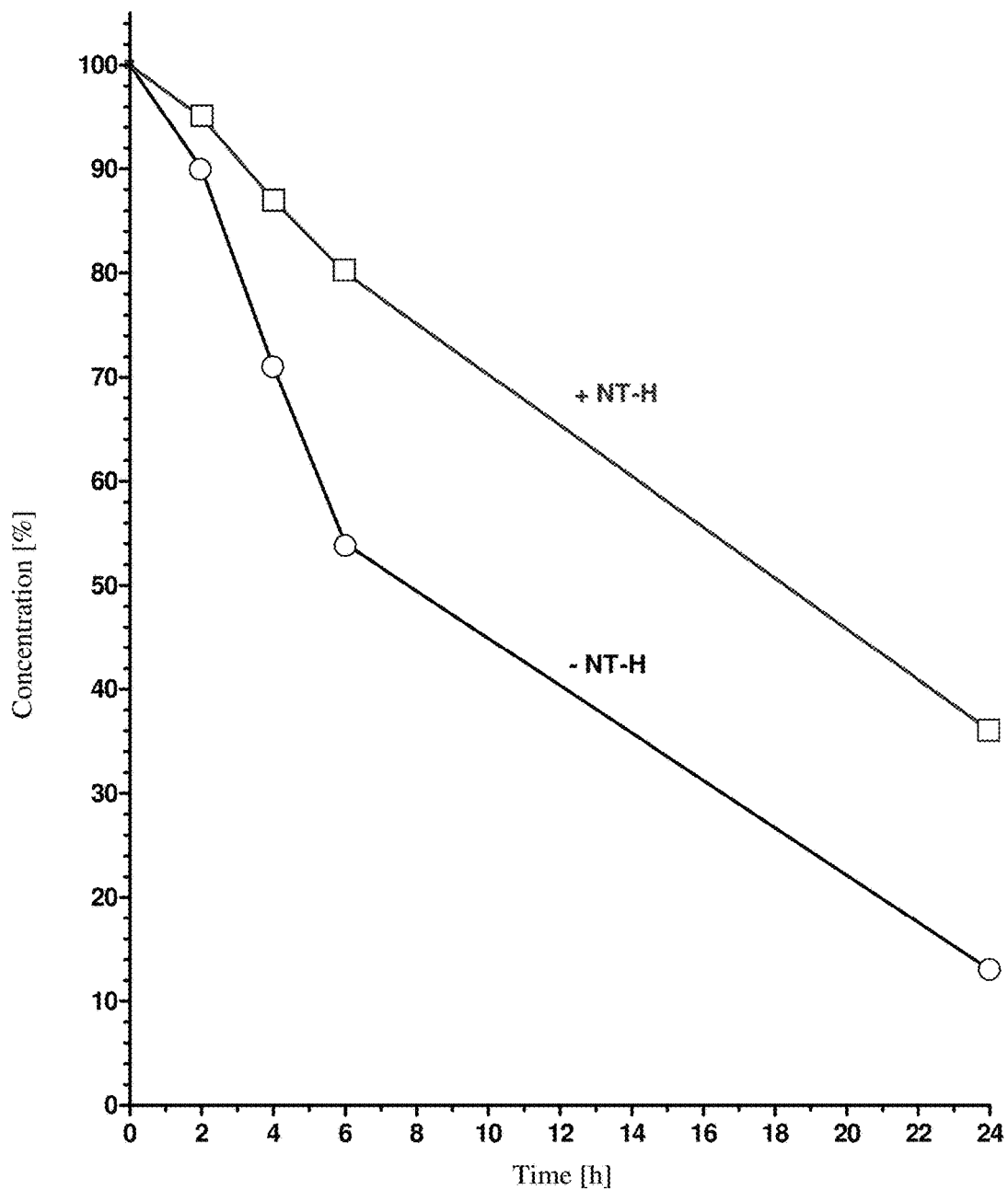
FIG. 5—This figure shows the stability of hADM in human plasma (citrate) in absence and in the presence of NT-H antibody.

FIG. 5 shows the stability of hADM in human plasma (citrate) in absence and in the presence of NT-H antibody. The half life of hADM alone was 7.8 h and in the presence of NT-H, the half life was 18.3 h. (2.3 times higher stability).

Example 4

Sepsis Mortality (Early Treatment)

Animal Model 12-15 week old male C57Bl/6 mice (Charles River Laboratories, Germany) were used for the study. Peritonitis had been surgically induced under light isofluran anesthesia. Incisions were made into the left upper quadrant of the peritoneal cavity (normal location of the cecum). The cecum was exposed and a tight ligature was placed around the cecum with sutures distal to the insertion of the small bowel. One puncture wound was made with a 24-gauge needle into the cecum and small amounts of cecal contents were expressed through the wound. The cecum was replaced into the peritoneal cavity and the laparotomy site was closed. Finally, animals were returned to their cages with free access to food and water. 500 μl saline were given s.c. as fluid replacement.

Application and Dosage of the Compound (NT-M, MR-M, CT-M)

Mice were treated immediately after CLP (early treatment). CLP is the abbreviation for cecal ligation and puncture (CLP).

Study Groups

Three compounds were tested versus: vehicle and versus control compound treatment. Each group contained 5 mice for blood drawing after 1 day for BUN (serum blood urea nitrogen test) determination. Ten further mice per each group were followed over a period of 4 days.

Group Treatment (10 μl/g bodyweight) dose/Follow-Up:

1 NT-M, 0.2 mg/ml survival over 4 days

2 MR-M, 0.2 mg/ml survival over 4 days

3 CT-M, 0.2 mg/ml survival over 4 days 4 non-specific mouse IgG, 0.2 mg/ml survival over 4 days 5 control—PBS 10 μl/g bodyweight survival over 4 days Clinical Chemistry Blood urea nitrogen (BUN) concentrations for renal function were measured baseline and day 1 after CLP. Blood samples were obtained from the cavernous sinus with a capillary under light ether anaesthesia. Measurements were performed by using an AU 400 Olympus Multianalyser. The 4-day mortality is given in table 4. The average BUN concentrations are given in table 5.

TABLE 4

| 4 day mortality | survival (%) |
| --- | --- |
| PBS | 0 |
| non-specific mouse IgG | 0 |
| CT-M | 10 |
| MR-M | 30 |
| NT-M | 70 |

TABLE 5

| Average from 5 animals | BUN pre CLP (mM) | BUN day 1 (mM) |
| --- | --- | --- |
| PBS | 8.0 | 23.2 |
| non-specific mouse IgG | 7.9 | 15.5 |
| CT-M | 7.8 | 13.5 |
| MR-M | 8.1 | 24.9 |
| NT-M | 8.8 | 8.2 |

It can be seen from Table 4 that the NT-M antibody reduced mortality considerably. After 4 days 70% of the mice survived when treated with NT-M antibody. When treated with MR-M antibody 30% of the animals survived and when treated with CT-M antibody 10% of the animals survived after 4 days. In contrast thereto all mice were dead after 4 days when treated with unspecific mouse IgG. The same result was obtained in the control group where PBS (phosphate buffered saline) was administered to mice.

The blood urea nitrogen or BUN test is used to evaluate kidney function, to help diagnose kidney disease, and to monitor patients with acute or chronic kidney dysfunction or failure.

The results of the S-BUN Test revealed that the NT-M antibody was the most effective to protect the kidney.

Sepsis Mortality (Late Treatment)

Animal Model 12-15 week old male C57Bl/6 mice (Charles River Laboratories, Germany) were used for the study. Peritonitis had been surgically induced under light isofluran anesthesia. Incisions were made into the left upper quadrant of the peritoneal cavity (normal location of the cecum). The cecum was exposed and a tight ligature was placed around the cecum with sutures distal to the insertion of the small bowel. One puncture wound was made with a 24-gauge needle into the cecum and small amounts of cecal contents were expressed through the wound. The cecum was replaced into the peritoneal cavity and the laparotomy site was closed. Finally, animals were returned to their cages with free access to food and water. 500 μl saline were given s.c. as fluid replacement.

Application and Dosage of the Compound (NT-M FAB2)

NT-M FAB2 was tested versus: vehicle and versus control compound treatment. Treatment was performed after full development of sepsis, 6 hours after CLP (late treatment). Each group contained 4 mice and were followed over a period of 4 days. Group Treatment (10 μl/g bodyweight) dose/Follow-Up:

Study Groups

1 NT-M, FAB2 0.2 mg/ml survival over 4 days 2 control: non-specific mouse IgG, 0.2 mg/ml survival over 4 days 3 vehicle: —PBS 10 μl/g bodyweight survival over 4 days

TABLE 6

| 4 day mortality | survival (%) |
| --- | --- |
| PBS | 0 |
| Non-specific mouse IgG | 0 |
| NT-M FAB2 | 75 |

It can be seen from Table 6 that the NT-M FAB 2 antibody reduced mortality considerably. After 4 days 75% of the mice survived when treated with NT-M FAB 2 antibody. In contrast thereto all mice were dead after 4 days when treated with non-specific mouse IgG. The same result was obtained in the control group where PBS (phosphate buffered saline) was administered to mice.

Example 5

Incremental Effect of Anti-ADM Antibody in CLP-Animals on Top of Antibiotic Treatment and Circulation Stabilization Via Catecholamines as Well as Regulation of Fluid Balance Animal Model In this study male C57Bl/6 mice (8-12 weeks, 22-30 g) were utilized. A polymicrobial sepsis induced by cecal ligation and puncture (CLP) was used as the model for studying septic shock ((Albuszies G, et al: Effect of increased cardiac output on hepatic and intestinal microcirculatory blood flow, oxygenation, and metabolism in hyperdynamic murine septic shock. Crit Care Med 2005; 33:2332-8), (Albuszies G, et al: The effect of iNOS deletion on hepatic gluconeogenesis in hyperdynamic murine septic shock. Intensive Care Med 2007; 33:1094-101), (Barth E, et al: Role of iNOS in the reduced responsiveness of the myocardium to catecholamines in a hyperdynamic, murine model of septic shock. Crit Care Med 2006; 34:307-13), (Baumgart K, et al: Effect of SOD-1 over-expression on myocardial function during resuscitated murine septic shock. Intensive Care Med 2009; 35:344-9), (Baumgart K, et al: Cardiac and metabolic effects of hypothermia and inhaled H2S in anesthetized and ventilated mice. Crit Care Med 2010; 38:588-95), (Simkova V, et al: The effect of SOD-1 over-expression on hepatic gluconeogenesis and whole-body glucose oxidation during resuscitated, normotensive murine septic shock. Shock 2008; 30:578-84), (Wagner F, et al.: Inflammatory effects of hypothermia and inhaled H2S during resuscitated, hyperdynamic murine septic shock. Shock, im Druck), (Wagner F, et al: Effects of intravenous H2S after murine blunt chest trauma: a prospective, randomized controlled trial. Crit Care 2011, submittes for publication)).

After weighing, mice were anesthetized by intraperitoneal injection of 120 µg/g Ketamin, 1.25 µg/g Midazolam and 0.25 µg/g Fentanyl. During the surgical procedure, body temperature was kept at 37-38° C. A 1 cm midline abdominal section was performed to get access to the cecum. The cecum then was ligated with 3-0 silk tie close to the basis and a single puncture with a 18-gauge needle was applied. The cecum was returned and the incision was closed again (4-0 tie). For the compensation of perioperative loss of liquids, 0.5 ml lacted Ringer's solution with 1 µg/g Buprenorphin as analgetic was injected subcutaneously in dorsal dermis. For antibiosis the mice received Ceftriaxon 30 µg/g and Clindamycin 30 µg/g subcutaneously via the lower extremities.

After CLP surgery the animal were kept in an adequately heated environment with water and food ad libitum.

The covering of liquid requirements were ensured by a dorsal subcutaneous injections with 0.5 ml lactated ringer's solution with 4 µg/g glucose and Buprenorphin 1 µg/g, which were applied in an 8 hour cycle, after short term anesthesia by isofluran. In addition, antibiosis was maintained by subcutaneous injections of Ceftriaxon 30 µg/g and Clindamycin 30 µg/g via the lower extremities.

Dosing of Test Substances

Early Treatment

Immediately after the CLP surgery and closing of the incision, the test substance antibody NT-M was applied in a concentration of 500 µg/ml in phosphate buffered saline (PBS) via injection into the penis vein for a dose of 2 mg per kg body weight (dose volume 88-120 µl) (5 animals).

Late Treatment

After full Sepsis development, 15.5 h after CLP surgery, animals were anesthetized as described above and NT-M was applied in a concentration of 500 µg/ml in phosphate buffered saline (PBS) via injection into the penis vein for a dose of 2 mg per kg body weight (dose volume 88-120 µl) (3 animals).

The control group (6 animals) received a corresponding amount of the vehicle PBS solution without antibody (4 µl/g, 88-120 µl) immediately after CLP surgery.

Study Groups and Experimental Setting

Murine septic shock model under intensive care monitoring:

Three groups with 3, 5 and 6 animals were monitored. Group 1 (5 animals) received the antibody NT-M 15.5 h after CLP, group 2 received the antibody NT-M immediately after CLP surgery and group 3 received a comparable amount of PBS (4 µl/g). 16 hour incubation post CLP (to allow the polymicrobial sepsis to progress), the experiment was continued with monitoring and interventions comparable to an intensive medical care regime. Therefore, after weighing the animals were anesthetized as described in the CLP surgery part (except the late treated animals, which were anesthetized before treatment). Body temperature was maintained at 37-38° C. for the rest of the experiment. After a tracheotomy and intubation, respiration was monitored and supported by laboratory animal lung ventilator Flexivent®, (Emka Technologies, FiO2 0.5, PEEP 10 H2O, VT 8 µl/g, I:E 1:1.5, AF 70-140 depending on temperature).

Anesthesia was maintained throughout the experiment via the cannulated vena jugularis externa dextra with a continuous infusion of Ketamin 30 µg/g×h and Fentanyl 0.3 µg/g×h. Furthermore, the right aorta carotis communis was cannulated for continuous monitoring of heart rate and the mean arterial pressure (MAP). The mean arterial pressure was maintained at MAP>65 mmHg via intravenous (V. jugularis) infusion of colloids (80 µL/g×h, Hextend®) and, if needed, Noradrenalin dissolved in colloids as vasopressor. Blood samples (120 µl) were taken via the cannulated A. carotis at 0 and 4 hours for determination of creatinine. The bladder was punctured and urine was collected via a bladder catheter. The experiment was either terminated after 6 hours or prior to this, if the MAP>65 mmHg (V. jugularis) could not be maintained with the vasorpressor dosing.

Measured Parameters

The following parameters were measured and analyzed: Total consumption of noradrenalin (µg NA/g), consumption rate of noradrenalin (µg NA/g/h), total volume of urine collected during the experiment, creatinine concentration (µg/mL) at the end of the experiment and mean creatinine clearance (µL/min).

TABLE 7

|  | Total consumption of Noradrenalin (μg NA/g) (Average) | consumption rate of Noradrenalin (μg NA/g/h) (Average) |
| --- | --- | --- |
| Control (mouse IgG) (N = 6) | 0.17 μg/g | 0.032 μg/h/g |
| NT-M (N = 5) early treatment | 0.07 μg/g | 0.012 μg/h/g |
| Relative change (early treatment, amelioration) | 59% (59%) | 62.5% (62.5%) |
| NT-M (N = 3) late treatment | 0.04 μg/g | 0.0075 μg/h/g |
| Relative change (late treatment, amelioration) | 76.5% (76.5%) | 76.5% (76.5%) |

The catecholamine requirement was measured after administration of either non specific mouse IgG to a total of 6 mice as control group, NT-murine antibody to a group of 5 mice immediately after CLP (early treatment) or NT-murine antibody to a group of 3 mice 15.5 h after CLP (late treatment).

Figure 7:
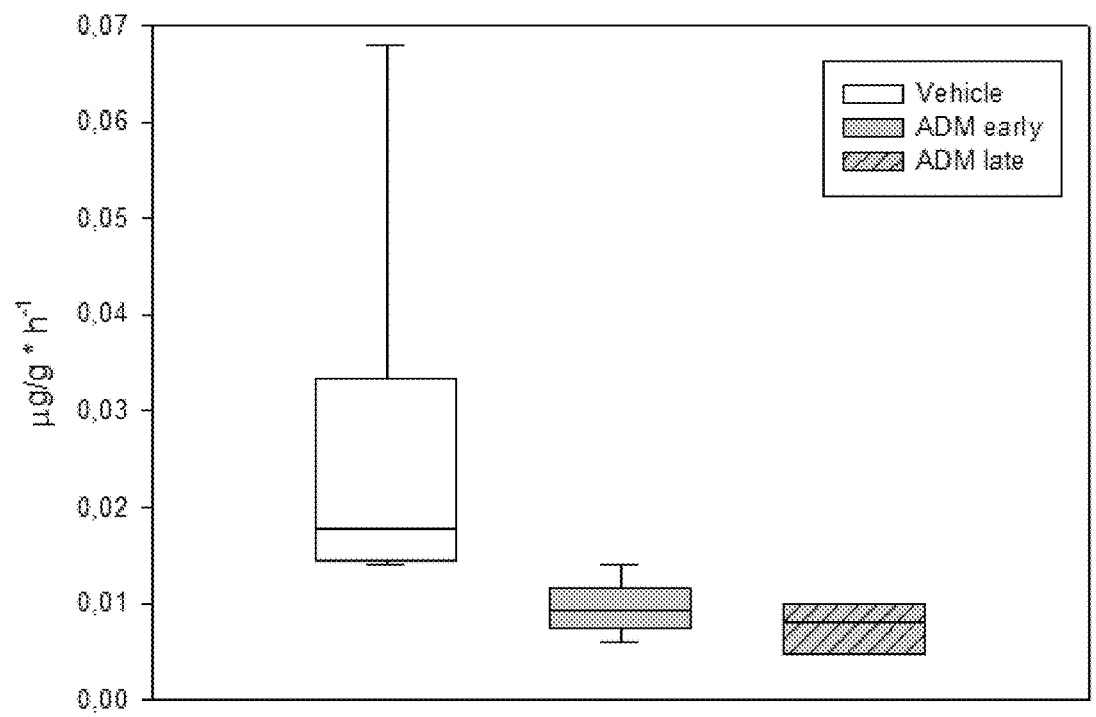
FIG. 7—This figure shows the Noradrenalin requirements for early and late treatment with NT-M.

The reduction of the catecholamine requirement is a measure for the stabilization of the circulation. Thus, the data show that the ADM antibody, especially the NT-M antibody, leads to a considerable stabilization of the circulation and to a considerable reduction of the catecholamine requirement. The circulation-stabilizing effect was given in early treatment (immediately after CLP) and treatment after full sepsis development (late treatment) (see FIG. 7).

Regulation of Fluid Balance

Figure 8:
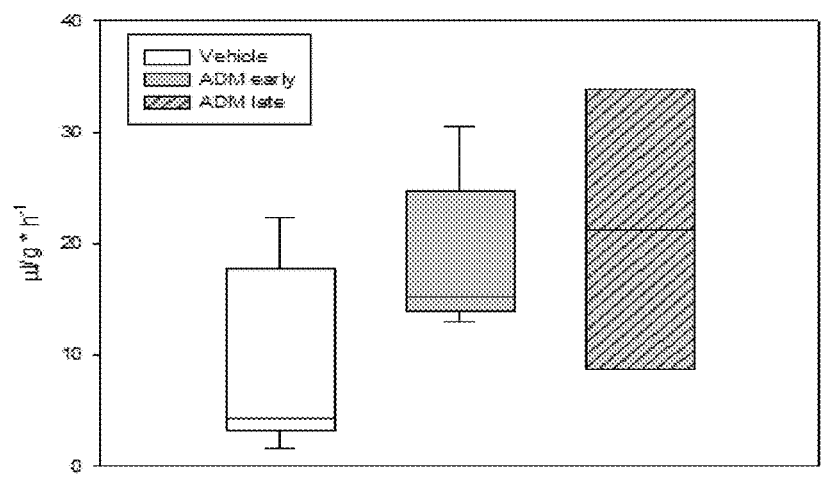
FIG. 8—This figure shows urine production after early and late treatment with NT-M.
Figure 9:
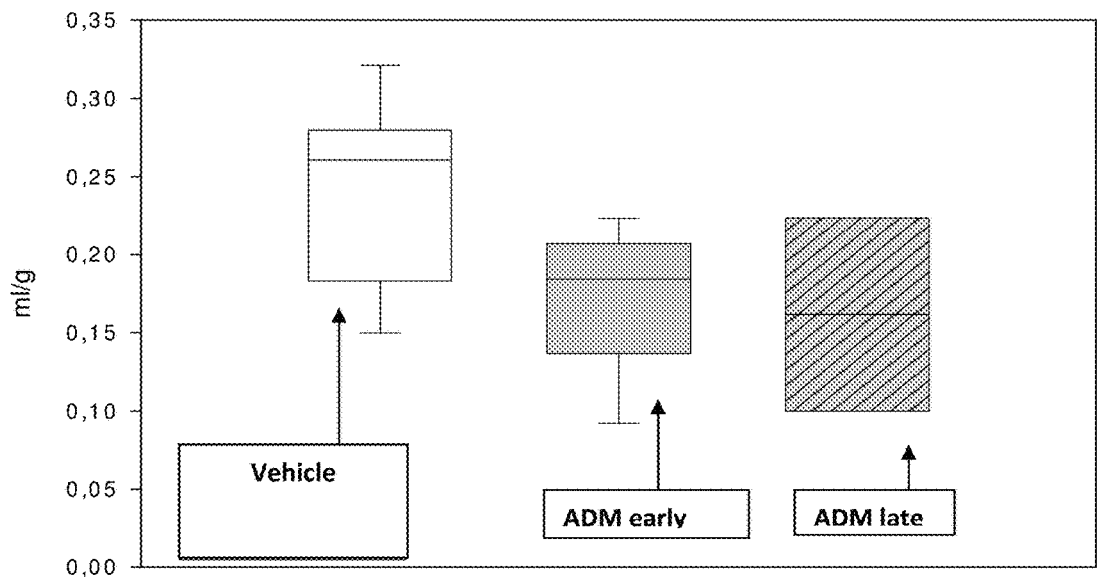
FIG. 9—This figure shows the fluid balance after early and late treatment with NT-M.

More positive fluid balance both early in resuscitation and cumulatively over 4 days is associated with an increased risk of mortality in septic shock. The control of the liquid balance is of utmost importance for the course of disease of patients having sepsis. (s. Boyd et al, 2011). Controlling the liquid balance of critical ill patients remains as a substantial challenge in intensive care medicine. As can be seen in table 8 treatment of mice after CLP (experimental procedures see "Animal Model") with NT-M antibody lead to an enhancement of the total volume of urine excreted. The urine secreted was approx. three times higher in NT-M-treated animals compared to non-treated mice. The positive treatment effect was given in early- and in late treatment. The fluid balance was improved by about 20-30%, also in both, early and late treatment. Thus, the data show that the use of ADM antibody, especially the use of NT ADM antibody, is favorable for regulating the fluid balance in patients. (see table 8 and FIGS. 8 and 9).

TABLE 8

|  | Urine average volume/g body weight | Fluid balance average volume/g body weight |
| --- | --- | --- |
| Control (mouse IgG) (N = 6) | 0.042 ml/g | 0.23 ml/g |
| NT-M early (N = 5) | 0.12 ml | 0.18 ml/g |
| Relative change early treatment | +186% | −21.7%% |
| NT-M late (N = 3) | 0.125 ml | 0.16 ml/g |
| Relative change late treatment | +198% | −30.5% |

Improvement of Kidney Function

The combination of acute renal failure and sepsis is associated with a 70 percent mortality, as compared with a 45 percent mortality among patients with acute renal failure alone. (Schrier and Wang, "Mechanisms of Disease Acute Renal Failure and Sepsis"; The New England Journal of Medicine; 351:159-69; 2004). Creatinine concentration and creatinine clearance are standard laboratory parameters for monitoring kidney (dys)function (Jacob, "Acute Renal Failure", Indian J. Anaesth.; 47 (5): 367-372; 2003). Creatinine and creatinine clearance data from above described animal experiment (early treatment) are given in Table 9.

TABLE 9

| Kidney function: | | |
| --- | --- | --- |
|  | creatinine concentration (μg/mL) | mean creatinine clearance (μL/min) |
| control mouse IgG (MW) | 2.6 μg/ml | 174 μl/min |
| NT-M (MW) | 1.5 μg/ml | 373 μl/min |
| Relative change (amelioration) | −42% (42%) | +114% (114%) |

In comparison to control septic animals, the creatinine concentration was lowered by 42% and the creatinine clearance was improved by more than 100% as a result of NT-M treatment (Table 9). The data show that the administration of ADM-antibody, especially NT-M, leads to an improvement of kidney function.

Improvement of Liver Inflammatory Status

Figure 10:
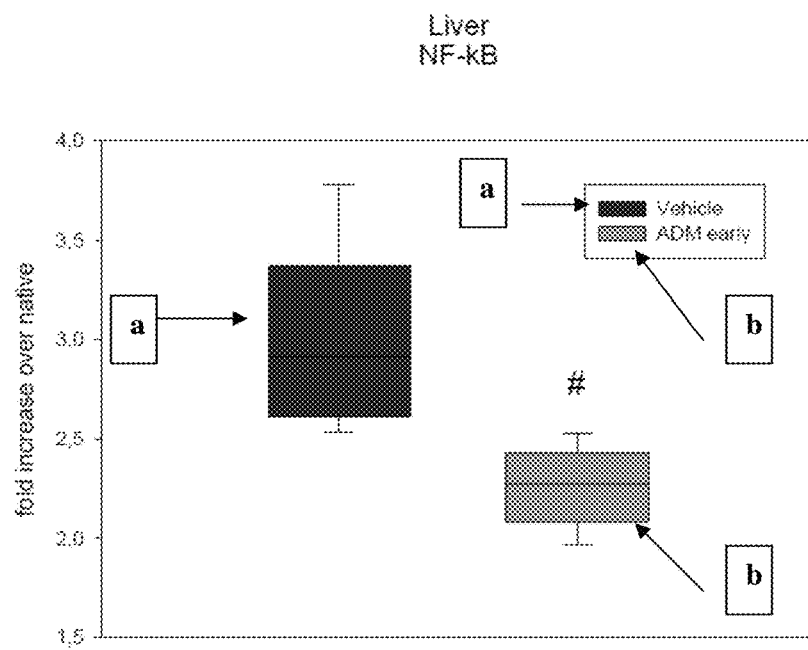
FIG. 10—Liver tissue activation of nuclear factor kappa-light-chain gene enhancer in B cells (NF-κB) analyzed by electophoretic mobility shift assay (EMSA). # depicts p<0.001 vs. vehicle.

Liver tissue for control and early treated animals was homogenized and lysed in lysing buffer. For cell extract preparation, cells were resuspended, lysed on ice, and centrifuged. The supernatant (protein extract) was stored at −80° C. Activation of nuclear factor kappa-light-chain gene enhancer in B cells (NF-κB) was determined as previously described using an electrophoretic mobility shift assay (EMSA) 1,2. Cell extracts (10 μg) were incubated on ice with poly-doxy-inosinic-deoxy-cytidylic acid (poly-dI-dC) and a 32P-labeled double stranded oligonucleotide (Biomers, Ulm, Germany) containing the NF-κB (HIV κBsite). Complexes were separated in native polyacrylamide gels, dried and exposed to X-ray films. A phosphorimager and image analyzer software (AIDA Image Analyzer; Raytest) was used to quantify the radioactively labeled NF-κB by densitometry. For comparison between individual gels, the intensity of each band was related to that of simultaneously loaded control animals which had not undergone surgical instrumentation and CLP. Therefore, the EMSA data are expressed as fold increase over control values. Statistics: All data are presented as median (range) unless otherwise stated differences between the two groups were analyzed with the Mann-Whitney rank sum test for unpaired samples. Results: The animals treated with NT-M presented with significantly attenuated liver tissue NF-κB activation (2.27 (1.97-2.53)) compared to vehicle animals (2.92 (2.50-3.81)) ($p<0.001$) (see FIG. 10).

REFERENCES

1. Wagner F, Wagner K, Weber S, Stahl B, Knöferl M W, Huber-Lang M, Seitz D H, Asfar P, Calzia E, Senftleben U, Gebhard F, Georgieff M, Radermacher P, Hysa V: Inflammatory effects of hypothermia and inhaled H2S during resuscitated, hyperdynamic murine septic shock. Shock 2011; 35(4):396-402
2. Wagner F, Scheuerle A, Weber S, Stahl B, McCook O, Knöferl M W, Huber-Lang M, Seitz D H, Thomas J, Asfar P, Szabó C, Möller P, Gebhard F, Georgieff M, Calzia E, Radermacher P, Wagner K: Cardiopulmonary, histologic, and inflammatory effects of intravenous Na2S after blunt chest trauma-induced lung contusion in mice. J Trauma 2011; 71(6):1659-67.

Example 6

In Vivo Side Effect Determination of Antibody NT-M 12-15 week old male C57Bl/6 mice (Charles River Laboratories, Germany) were used for the study. 6 mice were treated with (10 µl/g bodyweight) dose of NT-M, 0.2 mg/ml. As control, 6 mice were treated with (10 µl/g body weight) PBS. Survival and physical condition was monitored for 14 days. The mortality was 0 in both groups, there were no differences in physical condition between NT-M and control group.

Example 7

Gentamicin-Induced Nephrotoxicity

A non-septic acute kidney injury model has been established, which makes use of the nephrotoxicity induced by Gentamicin (Chiu P J S. Models used to assess renal functions. Drug Develop Res 32:247-255, 1994). This model was used to assess whether treatment with anti-Adrenomedullin antibody can improve kidney function.

The experiment was performed as follows:

Effect of a NT-M on Gentamicin-Induced Nephrotoxicity in Rats
Study Design:

| Group | Test Article | Route | Conc mg/ml | Dosage ml/kg | Dosage mg/kg | Rats[d] (Male) |
|---|---|---|---|---|---|---|
| 1 | Gentamicin[a] + vehicle[b] | IV | | NA × 4[c] | | 8 |
| 2 | Gentamicin[a] + NT-M | IV | | X 4[c] | | 8 |

[a]Gentamicin at 120 mg/kg intramuscularly for 7 days (days 0-6).
[b]Vehicle; injected intravenously (i.v.) 5 min before gentamicin on Day 0, followed by injections on Days 2, 4, and 6.
[c]NT-M at 4 mg/kg was injected intravenously (i.v.) 5 min before gentamicin on Day 0, followed by 2 mg/kg i.v. on Days 2, 4, and 6.
[d]Plasma samples were collected in EDTA tubes (Days 1 and 3 before Test and Control article: 100 µl; Day 7: 120 µl). 24 h urine collection on ice is initiated after gentamicin on Day 0, followed by Days 2 and 6; blood collection on days 1, 3, and 7.

Groups of 8 male Sprague-Dawley rats weighing 250±20 g were employed. Animals were challenged with gentamicin at 120 mg/kg i.m. for seven consecutive days (Groups 1 and 2). Test compound (anti-adrenomedullin antibody NT-M) and vehicle (phosphate buffered saline) were injected intravenously 5 min before gentamicin on day 0, followed by injection on days 2, 4, and 6. Body weights and clinical signs were monitored daily. Twenty-four (24) hour urine collections on ice were performed on Days 0, 2, and 6. Urine specimens were assayed for concentrations of Na+ and K+, and creatinine. Blood samples for clinical chemistry were collected on Days 1 (before gentamicin), 3 (before gentamicin), and 7. Serum electrolytes (Na+ and K+), creatinine, and BUN were the primary analytes that were monitored for assessing renal function. Plasma samples were collected in EDTA tubes (Days 1 and 3:100 µl; Day 7:120 µl). Creatinine clearance was calculated. Urine volume, urinary electrolytes, and creatinine are expressed as amount excreted per 100 g of animal body weight. All animals were sacrificed on Day 7. Kidneys were weighed.

Urine collection. The animals were placed in individual cages where urine was collected for 24 h on Day 0, Day 2, and Day 6. Urine volume, urinary Na+, K+, and creatinine were measured.

Endogenous creatinine clearance was calculated as follows:

$$CCr\ (ml/24\ h) = [UCr\ (mg/ml) \times V\ (ml/24\ h)]/SCr\ (mg/ml)$$

24-hr urinary excretion of sodium (Na+) was calculated as follows:

$$UNaV\ (\mu Eq/24\ h) = UNa\ (\mu Eq/ml) \times V\ (ml/24\ h)$$

24-hr urinary excretion of NAG and NGAL was similarly calculated.

The fractional excretion of Na+ ($FE_{Na}$), or percentage of the filtered sodium that is excreted into the final urine, is a measure of tubular Na+ reabsorptive function. It was computed as follows:

$$FE_{Na}\ (\%) = 100 \times [U_{Na}\ (\mu Eq/ml) \times V\ (ml/24\ h)]/P_{Na}\ (\mu Eq/ml) \times C_{Cr}\ (ml/24\ h)$$

Figure 11:
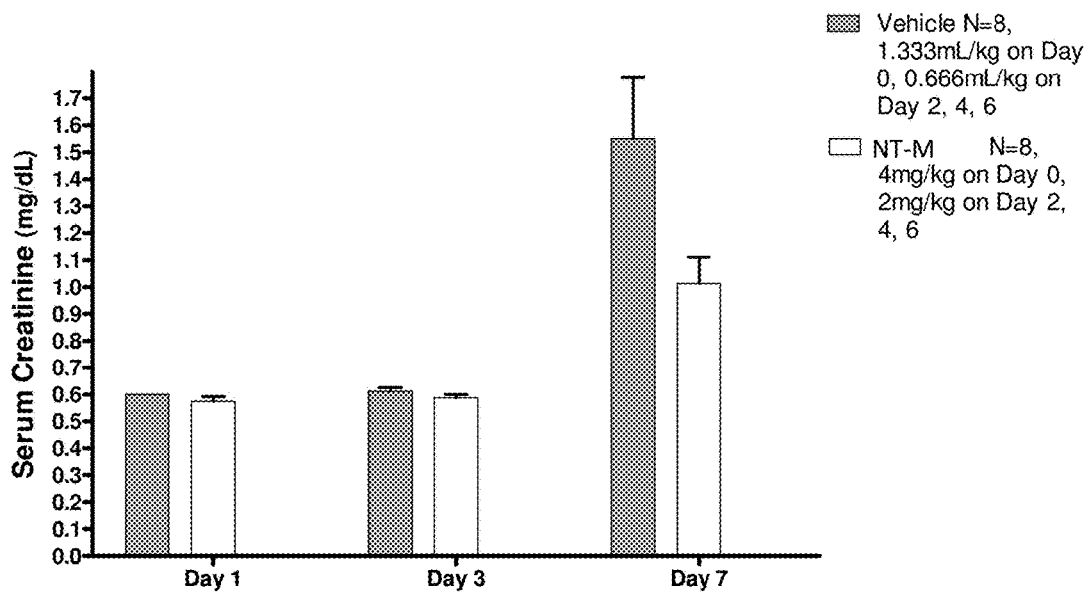
FIG. 11—Development of serum creatinine over time. Mean+/−SEM are shown.
Figure 12:
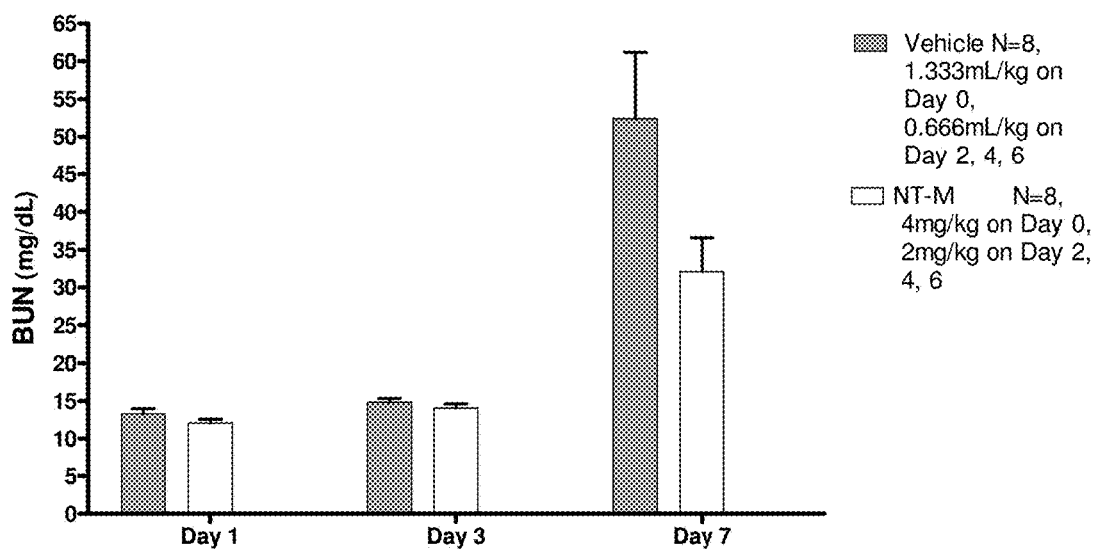
FIG. 12—Development of blood urea nitrogen (BUN) over time. Mean+/−SEM are shown.
Figure 13:
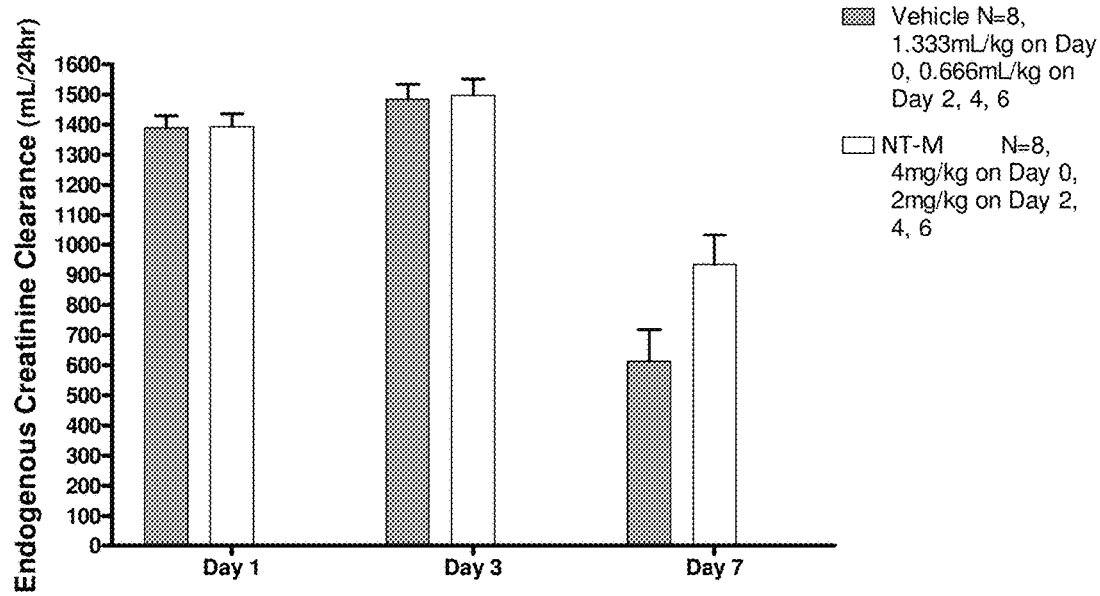
FIG. 13—Development of endogenous creatinine clearance over time. Mean+/−SEM are shown.
Figure 14:
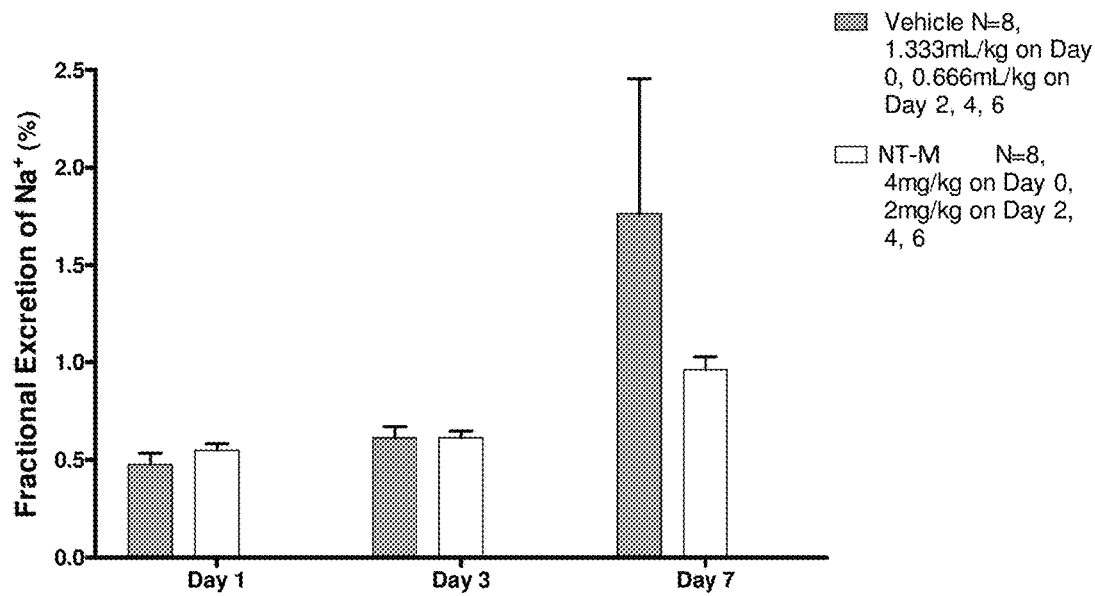
FIG. 14—Development of fractional secretion of Na+ over time. Mean+/−SEM are shown.

Treatment with anti-Adrenomedullin antibody improved several measures of kidney function on day 7 as compared to vehicle: serum creatinine 1.01 mg/dL (NT-M) vs 1.55 mg/dL (vehicle) (FIG. 11), BUN 32.08 mg/dL (NT-M) vs. 52.41 mg/dL (vehicle) (FIG. 12), endogenous creatinine clearance 934.43 mL/24 h (NT-M) vs. 613.34 mL/24 h (vehicle) (FIG. 13), fractional secretion of Na+ 0.98% (NT-M) vs. 1.75% (vehicle) (FIG. 14).

Example 8

In the mice CLP model described above, the effect of treatment with anti-adrenomedullin antibody NT-M on several parameters of kidney function was investigated.

Figure 15:
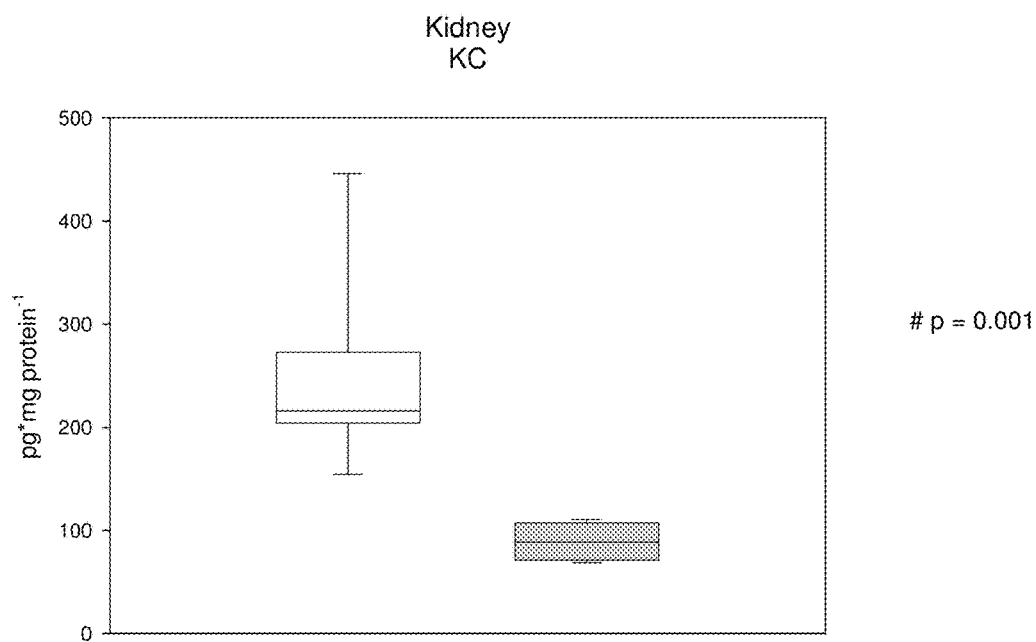
FIG. 15—Keratinocyte-derived chemokine (KC) levels determined in relation to the total kidney protein extracted. The white box-plot shows results obtained with vehicle, the grey box-plot shows results obtained after treatment with NT-M.

NT-M caused a three- and two-fold higher diuresis and creatinine clearance, respectively, ultimately resulting in lower creatinine, urea, and NGAL blood concentrations at the end of the experiment (see Table 10). Moreover, keratinocyte-derived chemokine (KC) concentrations in the kidney were significantly lowered by treatment with NT-M (FIG. 15).

TABLE 10

Parameters of kidney function in the vehicle- (n = 11) and NT-M-treated (n = 9) animals. Blood concentrations were measured in samples taken at the end of the experiment. NGAL = neutrophil gelatinase-associated lipocalin. All data are median (quartiles).

| | Vehicle | NT-M | p-Value |
|---|---|---|---|
| Urine output [µL · g$^{-1}$ · h$^{-1}$] | 4.4 (3.5; 16.5) | 15.2 (13.9; 22.5) | 0.033 |
| Creatinine clearance [µL · min$^{-1}$] | 197 (110; 301) | 400 (316; 509) | 0.006 |
| Creatinine [µg · mL$^{-1}$] | 1.83 (1.52; 3.04) | 1.28 (1.20; 1.52) | 0.010 |
| Urea [µg · mL$^{-1}$] | 378 (268; 513) | 175 (101; 184) | 0.004 |
| NGAL [µg · mL$^{-1}$] | 16 (15; 20) | 11 (10; 13) | 0.008 |

The experiments were performed as follows:

Creatinine, Urea, and Neutrophil Gelatinase-Associated Lipocalin (NGAL)

Blood NGAL concentrations were measured using a commercial ELISA (mouse NGAL, RUO 042, BioPorto Diagnostics A/S, Denmark, Gentofte). Urea and creatinine concentrations were measured with a capillary column (Optima-5MS, Macherey-Nagel, Düren, Germany) gas chromatography/mass spectrometry system (Agilent 5890/5970, Böblingen, Germany) using $^2H_3$-creatinine (CDN isotopes, Pointe-Claire, QU, Canada) and methyl-urea (FlukaChemikalien, Buchs, Switzerland) as internal standards.

After deproteinization with acetonitrile, centrifugation and evaporation to dryness, the supernatant was reconstituted in formic acid, and extracted over a weak anion exchange column (WCX, Phenomenex, Aschaffenburg, Germany). Acetonitrile plus N,O-Bis(trimethylsilyl)trifluoroacetamide and N-(tert-butyldimethylsilyl)-N-methyltrifluoroacetamide allowed formation of the urea tert-butyl-dimethylsilyl- and the creatininetrimethylsilyl-derivatives, respectively. Ions m/z 231 and 245, and m/z 329 and 332 were monitored for urea and creatinine analytes and internal standards, respectively. From the urine output and the plasma and urine creatinine concentrations creatinine clearance was calculated using the standard formula.

Sample Preparation

The kidney which was stored at −80° C. was disrupted with a homogenizer in PBS and lysed with a 2-fold concentrated buffer for a whole cell lysate (100 mM Tris pH 7.6; 500 mM NaCl; 6 mM EDTA; 6 mM EGTA; 1% Triton-X-100; 0.5% NP 40; 10% Glycerol; Protease-Inhibitors (β-Glycerolphosphate 2 mM; DTT 4 mM; Leupeptine 20 µM; Natriumorthovanadate 0.2 mM)) and subsequently centrifuged. The whole cell lysate was obtained out of the supernatant; the pellet consisting of cell remnants was discarded. The amount of protein was determined photometrically with a commercially available protein assay (Bio-Rad, Hercules, Calif.) and the specimens were adjusted in the way that the final protein concentration was 4 µg/µl. The samples for the Multiplex- and EMSA analysis were diluted 1:1 with EMSA buffer (10 mM Hepes; 50 mM KCl; 10% Glycerol; 0.1 mM EDTA; 1 mM DTT), the samples for the immuno blots 1:1 with 2-fold Sample Buffer (2% SDS; 125 mM Tris-HCL (pH 6.8 at 25° C.); 10% Glycerol; 50 mM DTT; 0.01% Bromophenol blue).

Levels of keratinocyte-derived chemokine (KC) concentrations were determined using a mouse multiplex cytokine kit (Bio-Plex Pro Cytokine Assay, Bio-Rad, Hercules, Calif.), the assay was performed by using the Bio-plex suspension array system with the manufacturer's instructions (see also Wagner F, Wagner K, Weber S, Stahl B, Knöferl M W, Huber-Lang M, Seitz D H, Asfar P, Calzia E, Senftleben U, Gebhard F, Georgieff M, Radermacher P, Hysa V. Inflammatory effects of hypothermia and inhaled H2S during resuscitated, hyperdynamic murine septic shock. Shock 2011; 35:396-402; and Wagner F, Scheuerle A, Weber S, Stahl B, McCook O, Knöferl M W, Huber-Lang M, Seitz D H, Thomas J, Asfar P, Szabó C, Möller P, Gebhard F, Georgieff M, Calzia E, Radermacher P, Wagner K. Cardiopulmonary, histologic, and inflammatory effects of intravenous Na2S after blunt chest trauma-induced lung contusion in mice. J Trauma 2011; 71:1659-1667). In brief, the appropriate cytokine standards and samples were added to a filter plate. The samples were incubated with antibodies chemically attached to fluorescent-labeled micro beads. Thereafter, premixed detection antibodies were added to each well, and subsequently, streptavidin-phycoerythrin was added. Beads were then re-suspended, and the cytokines reaction mixture was quantified using the Bio-Plex protein array reader. Data were automatically processed and analyzed by Bio-Plex Manager Software 4.1 using the standard curve produced from recombinant cytokine standards. Levels below the detection limit of the assays were set to zero for statistical purposes.

Example 9

In the mice CLP model described above, the effect of treatment with anti-adrenomedullin antibody NT-M on the liver was investigated.

Figure 16:
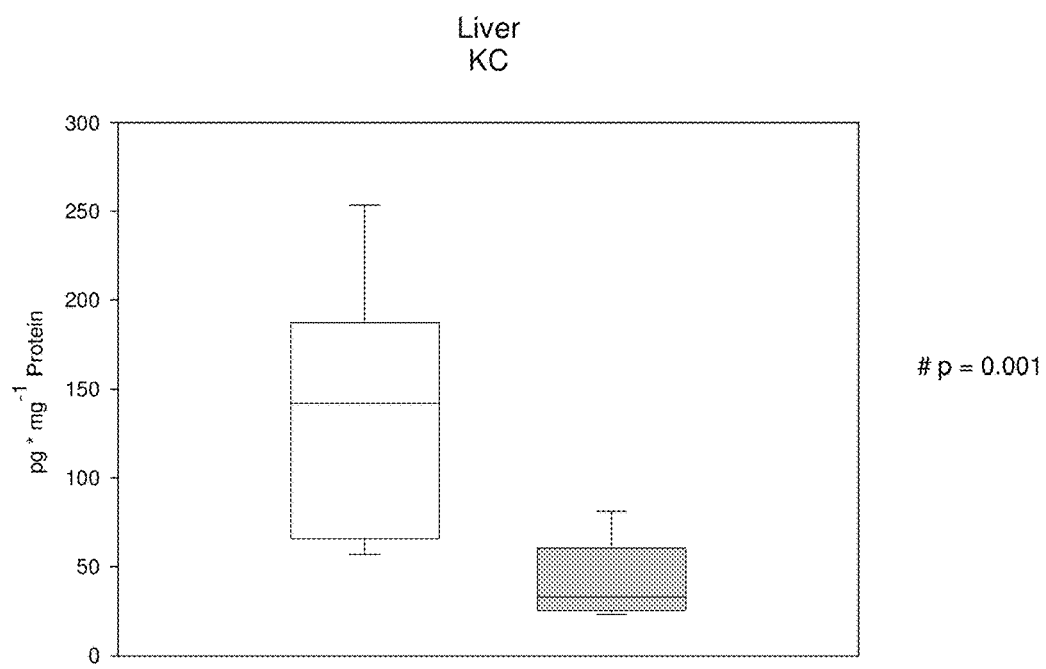
FIG. 16—Keratinocyte-derived chemokine (KC) levels determined in relation to the total liver protein extracted. The white box-plot shows results obtained with vehicle, the grey box-plot shows results obtained after treatment with NT-M.

NT-M caused a significant lowering of keratinocyte-derived chemokine (KC) concentrations in the liver (FIG. 16).

Measurement of keratinocyte-derived chemokine (KC) was done analogous to example 8 (kidney).

Example 10

In the mice CLP model described above, the effect of treatment with anti-adrenomedullin antibody NT-M on several cytokines and chemokinesin the blood circulation (plasma) was investigated.

Cytokine and Chemokine Concentrations

Plasma levels of tumor necrosis factor (TNF)-α, interleukin (IL)-6, monocyte chemoattractant protein (MCP)-1, and keratinocyte-derived chemokine (KC) concentrations were determined using a mouse multiplex cytokine kit (Bio-Plex Pro Cytokine Assay, Bio-Rad, Hercules, Calif.), the assay was performed by using the Bio-plex suspension array system with the manufacturer's instructions (see also Wagner F, Wagner K, Weber S, Stahl B, Knöferl M W, Huber-Lang M, Seitz D H, Asfar P, Calzia E, Senftleben U, Gebhard F, Georgieff M, Radermacher P, Hysa V Inflammatory effects of hypothermia and inhaled H2S during resuscitated, hyperdynamic murine septic shock. Shock 2011; 35:396-402; and Wagner F, Scheuerle A, Weber S, Stahl B, McCook O, Knöferl M W, Huber-Lang M, Seitz D H, Thomas J, Asfar P, Szabó C, Möller P, Gebhard F, Georgieff M, Calzia E, Radermacher P, Wagner K. Cardiopulmonary, histologic, and inflammatory effects of intravenous Na2S after blunt chest trauma-induced lung contusion in mice. J Trauma 2011; 71:1659-1667).

In brief, the appropriate cytokine standards and samples were added to a filter plate. The samples were incubated with antibodies chemically attached to fluorescent-labeled micro beads. Thereafter, premixed detection antibodies were added to each well, and subsequently, streptavidin-phycoerythrin was added. Beads were then re-suspended, and the cytokines reaction mixture was quantified using the Bio-Plex protein array reader. Data were automatically processed and analyzed by Bio-Plex Manager Software 4.1 using the standard curve produced from recombinant cytokine standards. Levels below the detection limit of the assays were set to zero for statistical purposes.

Plasma levels and kidney tissue concentrations of tumor necrosis factor (TNF)-α, interleukin (IL)-6 and IL-10, monocyte chemoattractant protein (MCP)-1, and keratinocyte-derived chemokine (KC) were determined using a commercially available "Multiplex Cytokine Kit" (Bio-Plex Pro Precision Pro Cytokine Assay, Bio-Rad, Hercules, Calif.), which allows to collect several parameters out of one single sample. The individual work steps of the assay were performed according to the manufacturer's instructions (see also Wagner F, Wagner K, Weber S, Stahl B, Knöferl M W, Huber-Lang M, Seitz D H, Asfar P, Calzia E, Senftleben U, Gebhard F, Georgieff M, Radermacher P, Hysa V Inflammatory effects of hypothermia and inhaled H2S during resuscitated, hyperdynamic murine septic shock. Shock 2011; 35:396-402; and Wagner F, Scheuerle A, Weber S, Stahl B, McCook O, Knöferl M W, Huber-Lang M, Seitz D H, Thomas J, Asfar P, Szabó C, Möller P, Gebhard F, Georgieff M, Calzia E, Radermacher P, Wagner K. Cardiopulmonary, histologic, and inflammatory effects of intravenous Na2S after blunt chest trauma-induced lung contusion in mice. J Trauma 2011; 71:1659-1667).

In brief, the fluorescence-labeled microspheres ("beads") were added to a 96-well plate, followed by two washing steps, the addition of internal standards and the addition of plasma- and kidney homogenate samples. During the subsequent incubation the single cytokines bind to the antibodies attached to polystyrene-beads. After the addition of the cytokine-specific biotin-labeled antibodies, which are for the detection of the single cytokines, and an additional incubation time, subsequently phycoerythrin-labeled streptavidine was added. After an additional incubation time, beads were then resuspended, and the plates could be measured with a specific flow cytometer (Bio-Plex suspension array system, Bio-Rad, Hercules, Calif.). Data were automatically processed and analyzed by Bio-Plex Manager Software 4.1 using the standard curve produced from recombinant cytokine standards. For the plasma levels the concentration was provided in $pg*mL^{-1}$, the concentration of the kidney homogenates were converted to the appropriate protein concentration and provided in $pg*mg^{-1}$ protein.

Figure 17:
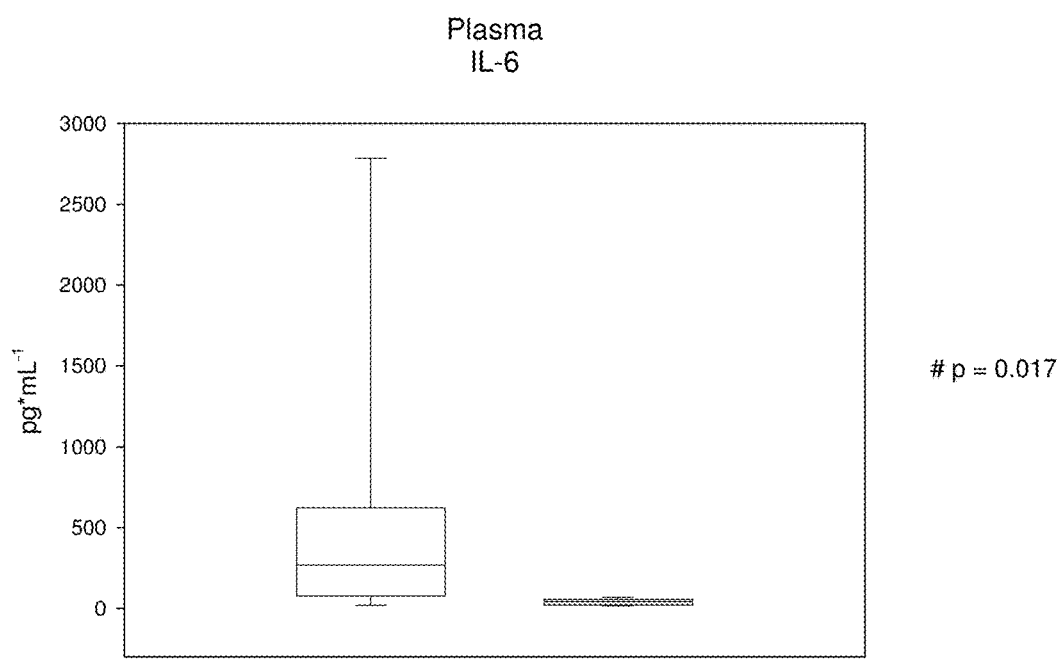
FIG. 17—Plasma IL-6 levels. The white box-plot shows results obtained with vehicle, the grey box-plot shows results obtained after treatment with NT-M.
Figure 18:
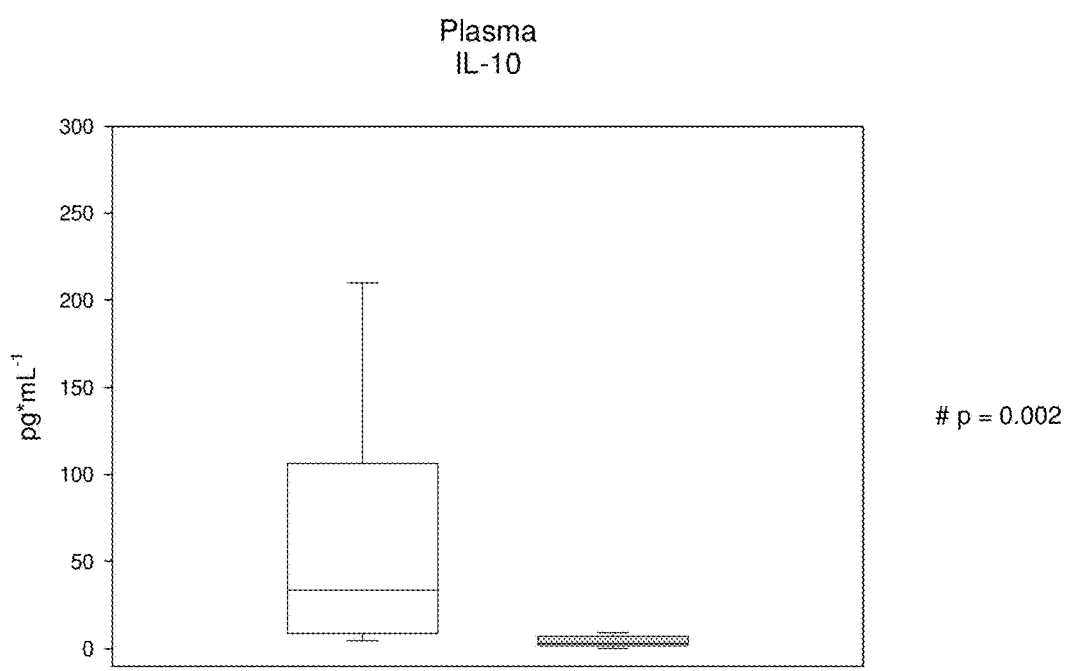
FIG. 18—Plasma IL-10 levels. The white box-plot shows results obtained with vehicle, the grey box-plot shows results obtained after treatment with NT-M.
Figure 19:
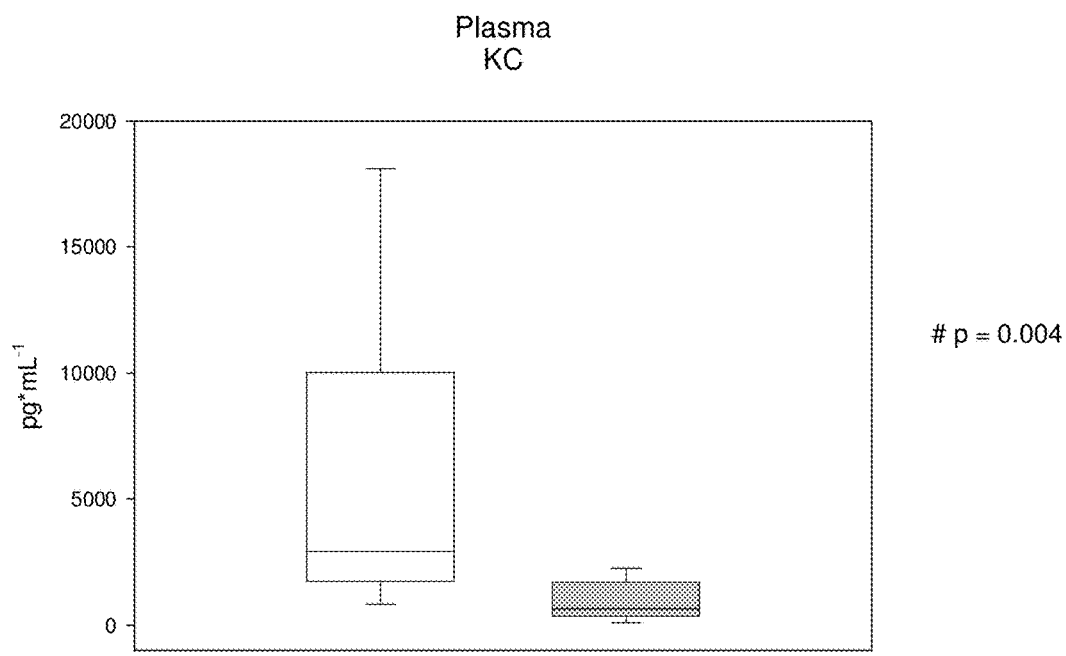
FIG. 19—Plasma keratinocyte-derived chemokine (KC) levels. The white box-plot shows results obtained with vehicle, the grey box-plot shows results obtained after treatment with NT-M.
Figure 20:
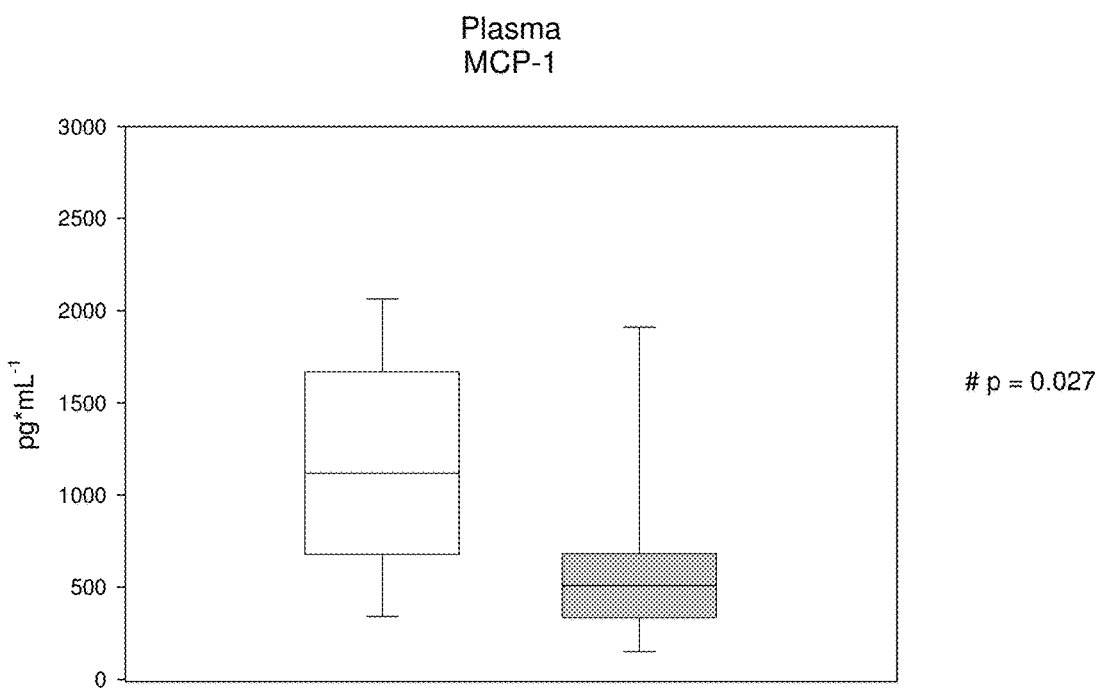
FIG. 20—Plasma monocyte chemoattractant protein-1 (MCP-1) levels. The white box-plot shows results obtained with vehicle, the grey box-plot shows results obtained after treatment with NT-M.
Figure 21:
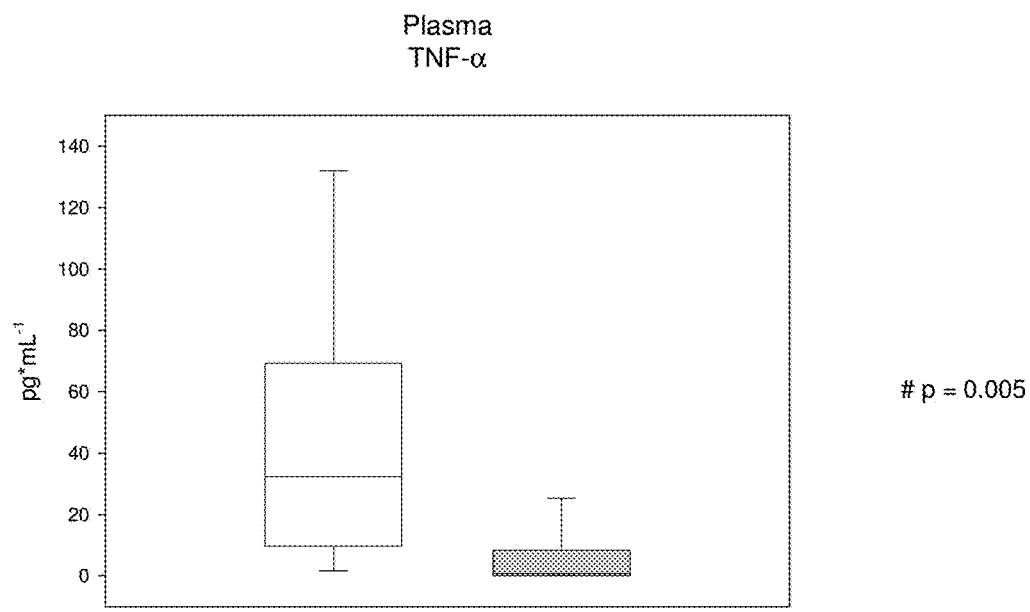
FIG. 21—Plasma TNF-alpha levels. The white box-plot shows results obtained with vehicle, the grey box-plot shows results obtained after treatment with NT-M.

NT-M caused a significant lowering of plasma concentrations of IL-6 (FIG. 17), IL-10 (FIG. 18), keratinocyte-derived chemokine (KC) (FIG. 19), monocyte chemoattractant protein-1 (MCP-1) (FIG. 20), TNF-alpha (FIG. 21).

Example 11

Ischemia/Reperfusion-Induced Acute Kidney Injury

Another non-septic acute kidney injury model has been established, where acute kidney injury is induced by ischemia/reperfusion (Nakamoto M, Shapiro J I, Shanley P F, Chan L, and Schrier R W. In vitro and in vivo protective effect of atriopeptin III on ischemic acute renal failure. J ClinInvest 80:698-705, 1987., Chintala M S, Bernardino V, and Chiu P J S. Cyclic GMP but not cyclic AMP prevents renal platelet accumulation following ischemia-reperfusion in anesthetized rats. J Pharmacol Exp Ther 271:1203-1208, 1994). This model was used to assess whether treatment with anti-adrenomedullin antibody can improve kidney function.

The experiment was performed as follows:

Effect of a NT-M on Acute Kidney Injury Induced by Ischemia/Reperfusion in Rats
Study Design:

| Group | Test Article | Route | Conc mg/ml | Dosage ml/kg | mg/kg | Rats (Male) |
|---|---|---|---|---|---|---|
| 1 | I-R + vehicle[a] | IV | | 5 | NA × 3 | 8 |
| 2 | I-R + NT-M | IV | | 5 | ×3[b] | 8 |

[a]vehicle; injected intravenously (i.v.) 5 min before reperfusion on day 0, followed by injections on days 1 and 2.
[b]NT-M at 4 mg/kg was injected intravenously (i.v.) 5 min before reperfusion on day 0, followed by 2 mg/kg i.v. each on days 1 and 2.
[c]Urine collection on days −1, 0, 1 and 2, with blood chemistry and urine analysis on days 0, 1, 2 and 3, respectively. Plasma samples were collected in EDTA tubes (Days 0 (immediate before surgery), 1, 2: 100 µl, before vehicle or TA; Day 3:120 µl.
Clinical observations: daily before surgery, following surgery and throughout treatment.

Groups of 8 male Sprague-Dawley rats weighing 250 to 280 g were used. The animals were kept on a 12-hr light/dark cycle and receive a standard diet with distilled water ad libitum. The animals receive fluid supplements (0.9% NaCl and 5% dextrose/1:1, 10 ml/kg p.o.) 30 min prior to surgery (day 0). The rats were anaesthetized with pentobarbital (50 mg/kg, i.p.). The abdominal cavity was exposed via a midline incision, followed by intravenous administration of heparin (100 U/kg, i.v.) and both renal arteries were occluded for 45 min by using vascular clamps. Immediately after removal of the renal clips, the kidneys were observed for additional 1 min to ensure color change indicating blood reperfusion. The test compound (NT-M) and vehicle (phosphate buffered saline) were injected intravenously 5 min before reperfusion, followed by daily injection on days 1 and 2.

Urine collection. The 24-h urine collection on ice was initiated at 24 h before ischemia/reperfusion on day −1 (−24 h to 0 h), and day 0 (0-24 h), day 1 (24-48 h) and day 2 (48-72 h) after reperfusion, Blood collection: 0.4 ml blood was collected through the tail vein into EDTA tubes at 0 h (before I RI surgery), 24 h (before vehicle or TA), 48 h (before vehicle or TA) and 72 h for determination of plasma creatinine/Na+/K+, and BUN; 2 ml blood was collected through venal cava terminally.

The animals were placed in individual cages where urine was collected for 24 h day −1 (−24 h-0 h), day 0 (0-24 h), day 1 (24-48 h) and day 2 (48-72 h) after reperfusion on day 0.

Urine volume, urinary Na+, K+, and creatinine were measured.

The creatinine clearance (CCr) was calculated as follows:

$$CCr\ (ml/24\ h) = [UCr\ (mg/ml) \times V\ (ml/24\ h)]/PCr\ (mg/ml)$$

The 24-hr urinary excretion of sodium (Na+) was calculated as follows:

$$UNaV\ (\mu Eq/24\ h) = UNa\ (\mu Eq/ml) \times V\ (ml/24\ h)$$

The fractional excretion of Na+(FENa), or percentage of the filtered sodium that is excreted into the final urine, is a measure of tubular Na+ reabsorptive function. It was computed as follows:

$$FENa\ (\%) = 100 \times [UNa\ (\mu Eq/ml) \times V\ (ml/24\ h)]/PNa\ (\mu Eq/ml) \times CCr\ (ml/24\ h)$$

Figure 22:
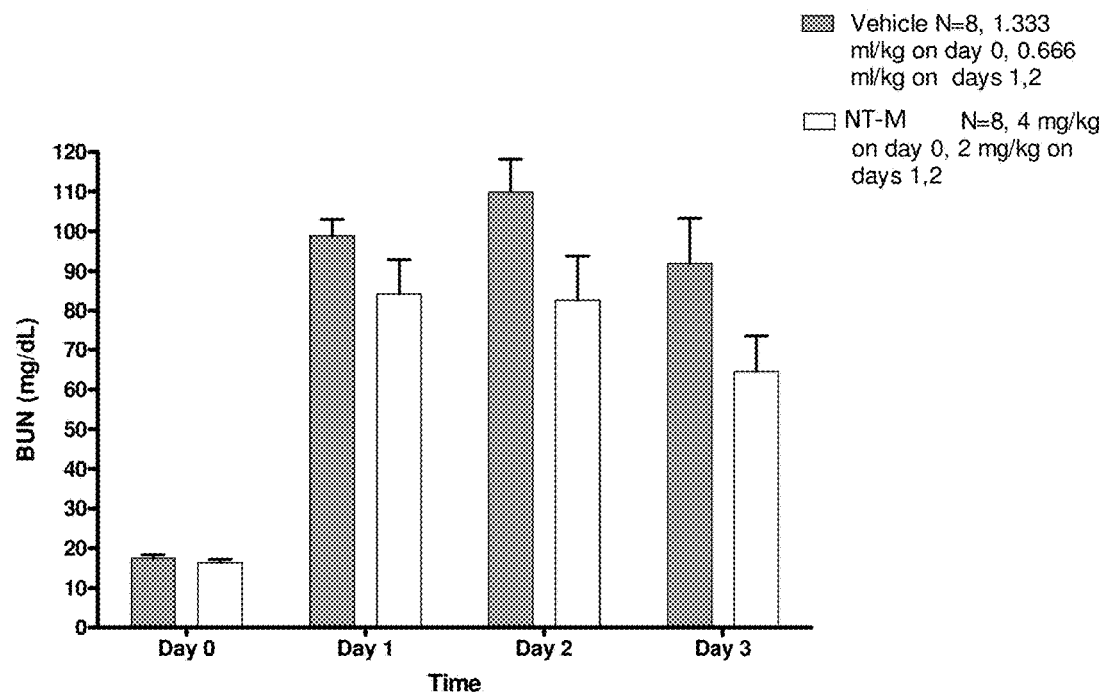
FIG. 22—Development of blood urea nitrogen (BUN) over time. Mean+/−SEM are shown.

Treatment with anti-Adrenomedullin antibody improved several measures of kidney function:

Blood urea nitrogen (BUN) showed a strong increase in the vehicle group (0 h: 17.49 mg/dL, 24 h: 98.85 mg/dL, 48 h: 109.84 mg/dL, 72 h: 91.88 mg/dL), which was less pronounced with NT-M treatment (0 h: 16.33 mg/dL, 24 h: 84.2 mg/dL, 48 h: 82.61 mg/dL, 72 h: 64.54 mg/dL) (FIG. 22).

Figure 23:
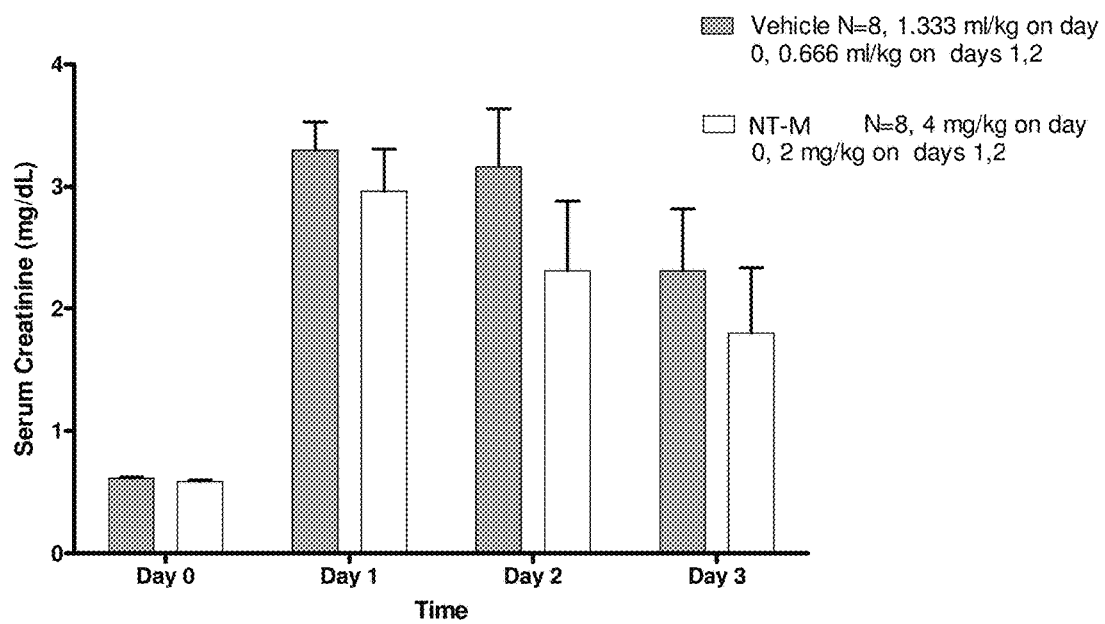
FIG. 23—Development of serum creatinine over time. Mean+/−SEM are shown.

Serum creatinine developed similarly: Vehicle group (0 h: 0.61 mg/dL, 24 h: 3.3 mg/dL, 48 h: 3.16 mg/dL, 72 h: 2.31 mg/dL), NT-M group: (0 h: 0.59 mg/dL, 24 h: 2.96 mg/dL, 48 h: 2.31 mg/dL, 72 h: 1.8 mg/dL) (FIG. 23).

Figure 24:
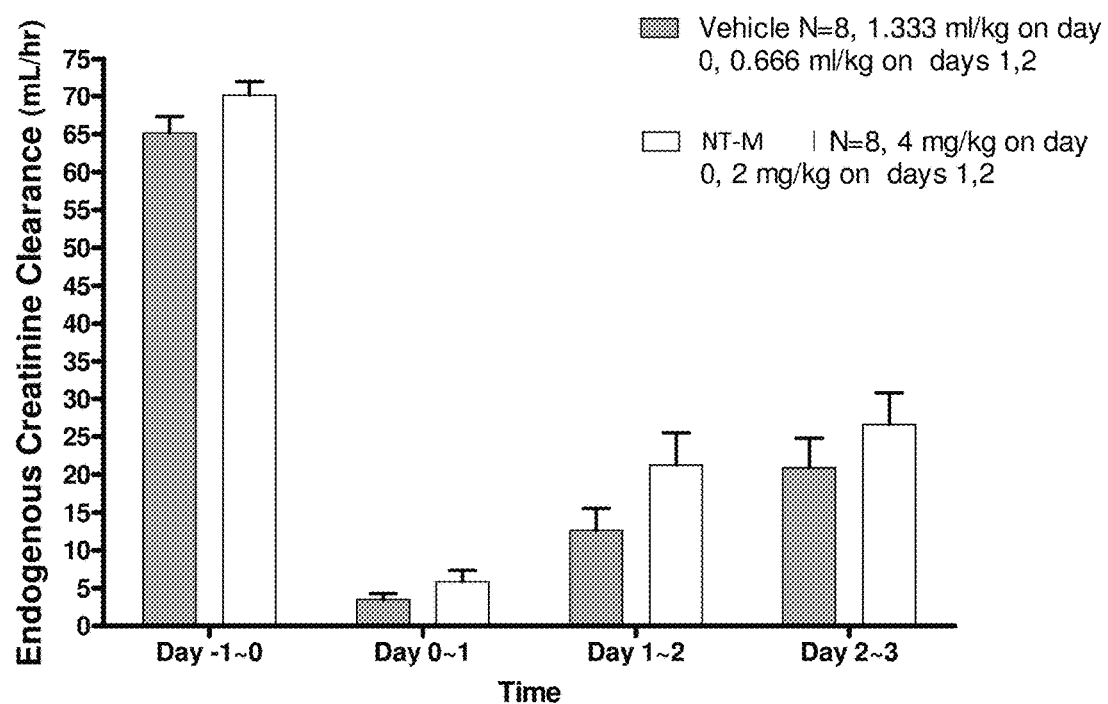
FIG. 24—Development of endogenous creatinine clearance over time. Mean+/−SEM are shown.

The endogenous creatinine clearance dropped massively on day one and thereafter improved better in the NT-M group than in the vehicle group. Vehicle group: (0 h: 65.17 mL/h, 24 h: 3.5 mL/h, 48 h: 12.61 mL/h, 72 h: 20.88 mL/h), NT-M group: (0 h: 70.11 mL/h, 24 h: 5.84 mL/h, 48 h: 21.23 mL/h, 72 h: 26.61 mL/h) (FIG. 24).

SEQUENCE LISTING

<160> NUMBER OF SEQ ID NOS: 33

<210> SEQ ID NO 1
<211> LENGTH: 8

```
<212> TYPE: PRT
<213> ORGANISM: Homo sapiens

<400> SEQUENCE: 1

Gly Tyr Thr Phe Ser Arg Tyr Trp
1               5

<210> SEQ ID NO 2
<211> LENGTH: 8
<212> TYPE: PRT
<213> ORGANISM: Homo sapiens

<400> SEQUENCE: 2

Ile Leu Pro Gly Ser Gly Ser Thr
1               5

<210> SEQ ID NO 3
<211> LENGTH: 11
<212> TYPE: PRT
<213> ORGANISM: Homo sapiens

<400> SEQUENCE: 3

Thr Glu Gly Tyr Glu Tyr Asp Gly Phe Asp Tyr
1               5                   10

<210> SEQ ID NO 4
<211> LENGTH: 11
<212> TYPE: PRT
<213> ORGANISM: Homo sapiens

<400> SEQUENCE: 4

Gln Ser Ile Val Tyr Ser Asn Gly Asn Thr Tyr
1               5                   10

<210> SEQ ID NO 5
<211> LENGTH: 3
<212> TYPE: PRT
<213> ORGANISM: Homo sapiens

<400> SEQUENCE: 5

Arg Val Ser
1

<210> SEQ ID NO 6
<211> LENGTH: 9
<212> TYPE: PRT
<213> ORGANISM: Homo sapiens

<400> SEQUENCE: 6

Phe Gln Gly Ser His Ile Pro Tyr Thr
1               5

<210> SEQ ID NO 7
<211> LENGTH: 225
<212> TYPE: PRT
<213> ORGANISM: Homo sapiens

<400> SEQUENCE: 7

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45
```

-continued

```
Gly Glu Ile Leu Pro Gly Ser Gly Ser Thr Asn Tyr Asn Glu Lys Phe
         50                  55                  60

Lys Gly Lys Ala Thr Ile Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Thr Glu Gly Tyr Glu Tyr Asp Gly Phe Asp Tyr Trp Gly Gln Gly Thr
                100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225

<210> SEQ ID NO 8
<211> LENGTH: 225
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Arg Tyr
             20                  25                  30

Trp Ile Ser Trp Val Arg Gln Ala Pro Gly Gln Gly Leu Glu Trp Met
         35                  40                  45

Gly Arg Ile Leu Pro Gly Ser Gly Ser Thr Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Glu Gly Tyr Glu Tyr Asp Gly Phe Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
                180                 185                 190
Ser Leu Gly Thr Gln Thr Tyr Ile Cys Asn Val Asn His Lys Pro Ser
            195                 200                 205

Asn Thr Lys Val Asp Lys Arg Val Glu Pro Lys His His His His
            210                 215                 220

His
225

<210> SEQ ID NO 9
<211> LENGTH: 225
<212> TYPE: PRT
<213> ORGANISM: Homo sapiens

<400> SEQUENCE: 9

Gln Val Gln Leu Val Gln Ser Gly Ala Glu Val Lys Lys Pro Gly Ser
1               5                  10                  15

Ser Val Lys Val Ser Cys Lys Ala Ser Gly Tyr Thr Phe Ser Arg Tyr
            20                  25                  30

Trp Ile Glu Trp Val Arg Gln Ala Pro Gly Gln Gly Leu Glu Trp Met
        35                  40                  45

Gly Arg Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225

<210> SEQ ID NO 10
<211> LENGTH: 225
<212> TYPE: PRT
<213> ORGANISM: Homo sapiens

<400> SEQUENCE: 10

Gln Val Gln Leu Val Gln Ser Gly Ala Glu Val Lys Lys Pro Gly Ser
1               5                  10                  15

Ser Val Lys Val Ser Cys Lys Ala Thr Gly Tyr Thr Phe Ser Arg Tyr
            20                  25                  30

Trp Ile Ser Trp Val Arg Gln Ala Pro Gly Gln Gly Leu Glu Trp Met
```

```
            35                  40                  45
Gly Glu Ile Leu Pro Gly Ser Gly Ser Thr Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Glu Gly Tyr Glu Tyr Asp Gly Phe Asp Tyr Trp Gly Gln Gly Thr
                100                 105                 110

Thr Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys His His His His
210                 215                 220

His
225

<210> SEQ ID NO 11
<211> LENGTH: 225
<212> TYPE: PRT
<213> ORGANISM: Homo sapiens

<400> SEQUENCE: 11

Gln Val Gln Leu Val Gln Ser Gly Ala Glu Val Lys Lys Pro Gly Ser
 1               5                  10                  15

Ser Val Lys Val Ser Cys Lys Ala Thr Gly Tyr Thr Phe Ser Arg Tyr
                 20                  25                  30

Trp Ile Glu Trp Val Arg Gln Ala Pro Gly Gln Gly Leu Glu Trp Met
             35                  40                  45

Gly Glu Ile Leu Pro Gly Ser Gly Ser Thr Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Glu Gly Tyr Glu Tyr Asp Gly Phe Asp Tyr Trp Gly Gln Gly Thr
                100                 105                 110

Thr Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys His His His His
        210                 215                 220

His
225

<210> SEQ ID NO 12
<211> LENGTH: 219
<212> TYPE: PRT
<213> ORGANISM: Homo sapiens

<400> SEQUENCE: 12

Asp Val Leu Leu Ser Gln Thr Pro Leu Ser Leu Pro Val Ser Leu Gly
 1               5                  10                  15

Asp Gln Ala Thr Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
         35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Ile Pro Tyr Thr Phe Gly Gly Gly Thr Lys Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 219
<212> TYPE: PRT
<213> ORGANISM: Homo sapiens

<400> SEQUENCE: 13

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val Tyr Ser
            20                  25                  30

Asn Gly Asn Thr Tyr Leu Asn Trp Phe Gln Gln Arg Pro Gly Gln Ser
         35                  40                  45
```

```
Pro Arg Arg Leu Ile Tyr Arg Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 219
<212> TYPE: PRT
<213> ORGANISM: Homo sapiens

<400> SEQUENCE: 14

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val Tyr Ser
             20                  25                  30

Asn Gly Asn Thr Tyr Leu Glu Trp Phe Gln Gln Arg Pro Gly Gln Ser
         35                  40                  45

Pro Arg Arg Leu Ile Tyr Arg Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 15
<211> LENGTH: 21
<212> TYPE: PRT
<213> ORGANISM: Homo sapiens

<400> SEQUENCE: 15

Tyr Arg Gln Ser Met Asn Asn Phe Gln Gly Leu Arg Ser Phe Gly Cys
1               5                   10                  15

Arg Phe Gly Thr Cys
            20

<210> SEQ ID NO 16
<211> LENGTH: 12
<212> TYPE: PRT
<213> ORGANISM: Homo sapiens

<400> SEQUENCE: 16

Cys Thr Val Gln Lys Leu Ala His Gln Ile Tyr Gln
1               5                   10

<210> SEQ ID NO 17
<211> LENGTH: 14
<212> TYPE: PRT
<213> ORGANISM: Homo sapiens

<400> SEQUENCE: 17

Cys Ala Pro Arg Ser Lys Ile Ser Pro Gln Gly Tyr Asn His
1               5                   10

<210> SEQ ID NO 18
<211> LENGTH: 19
<212> TYPE: PRT
<213> ORGANISM: Homo sapiens

<400> SEQUENCE: 18

Tyr Arg Gln Ser Met Asn Gln Gly Ser Arg Ser Asn Gly Cys Arg Phe
1               5                   10                  15

Gly Thr Cys

<210> SEQ ID NO 19
<211> LENGTH: 12
<212> TYPE: PRT
<213> ORGANISM: Homo sapiens

<400> SEQUENCE: 19

Cys Thr Phe Gln Lys Leu Ala His Gln Ile Tyr Gln
1               5                   10

<210> SEQ ID NO 20
<211> LENGTH: 14
<212> TYPE: PRT
<213> ORGANISM: Homo sapiens

<400> SEQUENCE: 20

Cys Ala Pro Arg Asn Lys Ile Ser Pro Gln Gly Tyr Asn His
1               5                   10

<210> SEQ ID NO 21
<211> LENGTH: 54
<212> TYPE: PRT

<213> ORGANISM: Homo sapiens

<400> SEQUENCE: 21

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr Asn His
    50

<210> SEQ ID NO 22
<211> LENGTH: 52
<212> TYPE: PRT
<213> ORGANISM: Homo sapiens

<400> SEQUENCE: 22

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
            20                  25                  30

Asp Lys Asp Lys Asp Gly Met Ala Pro Arg Asn Lys Ile Ser Pro Gln
        35                  40                  45

Gly Tyr Asn His
    50

<210> SEQ ID NO 23
<211> LENGTH: 21
<212> TYPE: PRT
<213> ORGANISM: Homo sapiens

<400> SEQUENCE: 23

Tyr Arg Gln Ser Met Asn Asn Phe Gln Gly Leu Arg Ser Phe Gly Cys
1               5                   10                  15

Arg Phe Gly Thr Cys
            20

<210> SEQ ID NO 24
<211> LENGTH: 42
<212> TYPE: PRT
<213> ORGANISM: Homo sapiens

<400> SEQUENCE: 24

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala
        35                  40

<210> SEQ ID NO 25
<211> LENGTH: 12
<212> TYPE: PRT
<213> ORGANISM: Homo sapiens

<400> SEQUENCE: 25

Pro Arg Ser Lys Ile Ser Pro Gln Gly Tyr Asn His
1               5                   10

<210> SEQ ID NO 26
<211> LENGTH: 14
<212> TYPE: PRT
<213> ORGANISM: Homo sapiens

<400> SEQUENCE: 26

Tyr Arg Gln Ser Met Asn Asn Phe Gln Gly Leu Arg Ser Phe
1               5                   10

<210> SEQ ID NO 27
<211> LENGTH: 10
<212> TYPE: PRT
<213> ORGANISM: Homo sapiens

<400> SEQUENCE: 27

Tyr Arg Gln Ser Met Asn Asn Phe Gln Gly
1               5                   10

<210> SEQ ID NO 28
<211> LENGTH: 6
<212> TYPE: PRT
<213> ORGANISM: Homo sapiens

<400> SEQUENCE: 28

Tyr Arg Gln Ser Met Asn
1               5

<210> SEQ ID NO 29
<211> LENGTH: 32
<212> TYPE: PRT
<213> ORGANISM: Homo sapiens

<400> SEQUENCE: 29

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

<210> SEQ ID NO 30
<211> LENGTH: 40
<212> TYPE: PRT
<213> ORGANISM: Homo sapiens

<400> SEQUENCE: 30

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
                20                  25                  30

Asp Lys Asp Lys Asp Gly Met Ala
            35                  40

<210> SEQ ID NO 31
<211> LENGTH: 31
<212> TYPE: PRT
<213> ORGANISM: Homo sapiens

<400> SEQUENCE: 31

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu
                20                  25                  30

<210> SEQ ID NO 32

```
<211> LENGTH: 118
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser
            115

<210> SEQ ID NO 33
<211> LENGTH: 118
<212> TYPE: PRT
<213> ORGANISM: Homo sapiens

<400> SEQUENCE: 33

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Leu Thr Val Ser Ser
            115
```

The invention claimed is:

1. A method of modulating the activity of adrenomedullin in a subject in need of therapeutic intervention for organ dysfunction or organ failure associated with adrenomedullin (ADM) activity, wherein the organ is one or more of heart, kidney, liver, lung, pancreas, small intestine or spleen, comprising administering an anti-adrenomedullin (ADM) antibody or an anti-ADM antibody fragment to the subject, wherein said antibody or antibody fragment binds to a region of at least 4 amino acids within the sequence of aa 1-42 of mature human ADM: YRQSMNNFQGLRSFGCR-FGTCTVQKLAHQIYQFTDKDKDNVA (SEQ ID NO: 24), and wherein said antibody or antibody fragment does not bind to the C-terminal portion of ADM (aa 43-52 of ADM (SEQ ID NO: 25)), and wherein said antibody or antibody fragment is a monoclonal antibody or antibody fragment having a heavy chain comprising the following sequences:

```
                             SEQ ID NO: 1
            GYTFSRYW,

SEQ ID NO: 2
            ILPGSGST,
            and

SEQ ID NO: 3
            TEGYEYDGFDY
``` and a light chain comprising the following sequences:

```
                             SEQ ID NO: 4
            QSIVYSNGNTY,

SEQ ID NO: 5
            RVS,
            and

SEQ ID NO: 6
            FQGSHIPYT.
```

2. A method of claim 1 wherein said organ is kidney or liver.

3. A method of claim 1 wherein said organ is heart.

4. A method of claim 1 wherein said antibody or fragment binds to a region of at least 4 amino acids within the sequence of aa 1-21 of mature human ADM: YRQSMNN-FQGLRSFGCRFGTC (SEQ ID NO: 23).

5. A method of claim 1 wherein said antibody or antibody fragment exhibits a binding affinity to ADM of at least $10^{-7}$ M.

6. A method of claim 1 wherein said antibody or antibody fragment is not ADM-binding-Protein-1 (complement factor H).

7. A method of claim 1 wherein said antibody or antibody fragment binds to an epitope including amino acid 1 of mature human ADM.

8. A method of claim 1 wherein said antibody or antibody fragment is an ADM stabilizing antibody or antibody fragment that enhances the half life ($t_{1/2}$ half retention time) of adrenomedullin in serum, blood or plasma at least 10%.

9. A method of claim 1 wherein said antibody or antibody fragment blocks the ADM bioactivity not more than 80%.

10. A method of claim 1 wherein said subject is suffering from a disease selected from sepsis, diabetes, cancer, heart failure, and shock.

11. A method of claim 10 wherein said disease is not sepsis, or septic shock.

12. A method of claim 1 wherein said antibody or antibody fragment comprises a heavy chain which comprises a sequence selected from SEQ ID NOS: 7-11:

```
(AM-VH-C)
                                              SEQ ID NO: 7
QVQLQQSGAELMKPGASVKISCKATGYTFSRYWIEWVKQRPGHGLEWIG

EILPGSGSTNYNEKFKGKATITADTSSNTAYMQLSSLTSEDSAVYYCTE

GYEYDGFDYWGQGTTLTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKHHHHHH, (AM-VH1)
                                              SEQ ID NO: 8
QVQLVQSGAEVKKPGSSVKVSCKASGYTFSRYWISWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKHHHHHH, (AM-VH2-E40)
                                              SEQ ID NO: 9
QVQLVQSGAEVKKPGSSVKVSCKASGYTFSRYWIEWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKHHHHHH, (AM-VH3-T26-E55)
                                              SEQ ID NO: 10
QVQLVQSGAEVKKPGSSVKVSCKATGYTFSRYWISWVRQAPGQGLEWMG

EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKHHHHHH, (AM-VH4-T26-E40-E55)
                                              SEQ ID NO: 11
QVQLVQSGAEVKKPGSSVKVSCKATGYTFSRYWIEWVRQAPGQGLEWMG

EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKHHHHHH,
``` and comprises a light chain which comprises a sequence selected from SEQ ID NOS: 12-14:

```
(AM-VL-C)
                                              SEQ ID NO: 12
DVLLSQTPLSLPVSLGDQATISCRSSQSIVYSNGNTYLEWYLQKPGQSP

KLLIYRVSNRFSGVPDRFSGSGSGTDFTLKISRVEAEDLGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC, (AM-VL1)
                                              SEQ ID NO: 13
DVVMTQSPLSLPVTLGQPASISCRSSQSIVYSNGNTYLNWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC, (AM-VL2-E40)
                                              SEQ ID NO: 14
DVVMTQSPLSLPVTLGQPASISCRSSQSIVYSNGNTYLEWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR
```

-continued

EAKVQWKVDNALQSGNSQESVTEQDSKDSTYSLSSTLTLSKADYEKHKV

YACEVTHQGLSSPVTKSFNRGEC.

13. A method of claim 1 wherein said antibody or antibody fragment is a modulating antibody or antibody fragment that enhances the half life ($t_{1/2}$ half retention time) of adrenomedullin in serum, blood or plasma at least 10% and that blocks the ADM bioactivity not more than 80%.

14. A method of claim 1 further comprising administering a vasopressor and/or fluids intravenously.

15. A method of claim 1 wherein said antibody or antibody fragment is in a pharmaceutical formulation comprising one or more pharmaceutically acceptable excipients.

16. A method of claim 15 wherein said pharmaceutical formulation is a solution.

17. A method of claim 16 wherein the solution is a ready-to-use solution.

18. A method of claim 15 wherein said pharmaceutical formulation is administered intra-muscularly.

19. A method of claim 15 wherein said pharmaceutical formulation is administered intra-vascularly.

20. A method of claim 15 wherein said pharmaceutical formulation is administered via infusion.

21. A method of claim 15 wherein said pharmaceutical formulation is administered systemically.

* * * * *